(12) United States Patent
Burgard et al.

(10) Patent No.: US 8,617,862 B2
(45) Date of Patent: Dec. 31, 2013

(54) MICROORGANISMS FOR PRODUCING PROPYLENE AND METHODS RELATED THERETO

(75) Inventors: Anthony P. Burgard, Bellefonte, PA (US); Robin E. Osterhout, San Diego, CA (US); Jun Sun, San Diego, CA (US); Priti Pharkya, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 13/527,455

(22) Filed: Jun. 19, 2012

(65) Prior Publication Data

US 2012/0329119 A1    Dec. 27, 2012

Related U.S. Application Data

(60) Provisional application No. 61/500,087, filed on Jun. 22, 2011.

(51) Int. Cl.
*C12P 5/02* (2006.01)
*C12P 5/00* (2006.01)
*C12P 1/04* (2006.01)

(52) U.S. Cl.
USPC .......................... 435/167; 435/170; 435/166

(58) Field of Classification Search
None
See application file for complete search history.

(56) References Cited

U.S. PATENT DOCUMENTS

| | | | |
|---|---|---|---|
| 4,698,304 | A | 10/1987 | Fukuda et al. |
| 7,127,379 | B2 | 10/2006 | Palsson et al. |
| 7,947,483 | B2 | 5/2011 | Burgard et al. |
| 2002/0012939 | A1 | 1/2002 | Palsson |
| 2002/0168654 | A1 | 11/2002 | Maranas et al. |
| 2003/0059792 | A1 | 3/2003 | Palsson et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2009/0047719 | A1 | 2/2009 | Burgard et al. |
| 2011/0269204 | A1* | 11/2011 | Burk et al. .................... 435/167 |

FOREIGN PATENT DOCUMENTS

| WO | WO 02/055995 | 7/2002 |
|---|---|---|
| WO | WO 03/106998 | 12/2003 |
| WO | WO 2008/080124 | 7/2008 |
| WO | WO 2010/044960 | 4/2010 |

OTHER PUBLICATIONS

Kornberg, H. "Aspects of Terminal Respiration in Microorganisms" Annu. Rev. Microbiol. 13 49-78.*

Adams et al., "Oxidoreductase-type enzymes and redox proteins involved in fermentative metabolisms of hyperthermophilic Archaea," *Adv. Protein Chem.* 48:101-180 (1996).
Alhapel et al., "Molecular and functional analysis of nicotinate catabolism in *Eubacterium barkeri*," *Proc. Natl. Acad. Sci. U.S.A.* 103(33):12341-12346 (2006).
Aoshima et al., "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).
Aoshima et al., "A novel enzyme, citryl-CoA lyase, catalysing the second step of the citrate cleavage reaction in *Hydrogenobacter thermophilus* TK-6," *Mol. Microbiol.* 52:763-770 (2004).
Aoshima et al., "A novel enzyme, citryl-CoA synthetase, catalysing the first step of the citrate cleavage reaction in *Hydrogenobacter thermophilus* TK-6," *Mol. Microbiol.* 52(3):751-761 (2004).
Aoshima et al., "A novel oxalosuccinate-forming enzyme involved in the reductive carboxylation of 2-oxoglutarate in *Hydrogenobacter thermophilus* TK-6," *Mol. Microbiol.* 62(3):748-759 (2006).
Aoshima et al., "Nondecarboxylating and decarboxylating isocitrate dehydrogenases: oxalosuccinate reductase as an ancestral form of isocitrate dehydrogenase," *J. Bacteriol.* 190(6):2050-2055 (2008).
Aoshima, M., "Novel enzyme reactions related to the tricarboxylic acid cycle: phylogenetic/functional implications and biotechnological applications," *Appl. Microbiol. Biotechnol.* 75(2):249-255 (2007).
Arikawa et al., "Soluble fumarate reductase isoenzymes from *Saccharomyces cerevisiae* are required for anaerobic growth," *FEMS Microbiol. Lett.* 165:111-116 (1998).
Arps et al., "Genetics of Serine Pathway Enzymes in *Methylobacterium extorquens* AM1: Phosphoenolpyruvate Carboxylase and Malyl Coenzyme A Lyase," *J. Bacteriol.* 175(12):3776-3783 (1993).
Bekal et al., "Purification of *Leuconostoc mesenteroides* citrate lyase and cloning and characterization of the citCDEFG gene cluster," *J. Bacteriol.* 180(3):647-654 (1998).
Bernhard et al., "Functional and structural role of the cytochrome b subunit of the membrane-bound hydrogenase complex of *Alcaligenes eutrophus* H16," *Eur. J. Biochem.* 248(1):179-186 (1997).
Bergquist and Gibbs, "Degenerate oligonucleotide gene shuffling," *Meth. Mol. Biol.* 352:191-204 (2007).
Bergquist et al., "Degenerate oligonucleotide gene shuffling (DOGS) and random drift mutagenesis (RNDM): Two complementary techniques for enzyme evolution," *Biomol. Eng.* 22:63-72 (2005).
Bisswanger, "Substrate Specificity of the Pyruvate Dehydrogenase Complex from *Escherichi coli*," *J. Biol. Chem.* 256(2):815-822 (1981).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Bock et al., "Purification and characterization of two extremely thermostable enzymes, phosphate acetyltransferase and acetate kinase, from the hyperthermophilic eubacterium *Thermotoga maritima*," *J. Bacteriol.* 181:1861-1867 (1999).

(Continued)

*Primary Examiner* — John S Brusca
*Assistant Examiner* — Gerard LaCourciere
(74) *Attorney, Agent, or Firm* — Jones Day

(57) ABSTRACT

The invention provides non-naturally occurring microbial organisms having a propylene pathway. The invention additionally provides methods of using such organisms to produce propylene.

10 Claims, 20 Drawing Sheets

(56) References Cited

OTHER PUBLICATIONS

Bott et al., "*Klebsiella pneumoniae* genes for citrate lyase and citrate lyase ligase: localization, sequencing, and expression," *Mol. Microbiol.* 14(2):347-356 (1994).
Bott, "Anaerobic citrate metabolism and its regulation in enterobacteria," *Arch. Microbiol.* 167(2/3):78-88 (1997).
Brown et al., "The enzymic interconversion of acetate and acetyl-coenzyme A in *Escherichia coli*," *J. Gen. Microbiol.* 102(2):327-336 (1977).
Buck et al., "Primary Structure of the Succinyl-CoA Synthetase of *Escherichia coli*," *Biochemistry* 24:6245-6252 (1985).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burgdorf et al., "The soluble NAD+-Reducing [NiFe]-hydrogenase from *Ralstonia eutropha* H16 consists of six subunits and can be specifically activated by NADPH," *J. Bacteriol.* 187(9):3122-3132 (2005).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Camara et al., "Characterization of a Gene Cluster Involved in 4-Chlorocatechol Degradation by *Pseudomonas reinekei* MT1," *J. Bacteriol.* 191(15):4905-4915 (2009).
Chen et al., "Overexpression of bacterial ethylene-forming enzyme gene in *Trichoderma reesei* enhanced the production of ethylene," *Int. J. Biol. Sci.* 6(1):96-106 (2010).
Clark, "Molybdenum cofactor negative mutants of *Escherichia coli* use citrate anaerobically," *FEMS Micobiol. Lett.* 55(3):245-249 (1990).
Coco et al., "DNA shuffling method for generating highly recombined genes and evolved enzymes," *Nat. Biotechnol.* 19:354-359 (2001).
Coppi, "The hydrogenases of *Geobacter sulfurreducens*: a comparative genomic perspective," *Microbiology* 151(Pt 4):1239-1254 (2005).
Cracknell et al., "A kinetic and thermodynamic understanding of $O_2$ tolerance in [NiFe]-hydrogenases," *Proc. Nat. Acad. Sci. U.S.A.* 106(49):20681-20686 (2009).
Cunningham et al., "Transcriptional regulation of the aconitase genes (acnA and acnB) of *Escherichia coli*," *Microbiology* 143(pt. 12):3795-3805 (1997).
Dagley, S., "4-Hydroxy-4-methyl-2-ketoglutarate aldolase from *Pseudomonas putida*," *Methods Enzymol.* 90 Pt E:272-276 (1982).
Dobbek et al., "Crystal structure of a carbon monoxide dehydrogenase reveals a [Ni-4Fe-5S] cluster," *Science* 293(5533):1281-1285 (2001).
Dorner et al., "Properties of 2-oxoglutarate:ferredoxin oxidoreductase from *Thauera aromatica* and its role in enzymatic reduction of the aromatic ring," *J. Bacteriol.* 184(14):3975-3983 (2002).
Drake et al., "Physiology of the thermophilic acetogen *Moorella thermoacetica*," *Res. Microbiol.* 155(10):869-883 (2004).
Drake, "Acetogenesis, acetogenic bacteria, and the acetyl-CoA "Wood/Ljungdahl" pathway: past and current perspectives," In H.L. Drake (ed.), *Acetogenesis* pp. 3-60 Chapman and Hall, New York (1994).
Drake, "Demonstration of hydrogenase in extracts of the homoacetate-fermenting bacterium *Clostridium thermoaceticum*," *J. Bacteriol.* 150(2):702-709 (1982).
Drevland et al., "Enzymology and Evolution of the Pyruvate Pathway to 2-Oxobutyrate in *Methanocaldococcus jannachii*," *J. Bacteriol.* 189(12):4391-4400 (2007).
Eikmanns et al., "The phosphoenolpyruvate carboxylase gene of *Corynebacterium glutamicum*: Molecular cloning, nucleotide sequence, and expression," *Mol. Gen. Genet.* 218:330-339 (1989).

Eisen et al., "The complete genome sequence of *Chlorobium tepidum* TLS, a photosynthetic, anaerobic, green-sulfur bacterium," *Proc. Natl. Acad. Sci. U.S.A.* 99(14):9509-9514 (2002).
Ekiel et al., "Acetate and CO2 assimilation by *Methanothrix concilii*," *J. Bacteriol.* 162(3):905-908 (1985).
Enomoto et al., "Cloning and sequencing of the gene encoding the soluble fumarate reductase from *Saccharomyces cerevisiae*," *DNA Res.* 3:263-267 (1996).
Evans et al., "A new ferredoxin-dependent carbon reduction cycle in a photosynthetic bacterium," *Proc. Natl. Acad. Sci. U.S.A.* 55(4):928-934 (1966).
Fernandez-Valverde et al., "Purification of *Pseudomonas putida* Acyl Coenzyme A Ligase Active with a Range of aliphatic and Aromatic substrates," *Appl. Environ. Microbiol.* 59(4):1149-1154 (1993).
Ford et al., "Molecular properties of the lys1+ gene and the regulation of alpha-aminoadipate reductase in *Schizosaccharomyces pombe*," *Curr. Genet.* 28(2):131-137 (1995).
Fox et al., "Characterization of the region encoding the Co-induced hydrogenase of *Rhodospirillum rubrum*," *J. Bacteriol.* 178(21):6200-6208 (1996).
Fox et al., "Isolation and characterization of homogeneous acetate kinase from *Salmonella typhimurium* and *Escherichia coli*," *J. Biol. Chem.* 261(29):13487-13497 (1986).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 2:e145 (2004).
Fujinaga and Meyer "Cloning and expression in *Escherichia coli* of the gene encoding the [2Fe-2S] ferredoxin from *Clostridium pasteurianum*," *Biochem. Biophys. Res. Commun.* 192(3):1115-1122 (1993).
Fukuda et al., "Molecular cloning in *Escherichia coli*, expression, and nucleotide sequence of the gene for the ethylene-forming enzyme of *Pseudomonas syringae* pv. phaseolicola PK2," *Biochem. Biophys. Res. Commun.* 188(2):826-832 (1992).
Fukuda et al., "Role of a highly conserved YPITP motif in 2-oxoacid:ferredoxin oxidoreductase," *Eur. J. Biochem.* 268:5639-5646 (2001).
Fukuda et al., "Substrate recognition by 2-oxoacid:ferredoxin oxidoreductase from *Sulfolobus* sp. Strain 7," *Biochim. Biophys. Acta* 1597:74-80 (2002).
Furdui et al., "The role of pyruvate ferredoxin oxidoreductase in pyruvate synthesis during autotrophic growth by the Wood-Ljungdahl pathway," *J. Biol. Chem.* 275(37):28494-28499 (2000).
Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).
Germer et al., "Overexpression, isolation, and spectroscopic characterization of the bidirectional [NiFe] hydrogenase from *Synechocystis* sp. PCC 6803," *J. Biol. Chem.* 284(52):36462-36472 (2009).
Gibbs et al., "Degenerate olignucleotide gene shuffling (DOGS): a method for enhancing the frequence of recombination with family shuffling," *Gene* 271:13-20 (2001).
Gibson et al., "Physical and genetic interactions of cytosolic malate dehydrogenase with other gluconeogenic enzymes," *J. Biol. Chem.* 278:25628-25636 (2003).
Giesel and Simon, "On the occurrence of enoate reductase and 2-oxocarboxylate reductase in *Clostridia* and some observations on the amino acid fermentation by *Peptostreptococcus anaerobius*," *Arch. Microbiol.* 135(1):51-57 (1983).
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
Gonzalez et al., "Genetic analysis of *Carboxydothermus hydrogenoformans* carbon monoxide dehydrogenase genes cooF and cooS," *FEMS Microbiol. Lett.* 191(2):243-247 (2000).
Guest et al., "The fumarase genes of *Escherichia coli*: location of the fumB gene and discovery of a new gene (fumC)," *J. Gen. Microbiol.* 131(11):2971-2984 (1985).

(56) References Cited

OTHER PUBLICATIONS

Gulick et al., "The 1.75 A crystal structure of acetyl-CoA synthetase bound to adenosine-5'-propylphosphate and coenzyme A," *Biochemistry* 42(10):2866-2873 (2003).
Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from *Schizosaccharomyces pombe*," *Yeast* 21(15):1279-1288 (2004).
Guo et al., "Site-directed mutational analysis of the novel catalytic domains of alpha-aminoadipate reductase (Lys2p) from *Candida albicans*," *Mol. Genet. Genomics* 269(2):271-279 (2003).
Haller et al., "Discovering new enzymes and metabolic pathways: conversion of succinate to propionate by *Escherichia coli*," *Biochemistry* 39(16):4622-4629 (2000).
Hanai et al., "Engineered synthetic pathway for isopropanol production in *Escherichia coli*," *Appl. Environ. Microbiol.* 73:7814-7818 (2007).
Hara et al., "The 4-oxalomesaconate hydratase gene, involved in the protocatechuate 4,5-cleavage pathway, is essential to vanillate and syringate degradation in *Sphingomonas paucimobilis* SYK-6," *J. Bacteriol.* 182(24):6950-6957 (2000).
Hartmanis, M.G., "Butyrate kinase from*Clostridium acetobutylicum*," *J. Biol. Chem.* 262(2):617-621 (1987).
Haselbeck et al., "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).
Hayes et al., "Combining computational and experimental screening for rapid optimization of protein properties," *Proc. Natl. Acad. Sci. U.S.A.* 99(25):15926-15931 (2002).
Herrmann, "Energy Conservation via Electron-Transferring Flavoprotein in Anaerobic Bacteria," *J. Bacteriol.* 190(3):784-791 (2008).
Hesslinger et al., "Novel keto acid formate-lyase and propionate kinase enzymes are components of an anaerobic pathway in *Escherichia coli* that degrades L-threonine to propionate," *Mol. Microbiol.* 27:477-492 (1998).
Hibbert et al., "Directed evolution of biocatalytic processes," *Biomol. Eng.* 22:11-19 (2005).
Hijarrubia et al., "Domain Structure characterization of the Multifunctional α-Aminoadipate Reductase from *Penicillium chrysogenum* by Limited Proteolysis," *J. Biol. Chem.* 278:8250-8256 (2003).
Hoffmeister et al., "Mitochondrial trans-2-enoyl-CoA reductase of wax ester fermentation from *Euglena gracilis* defines a new family of enzymes involved in lipid synthesis," *J. Biol. Chem.* 280(6):4329-4338 (2005).
Horswill et al., "In vitro conversion of propionate to pyruvate by *Salmonella enterica* enzymes: 2-methylcitrate dehydratase (PrpD) and aconitas Enzymes catalyze the conversion of 2-methylcitrate to 2-methylisocitrate," *Biochemistry* 40(15):4703-4713 (2001).
Huang et al., "Genetic characterization of the resorcinol catabolic pathway in *Corynebacterium glutamicum*," *Appl. Environ. Microbiol.* 72:7238-7245 (2006).
Hugler et al., "Evidence for autotrophic CO2 fixation via the reductive tricarboxylic acid cycle by members of the epsilon subdivision of proteobacteria," *J. Bacteriol.* 187(9):3020-3027 (2005).
Hugler et al., Hugler et al., "Autotrophic CO2 fixation via the reductive tricarboxylic acid cycle in different lineages within the phylum Aquificae: evidence for two ways of citrate cleavage," *Environ. Microbiol.* 9(1):81-92 (2007).
Huisman and Lalonde, "Enzyme evolution for chemical process applications," In R.N. Patel (ed.), *Biocatalysis in the pharmaceutical and biotechnology industries*, CRC Press, p. 717-742 (2007).
Hynes et al., "ATP-citrate lyase is required for production of cytosolic acetyl coenzyme A and development in *Aspergillus nidulans*," *Eukaryot. Cell* 9(7):1039-1048 (2010).

Ikeda et al., "Anabolic five subunit-type pyruvate:ferredoxin oxidoreductase from *Hydrogenobacter thermophilus* TK-6 ," *Biochem. Biophys. Res. Commun.* 340(1):76-82 (2006).
Ingram-Smith et al., "AMP-forming acetyl-CoA synthetases in Archaea show unexpected diversity in substrate utilization," *Archaea.* 2(2):95-107 (2007).
Ingram-Smith et al., "Characterization of the acetate binding pocket in the *Methanosarcina thermophila* acetate kinase," *J. Bacteriol.* 187(7):2386-2394 (2005).
Iverson et al., "Structure of the *Escherichia coli* fumarate reductase respiratory complex," *Science* 284(5422):1961-1966 (1999).
Iwakura et al., "Studies on regulatory functions of malic enzymes. VI. Purification and molecular properties of NADP-linked malic enzyme from *Escherichia coli* W," *J. Biochem.* 85:1355-1365 (1979).
Izumi et al., "Structure and Mechanism of HpcG, a Hydratase in the Homoprotocatechuate Degradation Pathway of *Escherichia coli*," *J. Mol. Biol.* 370:899-911 (2007).
Jacobi et al., "The hyp operon gene products are required for the maturation of catalytically active hydrogenase isoenzymes in *Escherichia coli*," *Arch. Microbiol.* 158(6):444-451 (1992).
Jogl et al., Crystal structure of yeast acetyl-coenzyme A synthetase in complex with AMP, *Biochemistry* 43(6):1425-1431 (2004).
Jojima et al., "Production of isopropanol by metabolically engineered *Escherichia coli*," *Appl. Microbiol. Biotechnol.* 77:1219-1224 (2008).
Kai et al., "Phosphoenolpyruvate carboxylase: three-dimensional structure and molecular mechanisms," *Arch. Biochem. Biophys.* 414:170-179 (2003).
Kanao et al., "Kinetic and biochemical analyses on the reaction mechanism of a bacterial ATP-citrate lyase," *Eur. J. Biochem.* 269(14):3409-3416 (2002).
Kasberg et al., "Cloning, characterization, and sequence analysis of the c1cE gene encoding the maleylacetate reductase of *Pseufomonas* sp. Strain B13," *J. Bacteriol.* 179:3801-3803 (1997).
Kaschabek and Reineke, "Maleylacetate reductase of *Pseufomonas* sp. Strain B13: specificity of substrate conversion and halide elimination," *J. Bacteriol.* 177:320-325 (1995).
Kaschabek and Reineke, "Degradation of chloroaromatics: purification and characterization of maleylacetate reductase from *Pseudomonas* sp. Strain B13," *J. Bacteriol.* 175:6075-6081 (1993).
Kato and Asano, "3-Methylaspartate ammonia-lyase as a marker enzyme of the mesaconate pathway for (S)-glutamate fermentation in *Enterobacteriaceae*," *Arch. Microbiol.* 168(6):457-463 (1997).
Kellum et al., "Effects of cultivation gas phase on hydrogenase of the acetogen *Clostridium thermoaceticum*," *J. Bacteriol.* 160(1):466-469 (1984).
Kim et al., "Both subunits of ATP-citrate lyase from *Chlorobium tepidum* contribute to catalytic activity," *J. Bacteriol.* 188(18):6544-6552 (2006).
Kim et al., "Construction of an *Escherichia coli* K-12 Mutant for Homoethanologenic Fermentation of glucose or Xylose without Foreign Genes," *Appl. Environ. Microbiol.* 73:1766-1771 (2007).
Kim et al., "Dihydrolipoamide Dehydrogenase Mutation Alters the NADH Sensitivity of Pyruvate Dehydrogenase Complex of *Escherichi coli* K-12," *J. Bacteriol.* 190:3851-3858 (2008).
Kim et al., "Effect of overexpression of *Actinobacillus succinogenes* phosphoenolpyruvate carboxykinase on succinate production in *Escherichia coli*," *Appl. Environ. Microbiol.* 70:1238-1241 (2004).
Knappe et al., "A radical-chemical route to acetyl-CoA: the anaerobically induced pyruvate formate-lyase system of *Escherichia coli*," *FEMS Microbiol. Rev.* 75:383-398 (1990).
Kobayashi et al., "Physicochemical, catalytic, and immunochemical properties of fumarases crystallized separately from mitochondrial and cytosolic fractions of rat liver," *J. Biochem.* 89(6):1923-1931 (1981).
Koland et al., "Proximity of Reactive Cysteine Residue and Flavin in *Escherichia coli* Pyruvate Oxidase As Estimated by Flourescence Energy Transfer," *Biochemistry* 21:4438-4442 (1982).
Kosaka et al., "Characterization of the sol operon in butanol-hyperproducing *Clostridium saccharoperbutylacetonicum* strain N1-4 and its degeneration mechanism," *Biosci. Biotechnol. Biochem.* 71:58-68 (2007).

(56) References Cited

OTHER PUBLICATIONS

Kretz et al., "Gene site saturation mutagenesis: a comprehensive mutagenesis approach," *Methods Enzymol.* 388:3-11 (2004).
Kumari et al., "Cloning, Characterization, and Functional Expression of acs, the Gene Which Encodes Acetyl Coenzyme A Synthetase in *Escherichia coli*," *J. Bacteriol.* 177(10):2878-2886 (1995).
Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.* 16(9): 1448-1452 (2006).
Laivenieks et al., "Cloning sequencing, and overexpression of the *Anaerobiospirillum succiniproducens* phosphoenolpyruvate carboxykinase (pckA) gene," *Appl. Environ. Microbiol.* 63:2273-2280 (1997).
Lee et al., "A new approach to directed gene evolution by recombined extension on truncated templates (RETT)," *J. Molec. Catalysis* 26:119-129 (2003).
Lee et al., "Cloning and Characterization of *Mannheimia succiniciproducens* MBEL55E Phosphoenolpyruvate Carboxykinase (pckA) Gene," *Biotechnol. Bioprocess Eng.* 7:95-99 (2002).
Leutwein et al., "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).
Lin et al., "Fed-batch culture of a metabolically engineered *Escherichia coli* strain designed for high-level succinate production and yield under aerobic conditions," *Biotechnol. Bioeng.* 90:775-779 (2005).
Louis et al., "Restricted distribution of the butyrate kinase pathway among butyrate-producing bacteria from the human colon," *J. Bacteriol.* 186:2099-2106 (2004).
Low et al., "Mimicking somatic hypermutation: Affinity maturation of antibodies displayed on bacteriophage using a bacterial mutator strain," *J. Mol. Biol.* 260(3):359-368 (1996).
Lutz et al., "Creating multiple-crossover DNA libraries independent of sequence identity," *Proc. Natl. Acad. Sci. U.S.A.* 98:11248-11253 (2001).
Lutz et al., "Rapid generation of incremental truncation libraries for protein enginering using α-phosphothioate nucleotides," *Nucleic Acids Res.* 29:E16 (2001).
Maeda et al., "*Escherichia coli* hydrogenase 3 is a reversible enzyme possessing hydrogen uptake and synthesis activities," *Appl. Microbiol. Biotechnol.* 76(5):1035-1042 (2007).
Mahlert et al., "Stereospecific enzymatic transformation of alpha-ketoglutarate to (2S,3R)-3-methyl glutamate during acidic lipopeptide biosynthesis," *J. Am. Chem. Soc.* 129(39):12011-12018 (2007). (Epub Sep. 5, 2007).
Marolewski et al., "Cloning and characterization of a new purine biosynthetic enzyme: a non-folate glycinamide ribonucleotide transformylase from *E. coli*," *Biochemistry* 33(9):2531-2537 (1994).
Maruyama et al., "Cloning, sequencing, and expression of the gene encoding 4-hydroxy-4-methyl-2-oxoglutarate aldolase from *Pseudomonas ochraceae* NGJ1," *Biosci. Biotechnol. Biochem.* 65(12):2701-2709 (2001).
McAlister-Henn et al., "Isolation and expression of the gene encoding yeast mitochondrial malate dehydrogenase," *J. Bacteriol.* 169:5157-5166 (1987).
Meijer et al., "Gene deletion of cytosolic ATP: citrate lyase leads to altered organic acid production in *Aspergillus niger*," *J. Ind. Microbiol. Biotechnol.* 36(10):1275-1280 (2009).
Melchiorsen et al., "The level of pyruvate-formate lyase controls the shift from homolactic to mixed-acid product formation in *Lactoccus lactis*," *Appl. Microbiol. Biotechnol.* 58(3):338-344 (2002).
Menon et al., "Mechanism of the *Clostridium thermoaceticum* pyruvate:ferredoxin oxidoreductase: evidence for the common catalytic intermediacy of the hydroxyethylthiamine pyropyrosphate radical," *Biochemistry* 36(28):8484-8494 (1997).
Minard et al., "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).
Mizobata et al., "Purification and characterization of a thermostable class II fumarase from *Thermus thermophilus*," *Arch. Biochem. Biophys.* 355(1):49-55 (1998).
Morris et al., "Nucleotide sequence of the LYS2 gene of *Saccharomyces cerevisiae*: homology to *Bacillus brevis* tyrocidine synthetase1," *Gene* 98:141-145 (1991).
Mukhopadhyay et al., "Pyruvate carboxylase from *Mycobacterium smegmatis*: stabilization, rapid purification, moleculare and biochemical characterization and regulation of the cellular level," *Biochim. Biophys. Acta* 1475(3):191-206 (2000).
Muller et al., "Nucleotide exchange and excisiion technology (NExT) DNA shuffling; a robust method for DNA fragmentation and directed evolution," *Nucleic Acids Res.* 33:e117 (2005).
Muratsubaki and Enomoto, "One of the fumarate reductase isoenzymes from *Saccharomyces cerevisiae* is encoded by the OSM1 gene," *Arch. Biochem. Biophys.* 352:175-181 (1998).
Musfeldt et al., "Novel type of ADP-forming acetyl Coenzyme A synthetase in hyperthermophilic archaea: heterologous expression and characterization of isoenzymes from the sulfate reducer *Archaeoglobus fulgidus* and the methanogen *Methanococcus jannaschii*," *J. Bacteriol.* 184(3):636-644 (2002).
Nakano et al., "Characterization of Anaerobic Fermentative Growth of *Bacillus subtilis*: Identification of Fermentation End Products and Genes Required for Growth," *J. Bacteriol.* 179(21):6749-6755 (1997).
Ness et al., "Synthetic shuffling expands functional protein diversity by allowing amino acids to recombine independently," *Nat. Biotechnol.* 20:1251-1255 (2002).
Nilekani et al., "Purification and properties of citrate lyase from *Escherichia coli*," *Biochemistry* 22(20):4657-4663 (1983).
Nimmo, "Kinetic mechanism of *Escherichia coli* isocitrate dehydrogenase and its inhibition by glyoxylate and oxaloacetate," *Biochem. J.* 234(2):317-323 (1986).
Nishizawa et al., "Gene expression and characterization of two 2-oxoacid:ferredoxin oxidoreductases from *Aeropyrum pernix* K1," *FEBS. Lett.* 579:2319-2322 (2005).
Nowrousian et al., "The fungal acl1 and acl2 genes encode two polypeptides with homology to the N- and C-terminal parts of the animal ATP citrate lyase polypeptide," *Curr.Genet.* 37(3):189-193 (2000).
O'Brien et al., "Regulation by Lipids of Cofactor Binding to a Peripheral Membrane Enzyme: Binding of Thiamin Pyrophosphate to Pyruvate Oxidase," *Biochemistry* 16(14):3105-3109 (1977).
Obrien et al., "Studies of the Thiamin Pyrophosphate Binding Site of *Escherichia coli* Pyruvate Oxidase," *J. Biol. Chem.* 255(8):3302-3307 (1980).
Ostermeier et al., "A Combinatorial approach to hybrid enzymes independent of DNA homology," *Nat. Biotechnol.* 17:1205-1209 (1999).
Ostermeier et al., "Combinatorial protein engineering by incremental truncation," *Proc. Natl. Acad. Sci. U.S.A.* 96:3562-3567 (1999).
Otten and Quax, "Directed evolution:selecting today's biocatalysts," *Biomol. Eng.* 22:1-9 (2005).
Parkin et al., "Rapid and efficient electrocatalytic CO2/CO interconversions by *Carboxydothermus hydrogenoformans* CO dehydrogenase I on an electrode," *J. Am. Chem. Soc.* 129(34):10328-10329 (2007).
Pieulle et al., "Isolation and analysis of the gene encoding the pyruvate-ferredoxin oxidoreductase of *Desulfovibrio africanus*, production of the recombinant enzyme in *Escherichia coli*, and effect of carboxy-terminal deletions on its stability," *J. Bacteriol.* 179(18):5684-5692 (1997).
Priefert et al., "Identification and molecular characterization of the acetyl coenzyme A synthetase gene (acoE) of *Alcaligenes eutrophus*," *J. Bacteriol.* 174(20):6590-6599 (1992).
Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).
Pritchard et al., "A general model of error-prone PCR," *J. Theor. Biol.* 234:497-509 (2005).

(56) References Cited

OTHER PUBLICATIONS

Providenti et al., "*Comamonas testosteroni* BR6020 possesses a single genetic locus for extradiol cleavage of protocatechuate," *Microbiology* 147(Pt 8):2157-2167 (2001).
Rado et al., "Phosphotransacetylase from *Bacillus subtilis*: purification and physiological studies," *Biochim. Biophys. Acta* 321:114-125 (1973).
Ragsdale, "Enzymology of the wood-Ljungdahl pathway of acetogenesis," *Ann. NY Acad. Sci.* 1125:129-136 (2008).
Ragsdale, "Pyruvate ferredoxin oxidoreductase and its radical intermediate," *Chem. Rev.* 103(6):2333-2346 (2003).
Rajpal et al., "A general method for greatly improving the affinity of antibodies by using combinatorial libraries," *Proc. Natl. Acad. Sci. U.S.A.* 102:8466-8471 (2005).
Rakhely, "Cyanobacterial-type, heteropentameric, NAD+-reducing NiFe hydrogenase in the purple sulfur photosynthetic bacterium *Thiocapsa roseopersicina*," *Appl. Environ. Microbiol.* 70(2):722-728 (2004).
Rangarajan et al., "Structure of [NiFe] hydrogenase maturation protein HypE from *Escherichia coli* and its interaction with HypF," *J. Bacteriol.* 190(4):1447-1458 (2008).
Reetz and Carballeira, "Iterative saturation mutagenesis (ISM) for rapid directed evolution of functional enzymes," *Nat. Protoc.* 2:891-903 (2007).
Reetz et al., "Directed Evolution of an Enantioselective Enzyme through Combinatorial Multiple-Cassette Mutagenesis," *Angew. Chem. Int. Ed. Engl.* 40:3589-3591 (2001).
Reetz et al., "Iterative saturation mutagenesis on the basis of B factors as a strategy for incresing protein thermostability," *Angew. Chem. Int. Ed.* 45:7745-7751 (2006).
Regev-Rudzki et al., "Yeast Aconitase in Two Locations and Two Metabolic Pathways: Seeing Small Amounts Is Believing," *Mol. Biol. Cell* 16:4163-4171 (2005).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Rohdich et al., "Enoate reductases of *Clostridia*. Cloning, sequencing, and expression," *J. Biol. Chem.* 276(8):5779-5787 (2001).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Sass et al., "Folding of fumarase during mitochondrial import determines its dual targeting in yeast," *J. Biol. Chem.* 278(46):45109-45116 (2003).
Sawers et al., "Characterization and physiological roles of membrane-bound hydrogenase isoenzymes from *Salmonella typhimurium*," *J. Bacteriol.* 168(1):398-404 (1986).
Sawers et al., "Differential expression of hydrogenase isoenzymes in *Escherichia coli* K-12: evidence for a third isoenzyme," *J. Bacteriol.* 164(3):1324-1331 (1985).
Sawers et al., "Purification and properties of membrane-bound hydrogenase isoenzyme 1 from anaerobically grown *Escherichia coli* K12," *Eur. J. Biochem.* 156(2):265-275 (1986).
Sawers, G., "The hydrogenases and formate dehydrogenases of *Escherichia coli*," *Antonie Van Leeuwenhoek* 66(1-3):57-88 (1994).
Schink et al., "The membrane-bound hydrogenase of *Alcaligenes eutrophus*. I. Solubilization, purification, and biochemical properties," *Biochim. Biophys. Acta.* 567(2):315-324 (1979).
Schneider et al., "Biosynthesis of the prosthetic group of citrate lyase," *Biochemistry* 39(31):9438-9450 (2000).
Schneider et al., "Purification and properties of soluble hydrogenase from *Alcaligenes eutrophus* H 16," *Biochim. Biophys. Acta.* 452(1):66-80 (1976).
Seedorf et al., "The genome of *Clostridium kluyveri*, a strict anaerobe with unique metabolic features," *Proc. Natl. Acad. Sci. U.S.A.* 105(6):2128-2133 (2008).
Seibert et al., "Characterization of a gene cluster encoding the maleylacetate reductase from *Ralstonia eutropha* 335T, and enzyme recruited for growth with 4-fluorobenzoate," *Microbiology* 150:463-472 (2004).
Seibert et al., "Purification and characterization of maleylacetate reductase from *Alcaligenes eutrophys* JMP134(pJP4)," *J. Bacteriol.* 175:6745-6754 (1993).
Selifonova et al., "Rapid evolution of novel traits in microorganisms," *Appl. Environ. Microbiol.* 67:3645-3649 (2001).
Sen et al., "Developments in directed evolution for improving enzyme functions," *Appl. Biochem. Biotechnol.* 143:212-223 (2007).
Seravalli et al., "Evidence that NiNi acetyl-CoA synthase is active and that the CuNi enzyme is not," *Biochemistry* 43(13):3944-3955 (2004).
Shao et al., "Random-priming in vitro recombination: an effective tool for directed evolution," *Nucleic Acids Res.* 26:681-683 (1998).
Shimoyama et al., "MmcBC in Pelotomaculum thermopropionicum represents a novel group of prokaryotic fumarases," *FEMS Microbiol Lett.* 270(2):207-213 (2007).
Sieber et al., "Libraries of hybrid proteins from distantly related sequences," *Nat. Biotechnol.* 19:456-460 (2001).
Siebers et al., "Reconstruction of the central carbohydrate metabolism of *Thermoproteus tenax* by use of genomic and biochemical data," *J. Bacteriol.* 186(7):2179-2194 (2004).
Smith et al., "Fumarate metabolism and the microaerophily of *Campylobacter* species," *Int. J. Biochem. Cell Biol.* 31(9):961-975 (1999).
Sohling et al., "Molecular analysis of the anaerobic succinate degradation pathway in *Clostridium kluyveri*.," *J. Bacteriol.* 178(3):871-880 (1996).
St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and *Campylobacter jejuni*," *J. Bacteriol.* 189:4764-4773 (2007).
Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiology* 151(Pt 11):3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.* 280(28):26200-26205 (2005). (Epub May 17, 2005).
Steffan et al., "Isolation and characterization of the yeast gene encoding the MDH3 isozyme of malate dehydrogenase," *J. Biol. Chem.* 267:24708-24715 (1992).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stols et al., "Expression of *Ascaris suum* malic enzyme in a mutant *Escherichia coli* allows production of succinic acid from glucose," *Appl. Biochem. Biotechnol.* 63-65: 153-158 (1997).
Stols et al., "Production of succinic acid through overexpression of NAD(+)-dependent malic enzyme in an *Escherichia coli* mutant," *Appl. Environ. Microbiol.* 63(7):2695-2701 (1997).
Suzuki et al., "GriC and GriD Constitute a carboxylic acid reductase involved in grixazone biosynthesis in *Streptomyces griseus*," *J. Antibiot.* 60(6):380-387 (2007).
Suzuki, "Phosphotransacetylase of *Escherichia coli* B, activation by pyruvate and inhibition by NADH and certain nucleotides," *Biochim. Biophys. Acta* 191(3):559-569 (1969).
Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).
Takahashi-Abbe et al., "Biochemical and functional properties of a pyruvate formate-lyase (PFL)-activating system in *Streptococcus mutans*," *Oral Microbiol. Immunol.* 18(5)293-297 (2003).

(56) References Cited

OTHER PUBLICATIONS

Takeo, "Existence and Properties of Two Malic Enzymes in *Escherichia coli* Especially of NAD-linked Enzyme," *J. Biochem.* 66:379-387 (1969).

Tao et al., "Expression of ethylene-forming enzyme (EFE) of *Pseudomonas syringae* pv. glycinea in *Trichoderma viride*," *Appl. Microbiol. Biotechnol.* 80(4):573-578 (2008). (Epub Jun. 25, 2008).

Tseng et al., "Oxygen- and growth rate-dependent regulation of *Escherichia coli* fumarase (FumA, FumB, and BumC) activity," *J. Bacteriol.* 183(2):461-467 (2001).

Valdes-Hevia et al., "Isolation and characterization of the gene encoding phosphoenolpyruvate carboxykinase from *Saccharomyces cerevisiae*," *FEBS Lett.* 258(2):313-316 (1989).

Vazquez et al., "Phosphtransbutyrylase expression in *Bacillus megaterium*," *Curr. Microbiol.* 42:345-349 (2001).

Venkitasubramanian et al. *Biocatalysis in the Pharmaceutical and Biotechnology Industries*, ed. R.N. Patel, Chapter 15, pp. 425-440, CRC Press LLC, Boca Raton, Fl. 2007.

Venkitasubramanian et al., "Reduction of Carboxylic Acids by Nocardia Aldehyde Oxidoreductase Requires a Phosphopantetheinylated Enzyme," *J. Biol Chem.* 282(1):478-485 (2007).

Vey et al., "Structural basis for glycyl radical formation by pyruvate formate-lyase activating enzyme," *Proc. Natl. Acad. Sci. U.S.A.* 105:16137-16141 (2008).

Vita et al., "Disulfide bond-dependent mechanism of protection against oxidative stress in pyruvate-ferredoxin oxidoreductase of anaerobic *Desulfovibrio* bacteria," *Biochemistry* 47(3):957-964 (2008).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27:e18 (1999).

Walker et al., "Yeast pyruvate carboxylase: identification of two genes encoding isoenzymes," *Biochem. Biophys. Res. Commun.* 176:1210-1217 (1991).

Walter et al., "Sequence and arrangement of two genes of the butyrate-synthesis pathway of *Clostridium acetobutylicum* ATCC 824," *Gene* 134(1):107-111 (1993).

Weidner et al., "Molecular Characterization of the Genes Encoding Pyruvate Formate-Lyase and Its Activating Enzyme of *Clostridium pasteruianum*," *J. Bacteriol.* 178(8):2440-2444 (1996).

Weingart et al., "Comparison of Ethylene Production by *Pseudomonas syringae* and *Ralstonia solanacearum*," *Phytopathology* 89(5):360-365 (1999).

Wiesenborn et al., "Phosphotransbutyrylase from *Clostridium acetobutylicum* ATCC 824 and its role in acidogenesis," *Appl. Environ. Microbiol.* 55:317-322 (1989).

Winzer et al., "Acetate kinase from *Clostridium acetobutylicum*: a highly specific enzyme that is actively transcribed during acidogenesis and solventogenesis," *Microbiology* 143 ( Pt 10):3279-3286 (1997).

Wong et al., "Sequence saturation mutagenesis (SeSaM): a novel method for directed evolution," *Nucleic Acids Res.* 32:e26 (2004).

Wong et al., "Sequence saturation mutagenesis with tunable mutation frequencies," *Anal. Biochem.* 341:187-189 (2005).

Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).

Wood et al., "A challenge for 21st century molecular biology and biochemistry: what are the causes of obligate autotrophy and methanotrophy?," *FEMS Microbiol. Rev.* 28(3):335-352 (2004).

Woods, "Two biochemically distinct classes of fumarase in *Escherichia coli*," *Biochim. Biophys. Acta* 954(1):14-26 (1988).

Wu et al., "Life in hot carbon monoxide: the complete genome sequence of *Carboxydothermus hydrogenoformans* Z-2901," *PLoS Genet.* 1(5):e65 (2005).

Yakunin and Hallenbeck, "Purification and characterization of pyruvate oxidoreductase from the photosynthetic bacterium *Rhodobacter capsulatus*," *Biochim. Biophys. Acta.* 1409(1):39-49 (1998).

Yamomoto et al., "Carboxylation reaction catalyzed by 2-oxoglutarate:ferredoxin oxidoreductases from *Hydrogenobacter thermophilus*," *Extremophiles* 14:79-85 (2010).

Yun et al., "The genes for anabolic 2-oxoglutarate: ferredoxin oxidoreductse from *Hydrogenobacter thermophilus* TK-6," *Biochem. Biophys. Res. Commun.* 282(2):589-594 (2001).

Zhao et al., "Molecular evolution by staggered extension process (StEP) in vitro recombination," *Nat. Biotechnol.* 16:258-261 (1998).

Zhou et al., "Engineering a native homoethanol pathway in *Escherichia coli* B for ethanol production," *Biotechnol. Lett.* 30:335-342 (2008).

\* cited by examiner

```
ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCTTGCCG
ACGCGGGCAGCTTGGTGATCGTCGAAACGCTCGATGCCGTGCGTGCCGGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGACATCGGCTTGGTACGTCCCACCGAGATCTTCT
TCGTCCCGCGCGTGTGCGACATGGTCTTCCAGCGCTATCAGAGCGAGCTGGACCGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCGCTGGCCGCGGAGATGAAGACGTTCA
TGGAGTCCGTCCTCGATCTGCCACTGCACGACGGGTACGGGTCGACCGAGGCGGGCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCGATCTCGCGACAGGC
CAGGCCGATGAGCTGCTCGCCCTGCGCCGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCGGTGGGTGTCGTCGTCAGCCCGGCGAACGAGCTGCGCGATCTGGCGAATTACA
TTGAGGCGGAACGCAACTCGGGCGCGAAGCGTCCCACCTTCACCTCGGTGCACGGCGGCGGTTC
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCGGTTCCTGTGCCTGGAATGGCTGGAGCGGCTGGACAAGACGGGTGGCACGCTGATCTG
CGTCGTGCGCGGTAGTGACGCGGCCGCGGCCCGTAAACGGCTGGACTCGGCGTTCGACAGCGGC
GATCCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCCTACACCCAGCTGTTCGGCCCC
```

FIGURE 10A

```
AATGTCGTCGGCACCGCCGAAATCGTCCGGTTGGCGATCACGGCGCGCGGCGCAAGCCGGTCACCT
ACCTGTCGACCGTCGGAGTGGCCGACCAGGTCGACCCGGCGGAGTATCAGGAGGACAGCGACGT
CCGCGAGATGAGCGCGGTGCGCGTCGTGCGCGAGAGTTACGCCAACGGCTACGGCAACAGCAAG
TGGGCGGGGGAGGTCCTGCTGCGCGAAGCACACGATCTGTGTGGCTTGCCGGTCGCGGTGTTCC
GTTCGGACATGATCCTGGCGCACAGCCGGTACGCGGGTCAGCTCAACGTCCAGGACGTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCGGACTTCACGGCGGCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTTCGAGACGGCGATCCGCGCGCTGCCGGAAAAGCAAC
GCCAGGCCTCGGTGCTGCCGTTGCTGGACGCCTACCGCAACCCCTGCCCGGCGGTCCGCGGCGC
GATACTCCCGGCCAAGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTAA
```

FIGURE 10A CONT.

```
mavdspderlqrriaqlfaedeqvkaarpleavsaavsapgmrlaqiaatvmagyadrpaaggr
afelntddatgrtslrllprfetityrelwqrvgevaaawhhdpenplragdfvallgftsidy
atldladihlgavtvplqasaavsqliailtetsprllastpehldaaveellagttperlvvf
dyhpedddqraafesarrrladagslvivetldavrargrdlpaaplfvpdtdddplalliyts
gstgtpkgamytnrlaatmwqgnsmlqgnsqrvginlnympmshiagrislfgvlarggtayfa
aksdmstlfediglvrpteiffvprvcdmvfqryqseldrrsvagadldtldrevkadlrqnyl
ggrflvavvgsaplaaemktfmesvldlplhdgygsteagasvlldnqiqrppvldyklvdvpe
lgyfrtdrphprgelllkaettipgyykrpevtaeifdedgfyktgdivaelehdrlvyvdrrn
nvlklsqgefvtvahleavfasssplirqifiygssersyllavivptddalrgrdtatlksala
esiqriakdanlqpyeiprdflietepftiangllsgiakllrpnlkerygaqleqmytdlatg
qadellalrreaadlpvletvsraakamlgvasadmrpdahftdlggdslsalsfsnllheifg
vevpvgvvvspanelrdlanyieaernsgakrptftsvhgggseiraadltldkfidartlaaa
dsiphapvpaqtvlltgangylgrflclewlerldktggtlicvvrgsdaaaarkrldsafdsg
dpgllehyqqlaartlevlagdigdpnlgldatwqrlaetvdlivhpaalvnhvlpytqlfgp
nvvgtaeivrlaitarrkpvtylstvgvadqvdpaeyqedsdvremsavrvvresyangygnsk
wagevllreahdlcglpvavfrsdmilahsryagqlnvqdvftrlilslvatgiapysfyrtda
dgnrqrahydglpadftaaaitalgiqategfrtydvlnpyddgisldefvdwlvesghpiqri
tdysdwfhrfetairalpekqrqasvlplldayrnpcpavrgailpakefqaavqtakigpeqd
iphlsaplidkyvsdlellqll*
```

ATGATTGAAACCATTCTGCCTGCAGGCGTTGAAAGCGCAGAACTGCTGGAATATCCGGAAGATC
TGAAAGCACATCCGGCAGAAGAACATCTGATTGCCAAAAGCGTTGAAAAACGTCGTCGTGATTT
TATTGGTGCACGTCATTGTGCACGTCTGGCACTGGCAGAACTGGGTGAACCTCCGGTTGCAATT
GGTAAAGGTGAACGTGGTGCACCGATTTGGCCTCGTGGTGTTGTTGGTAGCCTGACCCATTGTG
ATGGTTATCGTGCAGCAGCAGTTGCACATAAAATGCGCTTTCGCAGCATTGGTATTGATGCAGA
ACCGCATGCAACCCTGCCGGAAGGTGTTCTGGATAGCGTTAGCCTGCCGCCGGAACGTGAATGG
CTGAAAACCACCGATAGCGCACTGCATCTGGATCGTCTGCTGTTTTGTGCAAAAGAAGCCACCT
ATAAAGCCTGGTGGCCGCTGACAGCACGTTGGCTGGGTTTTGAAGAAGCCCATATTACCTTTGA
AATTGAAGATGGTAGCGCAGATAGCGGTAATGGCACCTTTCATAGCGAACTGCTGGTTCCGGGT
CAGACCAATGATGGTGGTACACCGCTGCTGAGCTTTGATGGTCGTTGGCTGATTGCAGATGGTT
TTATTCTGACCGCAATTGCCTATGCCTAA

FIGURE 11B mietilpagvesaelleypedlkahpaeehliaksvekrrrdfigarhcarlalaelgeppvai
gkgergapiwprgvvgslthcdgyraaavahkmrfrsigidaephatlpegvldsvslpperew
lkttdsalhldrllfcakeatykawwpltarwlgfeeahitfeiedgsadsgngtfhsellvpg
qtndggtpllsfdgrwliadgfiltaiaya*

```
atgaccagcgatgttcacgacgccacagacggcgtcaccgaaaccgcactcgacgacgagcagtcgacccgccgcat
cgccgagctgtacgccaccgatcccgagttcgccgccgccgcaccgttgcccgccgtggtcgacgcggcgcacaaac
ccgggctgcggctggcagagatcctgcagaccctgttcaccggctacggtgaccgcccggcgctgggataccgcgcc
cgtgaactggccaccgacgagggcgggcgcaccgtgacgcgtctgctgccgcggttcgacaccctcacctacgccca
ggtgtggtcgcgcgtgcaagcggtcgccgcggccctgcgccacaacttcgcgcagccgatctaccccggcgacgccg
tcgcgacgatcggtttcgcgagtcccgattacctgacgctggatctcgtatgcgcctacctgggcctcgtgagtgtt
ccgctgcagcacaacgcaccggtcagccggctcgcccgatcctggccgaggtcgaaccgcggatcctcaccgtgag
cgccgaatacctcgacctcgcagtcgaatccgtgcgggacgtcaactcggtgtcgcagctcgtggtgttcgaccatc
accccgaggtcgacgaccaccgcgacgcactggcccgcgcgcgtgaacaactcgccggcaagggcatcgccgtcacc
accctggacgcgatcgccgacgagggcgccgggctgccggccgaaccgatctacaccgccgaccatgatcagcgcct
cgcgatgatcctgtacacctcgggttccaccggcgcacccaagggtgcgatgtacaccgaggcgatggtggcgcggc
tgtggaccatgtcgttcatcacgggtgaccccacgccggtcatcaacgtcaacttcatgccgctcaaccacctgggc
gggcgcatccccatttccaccgccgtgcagaacggtggaaccagttacttcgtaccggaatccgacatgtccacgct
gttcgaggatctcgcgctggtgcgcccgaccgaactcggcctggttccgcgcgtcgccgacatgctctaccagcacc
acctcgccaccgtcgaccgcctggtcacgcagggcgccgacgaactgaccgccgagaagcaggccggtgccgaactg
cgtgagcaggtgctcggcggacgcgtgatcaccggattcgtcagcaccgcaccgctggccgcggagatgagggcgtt
cctcgacatcaccctgggcgcacacatcgtcgacggctacgggctcaccgagaccggcgccgtgacacgcgacggtg
tgatcgtgcggccaccggtgatcgactacaagctgatcgacgttcccgaactcggctacttcagcaccgacaagccc
taccccgcgtggcgaactgctggtcaggtcgcaaacgctgactcccgggtactacaagcgcccgaggtcaccgcgag
cgtcttcgaccgggacggctactaccacaccggcgacgtcatggccgagaccgcacccgaccacctggtgtacgtgg
accgtcgcaacaacgtcctcaaactcgcgcagggcgagttcgtggcggtcgccaacctggaggcggtgttctccggc
gcggcgctggtgcgccagatcttcgtgtacggcaacagcgagcgcagtttccttctggccgtggtggtcccgacgcc
ggaggcgctcgagcagtacgatccggccgcgctcaaggccgcgctggccgactcgctgcagcgcaccgcacgcgacg
ccgaactgcaatcctacgaggtgccggccgatttcatcgtcgagaccgagccgttcagcgccgccaacgggctgctg
tcgggtgtcggaaaactgctgcggcccaacctcaaagaccgctacgggcagcgcctggagcagatgtacgccgatat
cgcggccacgcaggccaaccagttgcgcgaactgcggcgcgcggccgccacacaaccggtgatcgacaccctcaccc
aggccgctgccacgatcctcggcaccgggagcgaggtggcatccgacgcccacttcaccgacctgggcggggattcc
ctgtcggcgctgacactttcgaacctgctgagcgatttcttcggtttcgaagttcccgtcggcaccatcgtgaaccc
ggccaccaacctcgcccaactcgcccagcacatcgaggcgcagcgcaccgcgggtgaccgcaggccgagtttcacca
ccgtgcacggcgcggacgccaccgagatccgggcgagtgagctgaccctggacaagttcatcgacgccgaaacgctc
cgggccgcaccgggtctgcccaaggtcaccaccgagccacggacggtgttgctctcgggcgccaacggctggctggg
ccggttcctcacgttgcagtggctggaacgcctggcacctgtcggcggcaccctcatcacgatcgtgcggggccgcg
acgacgccgcggcccgcgcacggctgacccaggcctacgacaccgatcccgagttgtcccgccgcttcgccgagctg
gccgaccgccacctgcgggtggtcgccggtgacatcggcgacccgaatctgggcctcacacccgagatctggcaccg
gctcgccgccgaggtcgacctggtggtgcatccggcagcgctggtcaaccacgtgctccctaccggcagctgttcg
gccccaacgtcgtgggcacggccgaggtgatcaagctggccctcaccgaacggatcaagcccgtcacgtacctgtcc
accgtgtcggtggccatgggggatccccgacttcgaggaggacgcgacatccggaccgtgagcccggtgcgcccgct
cgacggcggatacgccaacggctacggcaacagcaagtgggccggcgaggtgctgctgcgcggggagcccacgatctgt
gcgggctgccgtggcgacgttccgctcggacatgatcctggcgcatccgcgctaccgcggtcaggtcaacgtgcca
gacatgttcacgcgactcctgttgagcctcttgatcaccggcgtcgcgccgcggtcgttctacatcggagacggtga
gcgcccgcgggcgcactacccggcctgacggtcgatttcgtggccgaggcggtcacgacgctcggcgcgcagcagc
gcgagggatacgtgtcctacgacgtgatgaacccgcacgacgacgggatctccctggatgtgttcgtggactggctg
atccgggcgggccatccgatcgaccgggtcgacgactacgacgactgggtgcgtcggttcgagaccgcgttgaccgc
gcttcccgagaagcgccgcgcacagaccgtactgccgctgctgcacgcgttccgcgctccgcaggcaccgttgcgcg
gcgcacccgaacccacggaggtgttccacgccgcggtgcgcaccgcgaaggtgggcccgggagacatcccgcacctc
gacgaggcgctgatcgacaagtacatacgcgatctgcgtgagttcggtctgatctaa
```

MTSDVHDATDGVTETALDDEQSTRRIAELYATDPEFAAAAPLPAVVDAAHKPGLRLAEILQTLFTGYGDRPALGYRA
RELATDEGGRTVTRLLPRFDTLTYAQVWSRVQAVAAALRHNFAQPIYPGDAVATIGFASPDYLTLDLVCAYLGLVSV
PLQHNAPVSRLAPILAEVEPRILTVSAEYLDLAVESVRDVNSVSQLVVFDHHPEVDDHRDALARAREQLAGKGIAVT
TLDAIADEGAGLPAEPIYTADHDQRLAMILYTSGSTGAPKGAMYTEAMVARLWTMSFITGDPTPVINVNFMPLNHLG
GRIPISTAVQNGGTSYFVPESDMSTLFEDLALVRPTELGLVPRVADMLYQHHLATVDRLVTQGADELTAEKQAGAEL
REQVLGGRVITGFVSTAPLAAEMRAFLDITLGAHIVDGYGLTETGAVTRDGVIVRPPVIDYKLIDVPELGYFSTDKP
YPRGELLVRSQTLTPGYYKRPEVTASVFDRDGYYHTGDVMAETAPDHLVYVDRRNNVLKLAQGEFVAVANLEAVFSG
AALVRQIFVYGNSERSFLLAVVVPTPEALEQYDPAALKAALADSLQRTARDAELQSYEVPADFIVETEPFSAANGLL
SGVGKLLRPNLKDRYGQRLEQMYADIAATQANQLRELRRAAATQPVIDTLTQAAATILGTGSEVASDAHFTDLGGDS
LSALTLSNLLSDFFGFEVPVGTIVNPATNLAQLAQHIEAQRTAGDRRPSFTTVHGADATEIRASELTLDKFIDAETL
RAAPGLPKVTTEPRTVLLSGANGWLGRFLTLQWLERLAPVGGTLITIVRGRDDAAARARLTQAYDTDPELSRRFAEL
ADRHLRVVAGDIGDPNLGLTPEIWHRLAAEVDLVVHPAALVNHVLPYRQLFGPNVVGTAEVIKLALTERIKPVTYLS
TVSVAMGIPDFEEDGDIRTVSPVRPLDGGYANGYGNSKWAGEVLLREAHDLCGLPVATFRSDMILAHPRYRGQVNVP
DMFTRLLLSLLITGVAPRSFYIGDGERPRAHYPGLTVDFVAEAVTTLGAQQREGYVSYDVMNPHDDGISLDVFVDWL
IRAGHPIDRVDYDDWVRRFETALTALPEKRRAQTVLPLLHAFRAPQAPLRGAPEPTEVFHAAVRTAKVGPGDIPHL
DEALIDKYIRDLREFGLI

```
atgtcgactgccacccatgacgaacgactcgaccgtcgcgtccacgaactcatcgccaccgaccgcaattcgccgc
cgcccaacccgacccggcgatcaccgccgccctcgaacagcccgggctgcggctgccgcagatcatccgcaccgtgc
tcgacggctacgccgaccggccggcgctgggacagcgcgtggtggagttcgtcacggacgccaagaccgggcgcacg
tcggcgcagctgctcccccgcttcgagaccatcacgtacagcgaagtagcgcagcgtgtttcggcgctgggccgcgc
cctgtccgacgacgcggtgcaccccggcgaccgggtgtgcgtgctgggcttcaacagcgtcgactacgccaccatcg
acatggcgctgggcgccatcggcgccgtctcggtgccgctgcagaccagcgcggcaatcagctcgctgcagccgatc
gtggccgagaccgagcccaccctgatcgcgtccagcgtgaaccagctgtccgacgcggtgcagctgatcaccggcgc
cgagcaggcgcccacccggctggtggtgttcgactaccacccgcaggtcgacgaccagcgcgaggccgtccaggacg
ccgcggcgcggctgtccagcaccggcgtggccgtccagacgctggccgagctgctggagcgcggcaaggacctgccc
gccgtcgcggagccgccgccgacgaggactcgctggccctgctgatctacacctccgggtccaccggcgcccccaa
gggcgcgatgtacccacagagcaacgtcggcaagatgtggcgccgcggcagcaagaactggttcggcgagagcgccg
cgtcgatcaccctgaacttcatgccgatgagccacgtgatgggccgaagcatcctctacggcacgctgggcaacggc
ggcaccgcctactcgccgcccgcagcgacctgtccacccgtgcttgaggacctcgagctggtgcggccaccgagct
caacttcgtcccgcggatctgggagacgctgtacggcgaattccagcgtcaggtcgagcggcggctctccgaggccg
gggacgccggcgaacgtcgcgccgtcgaggccgaggtgctggccgagcagcgccagtacctgctgggcgggcggttc
accttcgcgatgacgggctcggcgcccatctcgccggagctgcgcaactgggtcgagtcgctgctcgaaatgcacct
gatggacggctacggctccaccgaggccggaatggtgttgttcgacggggagattcagcgcccgccggtgatcgact
acaagctggtcgacgtgccggacctgggctacttcagcaccgaccggccgcatccgcgcggcgagctgctgctgcgc
accgagaacatgttcccgggctactacaagcgggccgaaaccaccgcggggcgtcttcgacgaggacggctactaccg
caccggcgacgtgttcgccgagatcgccccggaccggctggtctacgtcgaccgccgcaacaacgtgctcaagctgg
cgcagggcgaattcgtcacgctggccaagctggaggcggtgttcggcaacagccgctgatccgccagatctacgtc
tacggcaacagcgcccagccctacctgctggcggtcggtgccgccaccgaggaggcgctggcctcgggtgacccccga
gacgctcaagcccaagatcgccgactcgctgcagcaggtcgccaaggaggccggcctgcagtcctacgaggtgccgc
gcgacttcatcatcgagaccacccccgttcagcctggaaaacggtctgctgaccgggatccggaagctggcgtggccg
aaactgaagcagcactacggggaacggctggagcagatgtacgccgacctggccgccggacaggccaacgagctggc
cgagctgcgccgcaacggtgcccaggcgccggtgttgcagaccgtgagccgcgccgcgggcgccatgctgggttcgg
ccgcctccgacctgtccccgacgcccacttcaccgatctgggcggagactcgttgtcggcgttgacattcggcaac
ctgctgcgcgagatcttcgacgtcgacgtgccggtaggcgtgatcgtcagcccggccaacgacctgcggccatcgc
gagctacatcgaggccgagcggcagggcagcaagcgcccgacgttcgcctcggtgcacgccgggacgcgaccgtgg
tgcgcgccgccgacctgacgctggacaagttcctcgacgccgagacgctggccgccgcgccgaacctgcccaagccg
gccaccgaggtgcgcaccgtgctgctgaccggcgccaacggcgcttcctgggccgctcacctggccctggaatggctgga
gcggatggacatggtggacggcaaggtcatcgccctggtccgggccgctccgacgaggaggcacgcgcccggctgg
acaagaccttcgacagcggcgacccgaaactgctcgcgcactaccagcagctggccgccgatcacctggaggtcatc
gccggcgacaagggcgaggccaatctgggcctgggccaagacgtttggcaacgactggccgacacggtcgacgtgat
cgtcgaccccgccgcgctggtcaaccacgtgttgccgtacagcgagctgttcgggcccaacgccctgggcaccgcgg
agctgatccggctggcgctgacgtccaagcagaagccgtacacctacgtgtccaccatcggcgtgggcgaccagatc
gagccgggcaagttcgtcgagaacgccgacatccggcagatgagcgccacccgggcgatcaacgacagctacgccaa
cggctatggcaacagcaagtgggccggcgaggtgctgctgcgcgaggcgcacgacctgtgcgggctgcccgtcgcgg
tgttccgctgcgacatgatcctggccgacaccacgtatgccgggcagctcaacctgccggacatgttcacccggctg
atgctgagcctggtggccaccgggatcgcgcccggctcgttctacgacgtcgacgccgacggcaaccggcagcgggc
gcactacgacggcctgccggtcgagttcatcgccgcggcgatctcgacgctgggttcgcagatcaccgacagcgaca
ccggcttccagacctaccacgtgatgaaccccctacgatgacggcgtcggtctggacgagtacgtcgattggctggtg
gacgccggctattcgatcgagcggatcgccgactactccgaatggctgcggcggttcgagacctcgctgcgggccct
gccggaccggcagcgccagtactcgctgctgccgctgctgcacaactaccgcacgccggagaagccgatcaacgggt
cgatagctcccaccgacgtgttccgggcagcggtgcaggaggcgaaaatcggcccgacaaagacattccgcacgtg
tcgccgccggtcatcgtcaagtacatcaccgacctgcagctgctcgggctgctctaa
```

MSTATHDERLDRRVHELIATDPQFAAAQPDPAITAALEQPGLRLRLPQIIRTVLDGYADRPALGQRVVEFVTDAKTGRT
SAQLLPRFETITYSEVAQRVSALGRALSDDAVHPGDRVCVLGFNSVDYATIDMALGAIGAVSVPLQTSAAISSLQPI
VAETEPTLIASSVNQLSDAVQLITGAEQAPTRLVVFDYHPQVDDQREAVQDAAARLSSTGVAVQTLAELLERGKDLP
AVAEPPADEDSLALLIYTSGSTGAPKGAMYPQSNVGKMWRRGSKNWFGESAASITLNFMPMSHVMGRSILYGTLGNG
GTAYFAARSDLSTLLEDLELVRPTELNFVPRIWETLYGEFQRQVERRLSEAGDAGERRAVEAEVLAEQRQYLLGGRF
TFAMTGSAPISPELRNWVESLLEMHLMDGYGSTEAGMVLFDGEIQRPPVIDYKLVDVPDLGYFSTDRPHPRGELLLR
TENMFPGYYKRAETTAGVFDEDGYYRTGDVFAEIAPDRLVYVDRRNNVLKLAQGEFVTLAKLEAVFGNSPLIRQIYV
YGNSAQPYLLAVVPTEEALASGDPETLKPKIADSLQQVAKEAGLQSYEVPRDFIIETTPFSLENGLLTGIRKLAWP
KLKQHYGERLEQMYADLAAGQANELAELRRNGAQAPVLQTVSRAAGAMLGSAASDLSPDAHFTDLGGDSLSALTFGN
LLREIFDVDVPVGVIVSPANDLAAIASYIEAERQGSKRPTFASVHGRDATVVRAADLTLDKFLDAETLAAAPNLPKP
ATEVRTVLLTGATGFLGRYLALEWLERMDMVDGKVIALVRARSDEEARARLDKTFDSGDPKLLAHYQQLAADHLEVI
AGDKGEANLGLGQDVWQRLADTVDVIVDPAALVNHVLPYSELFGPNALGTAELIRLALTSKQKPYTYVSTIGVGDQI
EPGKFVENADIRQMSATRAINDSYANGYGNSKWAGEVLLREAHDLCGLPVAVFRCDMILADTTYAGQLNLPDMFTRL
MLSLVATGIAPGSFYELDADGNRQRAHYDGLPVEFIAAAISTLGSQITDSDTGFQTYHVMNPYDDGVGLDEYVDWLV
DAGYSIERIADYSEWLRRFETSLRALPDRQRQYSLLPLLHNYRTPEKPINGSIAPTDVFRAAVQEAKIGPDKDIPHV
SPPVIVKYITDLQLLGLL

```
atgtcgccaatcacgcgtgaagagcggctcgagcgccgcatccaggacctctacgccaacgaccgcagttcgccgc
cgccaaaccogccacggcgatcaccgcagcaatcgagcggccgggtctaccgctacccagatcatcgagaccgtca
tgaccggatacgccgatcggccggctctcgctcagcgctcggtcgaattcgtgaccgacgccggcaccggccacac
acgctgcgactgctcccccacttcgaaaccatcagctacggcgagctttgggaccgcatcagcgcactggccgacgt
gctcagcaccgaacagacggtgaaaccgggcgaccgggtctgcttgttgggcttcaacagcgtcgactacgccacga
tcgacatgactttggcgcggctgggcgcggtggccgtaccactgcagaccagcgcggcgataacccagctgcagccg
atcgtcgccgagacccagcccaccatgatcgcggccagcgtcgacgcactcgctgacgccaccgaattggctctgtc
cggtcagaccgctacccgagtcctggtgttcgaccaccaccggcaggttgacgcacaccgcgcagcggtcgaatccg
cccgggagcgcctggccggctcggcggtcgtcgaaaccctggccgaggccatcgcgcgcggcgacgtgccccgcggt
gcgtccgccggctcggcgcccggcaccgatgtgtccgacgactcgctcgcgctactgatctacacctcgggcagcac
gggtgcgcccaagggcgcgatgtaccccgacgcaacgttgcgaccttctggcgcaagcgcacctggttcgaaggcg
gctacgagccgtcgatcacgctgaacttcatgccaatgagccacgtcatgggccgccaaatcctgtacggcacgctg
tgcaatggcggcaccgcctacttcgtggcgaaaagcgatctctccaccttgttcgaagacctggcgctggtgcggcc
caccgagctgaccttcgtgccgcgcgtgtgggacatggtgttcgacgagtttcagagtgaggtcgaccgccgcctgg
tcgacggccgaccgggtcgcgctcgaagcccaggtcaaggccgagatacgcaacgacgtgctcggtggacggtat
accagcgcactgaccggctccgccctatctccgacgagatgaaggcgtgggtcgaggagctgctcgacatgcatct
ggtcgagggctacggctccaccgaggccgggatgatcctgatcgacggagccattcggcgcccggcggtactcgact
acaagctggtcgatgttcccgacctgggttacttcctgaccgaccggccacatccgcgggcgagttgctggtcaag
accgatagtttgttcccgggctactaccagcgagccgaagtcaccgccgacgtgttcgatgctgacggcttctaccg
gaccggcgacatcatggccgaggtcggccccgaacagttcgtgtacctcgaccgccgcaacaacgtgttgaagctgt
cgcagggcgagttcgtcaccgtctccaaactcgaagcggtgtttggcgacagcccactggtacggcagatctacatc
tacggcaacagcgcccgtgcctacctgttggcggtgatcgtccccacccaggaggcgctggacgccgtgcctgtcga
ggagctcaaggcgcggctgggcgactcgctgcaagaggtcgcaaaggccgccggcctgcagtcctacgagatcccgc
gcgacttcatcatcgaaacaaccaccatggacgctgaagaacggcctgctcaccggcatccgcaagttggccaggccg
cagctgaaaaagcattacgcgagcttctcgagcagatctacacggacctggcacacggccaggccggacgaactgcg
ctcgctgcgccaaagcggtgccgatgcgccggtgctggtgacggtgtgccgtgcggcggccgcgctgttgggcggca
gcgcctctgacgtccagcccgatgcgcacttcaccgatttgggcggcgactcgctgtcggcgctgtcgttcaccaac
ctgctgcacgagatcttcgacatcgaagtgccggtgggcgtcatcgtcagccccgccaacgacttgcaggccctggc
cgactacgtcgaggcggctcgcaaacccggctcgtcacggccgaccttcgcctcggtccacggcgcctcgaatgggc
aggtcaccgaggtgcatgccggtgacctgtccctggacaaattcatcgatgccgcaaccctggccgaagctcccgg
ctgccgccgcaaacacccaagtgcgcaccgtgctgctgaccggcgccaccggcttcctcgggcgctacctggccct
ggaatggctggagcggatggacctggtcgacggcaaactgatctgcctggtccgggccaagtccgacaccgaagcac
gggcgcggctggacaagacgttcgacagcggcgaccccgaactgctggccccactaccgcgcactggccggcgaccac
ctcgaggtgctcgccggtgacaagggcgaagccgacctcggactggaccggcagacctggcaacgcctggccgacac
ggtcgacctgatcgtcgaccccgcggccctggtcaaccacgtactgccatacagccagctgttcgggcccaacgcgc
tgggcaccgccgagctgctgcggctggcgctcacctccaagatcaagccctacagctacacctcgacaatcggtgtc
gccgaccagatcccgccgtcggcgttcaccgaggacgccgacatccgggtcatcagcgccacccgcgcggtcgacga
cagctacgccaatggctactcgaacagcaagtgggccggcgaggtgctgttgcgcgaggcgcatgacctgtgtggcc
tgccggttcggtgttccgctgcgacatgatcctggccgacaccacatgggcgggacagctcaatgtgccggacatg
ttcacccggatgatcctgagcctggcggccaccggtatcgcgccgggttcgttctatgagcttgcggccgacggcgc
ccggcaacgcgcccactatgacggtctgcccgtcgagttcatcgccgaggcgatttcgactttgggtgcgcagagcc
aggatggtttccacacgtatcacgtgatgaaccctacgacgacggcatcggactcgacgagttcgtcgactggctc
aacgagtccggttgccccatccagcgcatcgctgactatggcgactggctgcagcgcttcgaaaccgcactgcgcgc
actgcccgatcggcagcggcacagctcactgctgccgctgttgcacaactatcggcagccggagcggcccgtccgcg
ggtcgatcgccctaccgatcgcttccgggcagcggtgcaagaggccaagatcggccccgacaaagacattccgcac
gtcggcgcgccgatcatcgtgaagtacgtcagcgacctgcgcctactcggcctgctctaa
```
FIGURE 14A

FIGURE 14B

MSPITREERLERRIQDLYANDPQFAAAKPATATTAAIERPGLPLPQIIETVMTGYADRPALAQRSVEFVTDAGTGHT
TLRLLPHFETISYGELWDRISALADVLSTEQTVKPGDRVCLLGFNSVDYATIDMTLARLGAVAVPLQTSAAITQLQP
IVAETQPTMIAASVDALADATELALSGQTATRVLVFDHHRQVDAHRAAVESARERLAGSAVVETLAEAIARGDVPRG
ASAGSAPGTDVSDDSLALLIYTSGSTGAPKGAMYPRRNVATFWRKRTWFEGGYEPSITLNFMPMSHVMGRQILYGTL
CNGGTAYFVAKSDLSTLFEDLALVRPTELTFVPRVWDMVFDEFQSEVDRRLVDGADRVALEAQVKAEIRNDVLGGRY
TSALTGSAPISDEMKAWVEELLDMHLVEGYGSTEAGMILIDGAIRRPAVLDYKLVDVPDLGYFLTDRPHPRGELLVK
TDSLFPGYYQRAEVTADVFDADGFYRTGDIMAEVGPEQFVYLDRRNNVLKLSQGEFVTVSKLEAVFGDSPLVRQIYI
YGNSARAYLLAVIVPTQEALDAVPVEELKARLGDSLQEVAKAAGLQSYEIPRDFIIETTPWTLENGLLTGIRKLARP
QLKKHYGELLEQIYTDLAHGQADELRSLRQSGADAPVLVTVCRAAAALLGGSASDVQPDAHFTDLGGDSLSALSFTN
LLHEIFDIEVPVGVIVSPANDLQALADYVEAARKPGSSRPTFASVHGASNGQVTEVHAGDLSLDKFIDAATLAEAPR
LPAANTQVRTVLLTGATGFLGRYLALEWLERMDLVDGKLICLVRAKSDTEARARLDKTFDSGDPELLAHYRALAGDH
LEVLAGDKGEADLGLDRQTWQRLADTVDLIVDPAALVNHVLPYSQLFGPNALGTAELLRLALTSKIKPYSYTSTIGV
ADQIPPSAFTEDADIRVISATRAVDDSYANGYSNSKWAGEVLLREAHDLCGLPVAVFRCDMILADTTWAGQLNVPDM
FTRMILSLAATGIAPGSFYELAADGARQRAHYDGLPVEFIAEAISTLGAQSQDGFHTYHVMNPYDDGIGLDEFVDWL
NESGCPIQRIADYGDWLQRFETALRALPDRQRHSSLLPLLHNYRQPERPVRGSIAPTDRFRAAVQEAKIGPDKDIPH
VGAPIIVKYVSDLRLLGLL

```
atgagcaccgcaacccatgatgaacgtctggatcgtcgtgttcatgaactgattgcaaccgatc
cgcagtttgcagcagcacagccggatcctgcaattaccgcagcactggaacagcctggtctgcg
tctgccgcagattattcgtaccgttctggatggttatgcagatcgtccggcactgggtcagcgt
gttgttgaatttgttaccgatgcaaaaaccggtcgtaccagcgcacagctgctgcctcgttttg
aaaccattacctatagcgaagttgcacagcgtgttagcgcactgggtcgtgcactgagtgatga
tgcagttcatccgggtgatcgtgtttgtgttctgggttttaatagcgttgattatgccaccatt
gatatggcactgggtgcaattggtgcagttagcgttccgctgcagaccagcgcagcaattagca
gcctgcagccgattgttgcagaaaccgaaccgaccctgattgcaagcagcgttaatcagctgtc
agatgcagttcagctgattaccggtgcagaacaggcaccgacccgtctggttgtttttgattat
catccgcaggttgatgatcagcgtgaagcagttcaggatgcagcagcacgtctgagcagcaccg
gtgttgcagttcagaccctggcagaactgctggaacgtggtaaagatctgcctgcagttgcaga
accgcctgcagatgaagatagcctggcactgctgatttataccagcggtagcacaggtgcaccg
aaaggtgcaatgtatccgcagagcaatgttggtaaaatgtggcgtcgtggtagcaaaaattggt
ttggtgaaagcgcagcaagcattaccctgaatttcatgccgatgagccatgttatgggtcgtag
cattctgtatggcaccctgggtaatggtggcaccgcatattttgcagcacgtagcgatctgagc
accctgctggaagatctggaactggttcgtccgaccgaactgaattttgttccgcgtatttggg
aaaccctgtatggtgaatttcagcgtcaggttgaacgtcgtctgagcgaagctggcgatgccgg
tgaacgtcgtgcagttgaagcagaagttctggcagaacagcgtcagtatctgctgggtggtcgt
tttacctttgcaatgaccggtagcgcaccgattagtccggaactgcgtaattgggttgaaagcc
tgctggaaatgcatctgatggatggctatggtagcaccgaagcaggtatggttctgtttgatgg
cgaaattcagcgtccgcctgtgattgattataaactggttgatgttccggatctgggttattt
agcaccgatcgtccgcatccgcgtggtgaactgctgctgcgtaccgaaaatatgtttccgggtt
attataaacgtgcagaaaccaccgcaggcgttttgatgaagatggttattatcgtaccggtga
tgtgtttgcagaaattgcaccggatcgtctggtttatgttgatcgtcgtaataatgttctgaaa
ctggcacagggtgaatttgtgaccctggccaaactggaagcagttttttggtaatagtccgctga
ttcgtcagatttatgtgtatggtaatagcgcacagccgtatctgctggcagttgttgttccgac
cgaagaggcactggcaagcggtgatccggaaaccctgaaaccgaaaattgcagatagcctgcag
caggttgcaaaagaagcaggtctgcagagctatgaagttccgcgtgattttattattgaaacca
ccccgtttagcctggaaaatggtctgctgaccggtattcgtaaactggcatggccgaaactgaa
acagcattatggtgaacgcctggaacaaatgtatgcagatctggcagcaggtcaggcaaatgaa
ctggccgaactgcgtcgtaatggtgcacaggcaccggttctgcagaccgttagccgtgcagccg
gtgcaatgctgggtagcgcagccagcgatctgagtccggatgcacattttaccgatctgggtgg
tgatagcctgagcgcactgacctttggtaatctgctgcgtgaaatttttgatgttgatgtgccg
gttggtgttattgttagtccggctaatgatctggcagccattgcaagctatattgaagcagaac
gtcagggtagcaaacgtccgacctttgcaagcgttcatggtcgtgatgcaaccgttgttcgtgc
agcagatctgaccctggataaatttctggatgcagaaacccggcagcagcaccgaatctgccg
aaaccggcaaccgaagttcgtaccgtgctgctgacaggtgcaaccggttttctgggtcgttatc
tggcactggaatggctggaacgtatggatatggttgatggtaaagttattgcactggttcgtgc
ccgtagtgatgaagaagcacgcgcacgtctggataaaaccctttgatagtggtgatccgaaactg
ctggcacattatcagcagctggctgcagatcatctggaagttattgccggtgataaaggtgaag
caaatctgggtctgggtcaggatgtttggcagcgtctggcagataccgttgatgttattgtgga
tccggcagcactggttaatcatgttctgccgtatagcgaactgtttggtccgaatgcactgggc
```

FIGURE 15A

```
accgcagaactgattcgtctggcactgaccagcaaacagaaaccgtatacctatgttagcacca
ttggtgttggcgatcagattgaaccgggtaaatttgttgaaaatgccgatattcgtcagatgag
cgcaacccgtgcaattaatgatagctatgcaaatggctacggcaatagcaaatgggcaggcgaa
gttctgctgcgcgaagcacatgatctgtgtggtctgccggttgcagttttttcgttgtgatatga
ttctggccgataccacctatgcaggtcagctgaatctgccggatatgtttacccgtctgatgct
gagcctggttgcaaccggtattgcaccgggtagctttatgaactggatgcagatggtaatcgt
cagcgtgcacattatgatggcctgccggttgaatttattgcagcagccattagcaccctggtt
cacagattaccgatagcgataccggttttcagacctatcatgttatgaacccgtatgatgatgg
tgttggtctggatgaatatgttgattggctggttgatgccggttatagcattgaacgtattgca
gattatagcgaatggctgcgtcgctttgaaacctcactgcgtgcactgccggatcgtcagcgcc
agtatagcctgctgccgctgctgcacaattatcgtacaccggaaaaaccgattaatggtagcat
tgcaccgaccgatgtttttcgtgcagccgttcaagaagccaaaattggtccggataaagatatt
ccgcatgttagccctccggtgattgttaaatatattaccgatctgcagctgctgggtctgctgt
aa
```

FIGURE 15A cont.

```
MSTATHDERLDRRVHELIATDPQFAAAQPDPAITAALEQPGLRLPQIIRTVLDGYADRPALGQR
VVEFVTDAKTGRTSAQLLPRFETITYSEVAQRVSALGRALSDDAVHPGDRVCVLGFNSVDYATI
DMALGAIGAVSVPLQTSAAISSLQPIVAETEPTLIASSVNQLSDAVQLITGAEQAPTRLVVFDY
HPQVDDQREAVQDAAARLSSTGVAVQTLAELLERGKDLPAVAEPPADEDSLALLIYTSGSTGAP
KGAMYPQSNVGKMWRRGSKNWFGESAASITLNFMPMSHVMGRSILYGTLGNGGTAYFAARSDLS
TLLEDLELVRPTELNFVPRIWETLYGEFQRQVERRLSEAGDAGERRAVEAEVLAEQRQYLLGGR
FTFAMTGSAPISPELRNWVESLLEMHLMDGYGSTEAGMVLFDGEIQRPPVIDYKLVDVPDLGYF
STDRPHPRGELLLRTENMFPGYYKRAETTAGVFDEDGYYRTGDVFAEIAPDRLVYVDRRNNVLK
LAQGEFVTLAKLEAVFGNSPLIRQIYVYGNSAQPYLLAVVVPTEEALASGDPETLKPKIADSLQ
QVAKEAGLQSYEVPRDFIIETTPFSLENGLLTGIRKLAWPKLKQHYGERLEQMYADLAAGQANE
LAELRRNGAQAPVLQTVSRAAGAMLGSAASDLSPDAHFTDLGGDSLSALTFGNLLREIFDVDVP
VGVIVSPANDLAAIASYIEAERQGSKRPTFASVHGRDATVVRAADLTLDKFLDAETLAAAPNLP
KPATEVRTVLLTGATGFLGRYLALEWLERMDMVDGKVIALVRARSDEEARARLDKTFDSGDPKL
LAHYQQLAADHLEVIAGDKGEANLGLGQDVWQRLADTVDVIVDPAALVNHVLPYSELFGPNALG
TAELIRLALTSKQKPYTYVSTIGVGDQIEPGKFVENADIRQMSATRAINDSYANGYGNSKWAGE
VLLREAHDLCGLPVAVFRCDMILADTTYAGQLNLPDMFTRLMLSLVATGIAPGSFYELDADGNR
QRAHYDGLPVEFIAAAISTLGSQITDSDTGFQTYHVMNPYDDGVGLDEYVDWLVDAGYSIERIA
DYSEWLRRFETSLRALPDRQRQYSLLPLLHNYRTPEKPINGSIAPTDVFRAAVQEAKIGPDKDI
PHVSPPVIVKYITDLQLLGLL
```

FIGURE 15B

MICROORGANISMS FOR PRODUCING PROPYLENE AND METHODS RELATED THERETO

This application claims the benefit of priority of U.S. Provisional application Ser. No. 61/500,087, filed Jun. 22, 2011, the entire contents of which are incorporated herein by reference.

The instant application contains a Sequence Listing which has been submitted via EFS-Web and is hereby incorporated by reference in its entirety. Said ASCII copy, created on Jun. 18, 2012, is named 871943-999137_US_Sequence_Listing.txt and is 77,759 bytes in size.

BACKGROUND OF THE INVENTION

The present invention relates generally to biosynthetic processes, and more specifically to organisms having propylene biosynthetic capability.

Propylene is produced primarily as a by-product of petroleum refining and of ethylene production by steam cracking of hydrocarbon feedstocks. Propene is separated by fractional distillation from hydrocarbon mixtures obtained from cracking and other refining processes. Typical hydrocarbon feedstocks are from non-renewable fossil fuels, such as petroleum, natural gas and to a much lesser extent coal. Over 75 billion pounds of propylene are manufactured annually, making it the second largest fossil-based chemical produced behind ethylene. Propylene is a base chemical that is converted into a wide range of polymers, polymer intermediates and chemicals. Some of the most common derivatives of chemical and polymer grade propylene are polypropylene, acrylic acid, butanol, butanediol, acrylonitrile, propylene oxide, isopropanol and cumene. The use of the propylene derivative, polypropylene, in the production of plastics, such as injection moulding, and fibers, such as carpets, accounts for over one-third of U.S. consumption for this derivative. Propylene is also used in the production of synthetic rubber and as a propellant or component in aerosols.

The ability to manufacture propylene from alternative and/or renewable feedstocks would represent a major advance in the quest for more sustainable chemical production processes. One possible way to produce propylene renewably involves fermentation of sugars or other feedstocks to produce the alcohols 2-propanol (isopropanol) or 1-propanol, which is separated, purified, and then dehydrated to propylene in a second step involving metal-based catalysis. Direct fermentative production of propylene from renewable feedstocks would obviate the need for dehydration. During fermentative production, propylene gas would be continuously emitted from the fermenter, which could be readily collected and condensed. Developing a fermentative production process would also eliminate the need for fossil-based propylene and would allow substantial savings in cost, energy, and harmful waste and emissions relative to petrochemically-derived propylene.

Microbial organisms and methods for effectively producing propylene from cheap renewable feedstocks such as molasses, sugar cane juice, and sugars derived from biomass sources, including agricultural and wood waste, as well as C1 feedstocks such as syngas and carbon dioxide, are described herein and include related advantages.

SUMMARY OF THE INVENTION

The invention provides non-naturally occurring microbial organisms containing propylene pathways comprising at least one exogenous nucleic acid encoding a propylene pathway enzyme expressed in a sufficient amount to produce propylene. The invention additionally provides methods of using such microbial organisms to produce propylene, by culturing a non-naturally occurring microbial organism containing propylene pathways as described herein under conditions and for a sufficient period of time to produce propylene.

BRIEF DESCRIPTION OF THE DRAWINGS

FIG. 10A shows the nucleotide sequence (SEQ ID NO: 1) of carboxylic acid reductase from *Nocardia iowensis* (GNM_720), and FIG. 10B shows the encoded amino acid sequence (SEQ ID NO: 2).

FIG. 11A shows the nucleotide sequence (SEQ ID NO: 3) of phosphpantetheine transferase, which was codon optimized, and FIG. 11B shows the encoded amino acid sequence (SEQ ID NO: 4).

FIG. 12A shows the nucleotide sequence (SEQ ID NO: 5) of carboxylic acid reductase from *Mycobacterium smegmatis* mc(2)155 (designated 890), and FIG. 12B shows the encoded amino acid sequence (SEQ ID NO: 6).

FIG. 13A shows the nucleotide sequence (SEQ ID NO: 7) of carboxylic acid reductase from *Mycobacterium avium* subspecies paratuberculosis K-10 (designated 891), and FIG. 13B shows the encoded amino acid sequence (SEQ ID NO: 8).

FIG. 14A shows the nucleotide sequence (SEQ ID NO: 9) of carboxylic acid reductase from *Mycobacterium marinum* M (designated 892), and FIG. 14B shows the encoded amino acid sequence (SEQ ID NO: 10).

FIG. 15A shows the nucleotide sequence (SEQ ID NO: 11) of carboxylic acid reductase designated 891GA, and FIG. 15B shows the encoded amino acid sequence (SEQ ID NO: 12).

DETAILED DESCRIPTION OF THE INVENTION

The present invention is directed to the design and production of cells and organisms having biosynthetic production capabilities for propylene. The invention, in particular, relates to the design of microbial organism capable of producing propylene by introducing one or more nucleic acids encoding a propylene pathway enzyme.

In one embodiment, the invention utilizes in silico stoichiometric models of *Escherichia coli* metabolism that identify metabolic designs for biosynthetic production of propylene. The results described herein indicate that metabolic pathways can be designed and recombinantly engineered to achieve the biosynthesis of propylene in *Escherichia coli* and other cells or organisms. Biosynthetic production of propylene, for example, for the in silico designs can be confirmed by construction of strains having the designed metabolic genotype. These metabolically engineered cells or organisms also can be subjected to adaptive evolution to further augment propylene biosynthesis, including under conditions approaching theoretical maximum growth.

In certain embodiments, the propylene biosynthesis characteristics of the designed strains make them genetically stable and particularly useful in continuous bioprocesses. Separate strain design strategies were identified with incorporation of different non-native or heterologous reaction capabilities into *E. coli* or other host organisms leading to propylene producing metabolic pathways from either 2-ketoglutarate or pyruvate. In silico metabolic designs were identified that resulted in the biosynthesis of propylene in microorganisms from each of these substrates or metabolic intermediates.

Strains identified via the computational component of the platform can be put into actual production by genetically engineering any of the predicted metabolic alterations, which lead to the biosynthetic production of propylene or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

The maximum theoretical propylene yield from glucose is 1.33 mol/mol (0.311 g/g):

Figure 2:
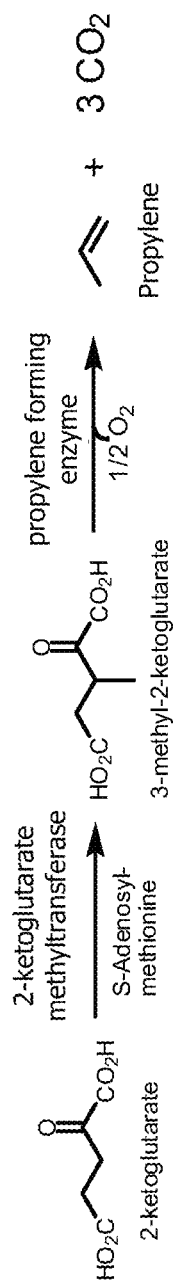
FIG. 2 shows an exemplary pathway for production of propylene from 2-ketoglutarate by a 2-ketoglutarate methyltransferase and a propylene forming enzyme.
Figure 3:
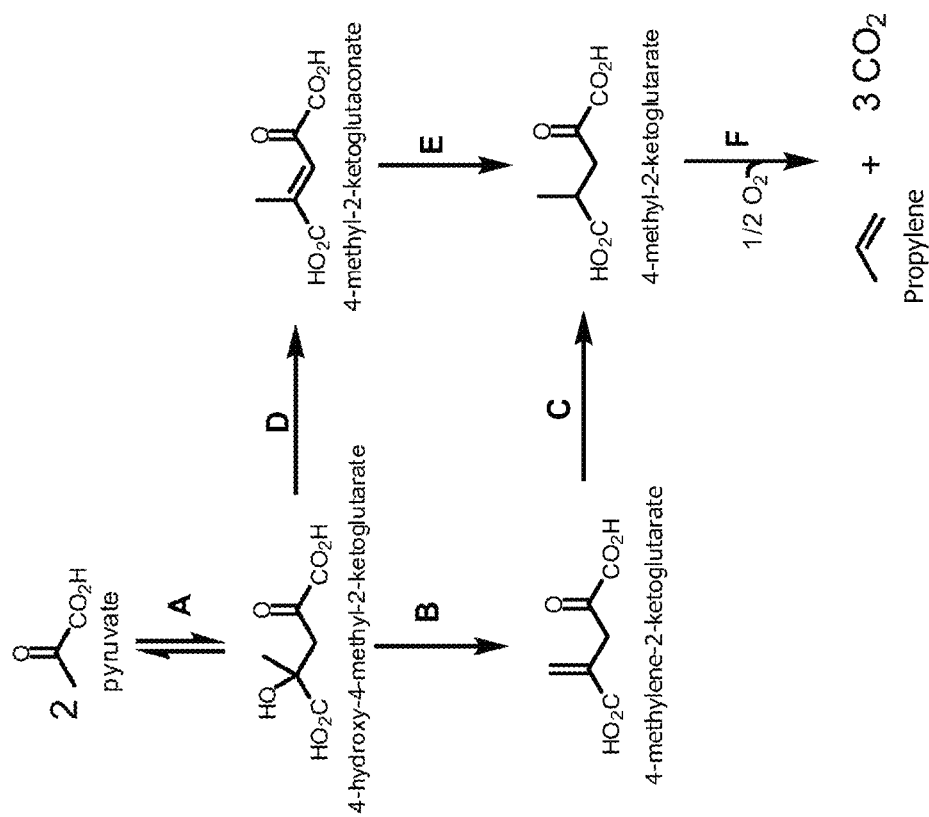
FIG. 3 shows exemplary pathways for production of propylene from pyruvate. Enzymes for transformation of the identified substrates to products include: A) a 4-hydroxy-4-methyl-2-ketoglutarate aldolase, B) a 4-hydroxy-4-methyl-2-ketoglutarate dehydratase II, C) a 4-hydroxy-4-methyl-2-ketoglutarate dehydratase I, D) a 4-methylene-2-ketoglutarate reductase, E) a 4-methyl-2-ketoglutaconate reductase, and F) a propylene forming enzyme.

The pathways presented in FIGS. 2 and 3 achieve a yield of 1 mole propylene per mole of glucose utilized assuming 2 pyruvate molecules or 1 alpha-ketoglutarate molecule can be formed from glucose. Increasing product yields to 1.33 mol/mol is possible if cells are capable of fixing some of the $CO_2$ released from the depicted pathways or from the production of alpha-ketoglutarate through carbon-fixing mechanisms such as the reductive (or reverse) TCA cycle or the Wood-Ljungdahl pathway supplemented with pyruvate:ferredoxin oxidoreductase.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a propylene biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "propylene," having the molecular formula $C_3H_6$ and a molecular mass of 42.08 g/mol (see FIGS. 2 and 3) (IUPAC name Propene) is used interchangeably throughout with 1-propene, 1-propylene, methylethene and methylethylene. At room temperature, propylene is a colorless gas with a weak but unpleasant smell. Propylene has a higher density and boiling point than ethylene due to its greater size, whereas it has a slightly lower boiling point than propane in addition to being more volatile. Propylene lacks strongly polar bonds, yet the molecule has a small dipole moment due to its reduced symmetry. Propylene is also a structural isomer to cyclopropane.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "S-Adenosyl methionine" or "SAM," having the molecular formula $C_{15}H_{22}N_6O_5S^+$ and a molecular mass of 398.44 g/mol (IUPAC name: (2S)-2-Amino-4-[[(2S,3S,4R,5R)-5-(6-aminopurin-9-yl)-3,4-dihydroxyoxolan-2-yl]methyl-methylsulfonio]butanoate) is a co-substrate involved in methyl group transfers. Transmethylation, transsulfuration, and aminopropylation are some of the metabolic pathways that use SAM. The methyl group ($CH_3$) attached to the methionine sulfur atom in SAM is chemically reactive. This allows donation of this group to an acceptor substrate in transmethylation reactions.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having propylene biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan-05-1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sept-16-1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism, including a microbial organism having a propylene pathway having at least one exogenous nucleic acid encoding a propylene pathway enzyme expressed in a sufficient amount to produce propylene, the propylene pathway including a 2-ketoglutarate methyltransferase or a propylene forming enzyme (see FIG. 2, steps 1-2). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a 2-ketoglutarate methyltransferase and a propylene forming enzyme (see FIG. 2, steps 1 and 2).

In some embodiments, the invention provides a non-naturally occurring microbial organism, including a microbial organism having a propylene pathway having at least one exogenous nucleic acid encoding a propylene pathway enzyme expressed in a sufficient amount to produce propylene, the propylene pathway including a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, a 4-methyl-2-ketoglutaconate reductase or a propylene forming enzyme (see FIG. 3, steps A-F). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a 4-hydroxy-4-methyl-2-ketoglutarate aldolase, a 4-hydroxy-4-methyl-2-ketoglutarate dehydratase II, a 4-methylene-2-ketoglutarate reductase and a propylene forming enzyme (see FIG. 3, steps A, B, C and F). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a 4-hydroxy-4-methyl-2-ketoglutarate aldolase, a 4-hydroxy-4-methyl-2-ketoglutarate dehydratase I, a 4-methyl-2-ketoglutaconate reductase and a propylene forming enzyme (see FIG. 3, steps A, D, E and F).

Figure 4:
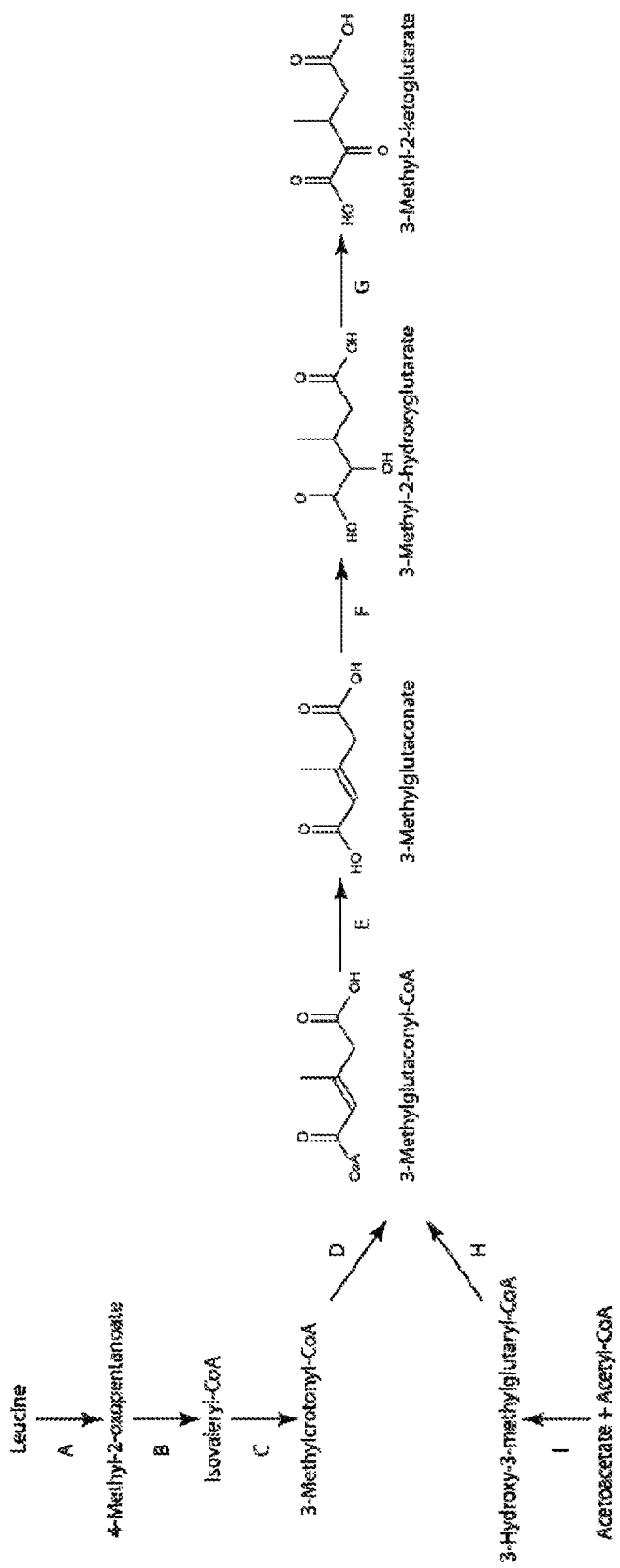
FIG. 4 shows pathways from leucine and acetoacetate to 3-methyl-2-ketoglutarate. Enzymes for transformation of the identified substrates to products include: A. Leucine aminotransferase, dehydrogenase (deaminating) or oxidase, B. 4-methyl-2-oxopentanoate dehydrogenase, C. isovaleryl-CoA dehydrogenase, D. 3-methylcrotonyl-CoA carboxylase, E. 3-methylglutaconyl-CoA hydrolase, transferase or synthetase, F. 3-methylglutaconate hydratase, G. 3-methyl-2-hydroxyglutarate dehydrogenase, H. 3-hydroxy-3-methylglutaryl-CoA dehydratase and I. 3-hydroxy-3-methylglutaryl-CoA lyase.

In some embodiments, the invention provides a non-naturally occurring microbial organism, including a microbial organism having a propylene pathway having at least one exogenous nucleic acid encoding a propylene pathway enzyme expressed in a sufficient amount to produce propylene, the propylene pathway including a leucine aminotransferase, dehydrogenase (deaminating) or oxidase; a 4-methyl-2-oxopentanoate dehydrogenase; an isovaleryl-CoA dehydrogenase; a 3-methylcrotonyl-CoA carboxylase; a 3-methylglutaconyl-CoA hydrolase, transferase or synthetase; a 3-methylglutaconate hydratase; a 3-methyl-2-hydroxyglutarate dehydrogenase; a 3-hydroxy-3-methylglutaryl-CoA dehydratase; or a 3-hydroxy-3-methylglutaryl-CoA lyase (see FIG. 4, steps A-I). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a leucine aminotransferase, dehydrogenase (deaminating) or oxidase; a 4-methyl-2-oxopentanoate dehydrogenase; a isovaleryl-CoA dehydrogenase; a 3-methylcrotonyl-CoA carboxylase; a 3-methylglutaconyl-CoA hydrolase, transferase or synthetase; a 3-methylglutaconate hydratase; a 3-methyl-2-hydroxyglutarate dehydrogenase and a propylene forming enzyme (see FIG. 4, steps A-G and FIG. 2, step 2). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a 3-methylglutaconyl-CoA hydrolase, transferase or synthetase; a 3-methylglutaconate hydratase; a 3-methyl-2-hydroxyglutarate dehydrogenase; a 3-hydroxy-3-methylglutaryl-CoA dehydratase; a 3-hydroxy-3-methylglutaryl-CoA lyase and a propylene forming enzyme (see FIG. 4, steps I, H, E-G and FIG. 2, step 2). Sources of encoding nucleic acids for a propylene pathway enzyme or protein described above are well known in the art and can be obtained from a variety of species including, but limited to, those exemplified herein.

Figure 5:
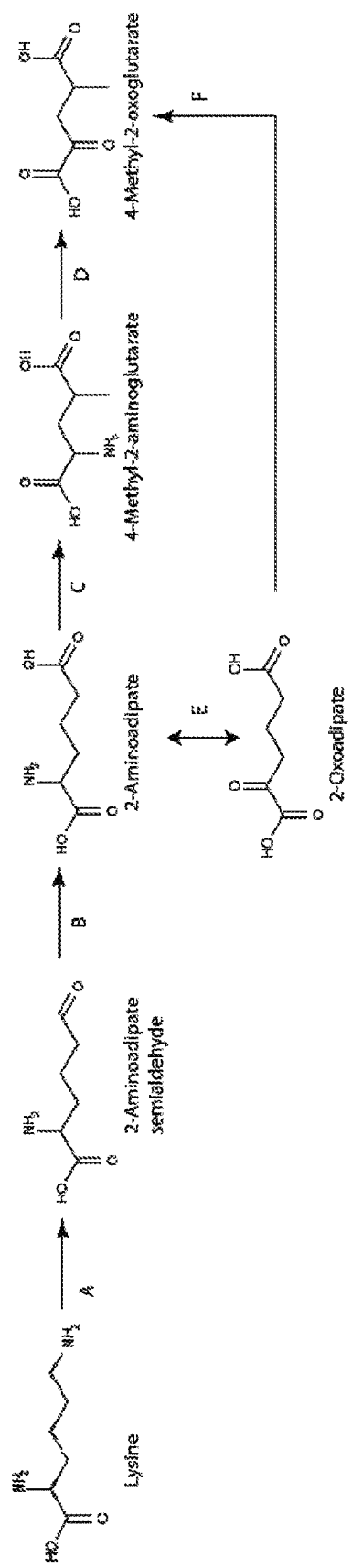
FIG. 5 shows pathways to 4-methyl-2-oxoglutarate from lysine. Enzymes for transformation of the identified substrates to products include: A. Lysine 6-aminotransferase, 6-dehydrogenase (deaminating) or 6-oxidase, B. 2-aminoadipate dehydrogenase, C. 2-aminoadipate mutase, D. 4-methyl-2-aminoglutarate aminotransferase, dehydrogenase (deaminating) or oxidase, E. 2-aminoadipate aminotransferase, dehydrogenase (deaminating) or oxidase, and F. 2-oxoadipate mutase.

In some embodiments, the invention provides a non-naturally occurring microbial organism, including a microbial organism having a propylene pathway having at least one exogenous nucleic acid encoding a propylene pathway enzyme expressed in a sufficient amount to produce propylene, the propylene pathway including a lysine 6-aminotransferase, a 6-dehydrogenase (deaminating) or 6-oxidase; an 2-aminoadipate dehydrogenase; an 2-aminoadipate mutase; a 4-methyl-2-aminoglutarate aminotransferase, dehydrogenase (deaminating) or oxidase; a 2-aminoadipate aminotransferase, dehydrogenase (deaminating) or oxidase; or a 2-oxoadipate mutase (see FIG. 5, steps A-F). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a lysine 6-aminotransferase, 6-dehydrogenase (deaminating) or 6-oxidase; an 2-aminoadipate dehydrogenase, an 2-aminoadipate mutase; a 4-methyl-2-aminoglutarate aminotransferase, dehydrogenase (deaminating) or oxidase; and a propylene forming enzyme (see FIG. 5, steps A-D, FIG. 3, step F). In one aspect, the non-naturally occurring microbial organism includes a microbial organism having a propylene pathway having at least one exogenous nucleic acid encoding propylene pathway enzymes expressed in a sufficient amount to produce propylene, the propylene pathway including a lysine 6-aminotransferase, 6-dehydrogenase (deaminating) or 6-oxidase; a 2-aminoadipate dehydrogenase; an 2-aminoadipate aminotransferase, dehydrogenase (deaminating) or oxidase; an 2-oxoadipate mutase; and a propylene forming enzyme (see FIG. 5, steps A, B, E and F, FIG. 3, step F). Sources of encoding nucleic acids for a propylene pathway enzyme or protein described above are well known in the art and can be obtained from a variety of species including, but limited to, those exemplified herein.

In an additional embodiment, the invention provides a non-naturally occurring microbial organism having a propylene pathway, wherein the non-naturally occurring microbial organism comprises at least one exogenous nucleic acid encoding an enzyme or protein that converts a substrate to a product selected from the group consisting of 2-ketoglutarate to 3-methyl-2-ketoglutarate, 3-methyl-2-ketoglutarate to propylene, pyruvate to 4-hydroxy-4-methyl-2-ketoglutarate, 4-hydroxy-4-methyl-2-ketoglutarate to 4-methylene-2-ketoglutarate, 4-methylene-2-ketoglutarate to 4-methyl-2-ketoglutarate, 4-hydroxy-4-methyl-2-ketoglutarate to 4-methyl-2-ketoglutaconate, 4-methyl-2-ketoglutaconate to 4-methyl-2-ketoglutarate or 4-methyl-2-ketoglutarate to propylene. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a propylene pathway, such as that shown in FIGS. 2-5.

While generally described herein as a microbial organism that contains a propylene pathway, it is understood that the invention additionally provides a non-naturally occurring microbial organism comprising at least one exogenous nucleic acid encoding a propylene pathway enzyme expressed in a sufficient amount to produce an intermediate of a propylene pathway. For example, as disclosed herein, a propylene pathway is exemplified in FIGS. 2-5. Therefore, in addition to a microbial organism containing a propylene pathway that produces propylene, the invention additionally provides a non-naturally occurring microbial organism comprising at least one exogenous nucleic acid encoding a propylene pathway enzyme, where the microbial organism produces a propylene pathway intermediate, for example, 3-methyleketoglutarate, 4-hydroxy-4-methyl-2-ketoglutarate, 4-methylene-2-ketoglutarate, 4-methyl-2-ketoglutaconate, or 4-methyl-2-ketoglutarate.

It is understood that any of the pathways disclosed herein, as described in the Examples and exemplified in the Figures, including the pathways of FIGS. 2-5, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a propylene pathway intermediate can be utilized to produce the intermediate as a desired product.

This invention is also directed, in part to engineered biosynthetic pathways to improve carbon flux through a central metabolism intermediate en route to propylene. The present invention provides non-naturally occurring microbial organisms having one or more exogenous genes encoding enzymes that can catalyze various enzymatic transformations en route to propylene. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of propylene by (i) enhancing carbon fixation via the reductive TCA cycle, and/or (ii) accessing additional reducing equivalents from gaseous carbon sources and/or syngas components such as CO, $CO_2$, and/or $H_2$. In addition to syngas, other sources of such gases include, but are not limted to, the atmosphere, either as found in nature or generated.

Figure 6:
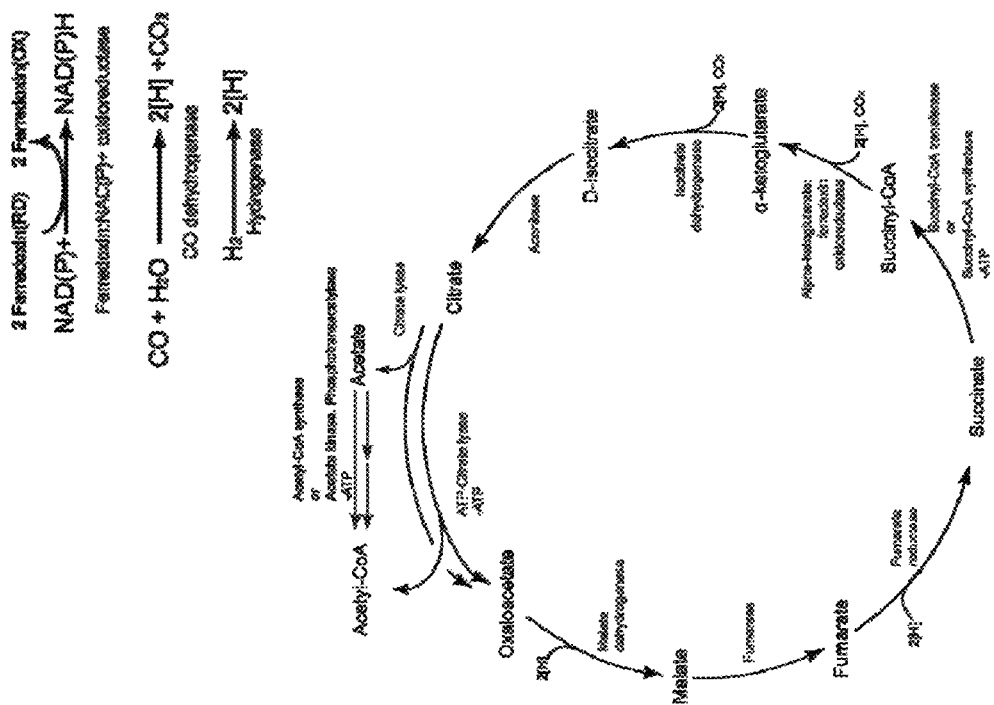
FIG. 6 shows the reverse TCA cycle for fixation of $CO_2$ on carbohydrates as substrates. The enzymatic transformations are carried out by the enzymes as shown.

The $CO_2$-fixing reductive tricarboxylic acid (RTCA) cycle is an endergenic anabolic pathway of $CO_2$ assimilation which uses reducing equivalents and ATP (FIG. 6). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes, can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, and reduced flavodoxins. The reducing equivalents, particularly NADH, NADPH, reduced ferredoxin and thioredoxins, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186: 2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate: ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase or by conversion of pyruvate to malate by malic enzyme.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the NAD(P)$^+$ dependent decarboxylation of alpha-ketoglutarate by the alpha-ketoglutarate dehydrogenase complex. The reverse reaction is catalyzed by alpha-ketoglutarate:ferredoxin oxidoreductase.

Figure 7:
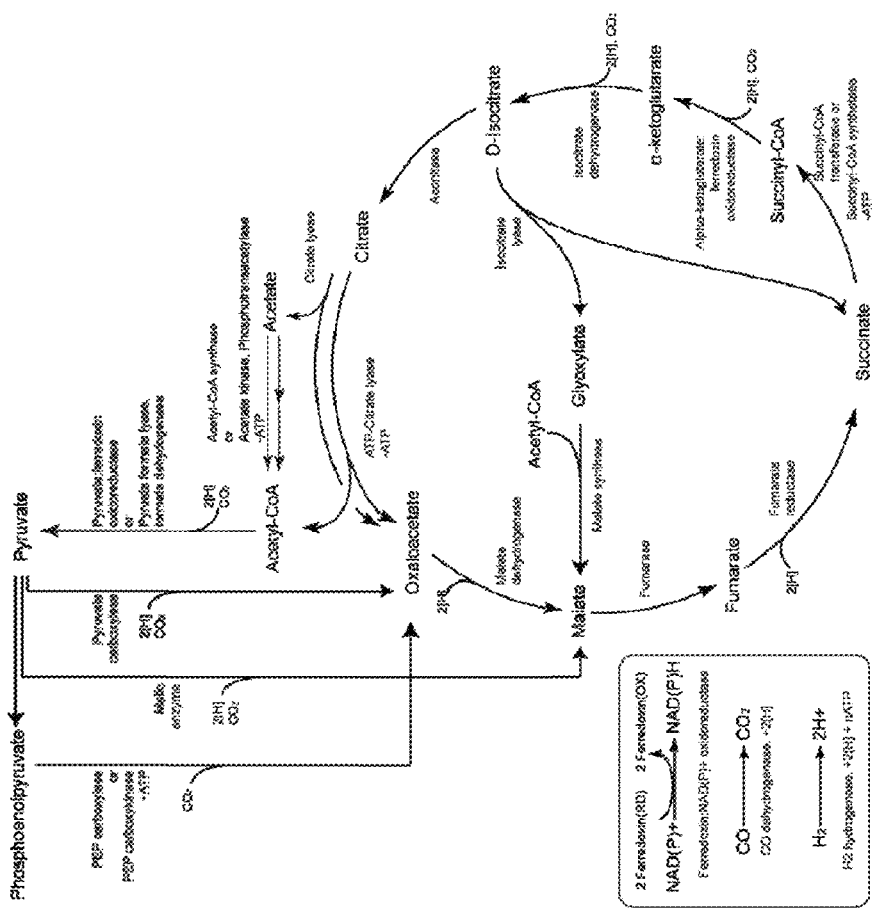
FIG. 7 shows the pathway for the reverse TCA cycle coupled with carbon monoxide dehydrogenase and hydrogenase for the conversion of syngas to acetyl-CoA.
Figure 8:
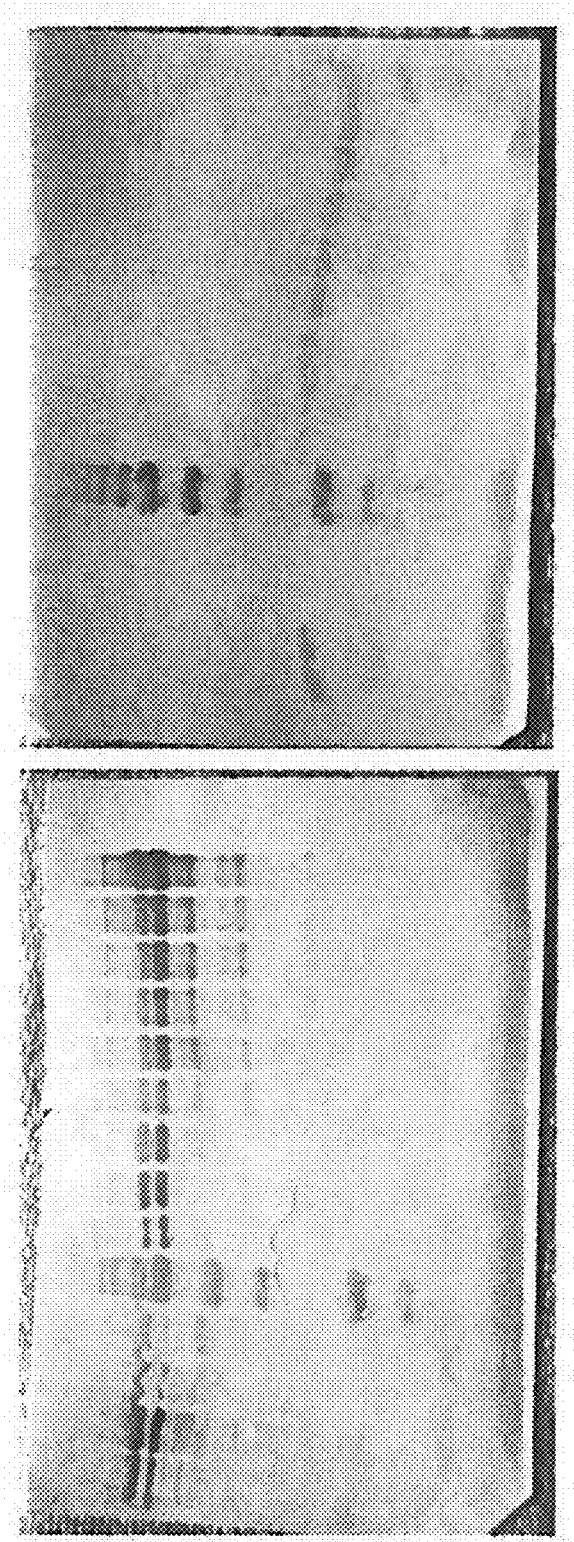
FIG. 8 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H: ferredoxin oxidoreductase, carbon monoxide dehydrogenase, hydrogenase, and ferredoxin (see FIG. 7). Enzyme enzymes and the corresponding genes required for these activities are described herein.

Carbon from syngas or other gaseous carbon sources can be fixed via the reverse TCA cycle and components thereof. Specifically, the combination of certain carbon gas-utilization pathway components with the pathways for formation of propylene from acetyl-CoA results in high yields of these products by providing an efficient mechanism for fixing the carbon present in carbon dioxide, fed exogenously or produced endogenously from CO, into acetyl-CoA.

In some embodiments, a propylene pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having an propylene pathway includes at least one exogenous nucleic acid encoding a reductive TCA pathway enzyme. The at least one exogenous nucleic acid is selected from an ATP-citrate lyase, citrate lyase, a fumarate reductase, isocitrate dehydrogenase, aconitase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a propylene pathway also comprising at least one exogenous nucleic acid encoding a reductive TCA pathway enzyme. The at least one exogenous nucleic acid is selected from an ATP-citrate lyase, citrate lyase, a fumarate reductase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having an propylene pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, a pyruvate:ferredoxin oxidoreductase, isocitrate dehydrogenase, aconitase, and an alpha-ketoglutarate:ferredoxin oxidoreductase.

In some embodiments a non-naturally occurring microbial organism having an propylene pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce propylene.

In some embodiments, the non-naturally occurring microbial organism having an propylene pathway includes two exogenous nucleic acids, each encoding a reductive TCA pathway enzyme. In some embodiments, the non-naturally occurring microbial organism having an propylene pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, the non-naturally occurring microbial organism includes three exogenous nucleic acids encoding a citrate lyase, a fumarate reductase, and an alpha-ketoglutarate:ferredoxin oxidoreductase. In some embodiments, the non-naturally occurring microbial organism includes four exogenous nucleic acids encoding a pyruvate:ferredoxin oxidoreductase; a phosphoenolpyruvate carboxylase or a phosphoenolpyruvate carboxykinase, a CO dehydrogenase; and an $H_2$ hydrogenase. In some embodiments, the non-naturally occurring microbial organism includes two exogenous nucleic acids encoding a CO dehydrogenase and an $H_2$ hydrogenase.

In some embodiments, the non-naturally occurring microbial organisms having an propylene pathway further include an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism having an propylene pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having an propylene pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having an propylene pathway utilizes hydrogen for reducing equivalents. In some embodiments, the non-naturally occurring microbial organism having an propylene pathway utilizes CO for reducing equivalents. In some embodiments, the non-naturally occurring microbial organism having an propylene pathway utilizes combinations of CO and hydrogen for reducing equivalents.

In some embodiments, the non-naturally occurring microbial organism having an propylene pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having an propylene pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having an propylene pathway further includes at least one exogenous nucleic acid encoding a citrate lyase, an ATP-citrate lyase, a citryl-CoA synthetase, a citryl-CoA lyase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, and a ferredoxin.

It is understood by those skilled in the art that the above-described pathways for increasing product yield can be combined with any of the pathways disclosed herein, including those pathways depicted in the figures. One skilled in the art will understand that, depending on the pathway to a desired product and the precursors and intermediates of that pathway, a particular pathway for improving product yield, as discussed herein above and in the examples, or combination of such pathways, can be used in combination with a pathway to a desired product to increase the yield of that product or a pathway intermediate.

In one embodiment, the invention provides a non-naturally occurring microbial organism, comprising a microbial organism having a propylene pathway. The propylene pathway can be any of the propylene pathways disclosed herein, including the figures. In a particular embodiment, the microbial organism comprises at least one exogenous nucleic acid encoding a propylene pathway enzyme expressed in a sufficient amount to produce propylene; the non-naturally occurring microbial organism further comprising: (i) a reductive TCA pathway comprising at least one exogenous nucleic acid encoding a reductive TCA pathway enzyme, wherein the at least one exogenous nucleic acid is selected from an ATP-citrate lyase, citrate lyase, a citryl-CoA synthetase, a citryl-CoA lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. The propylene pathway can be selected from (a) a propylene forming enzyme and a 2-ketoglutarate methyltransferase; and (b) a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methyl-2-ketoglutaconate reductase.

In another embodiment, a microbial organism comprising (i) can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In yet another embodiment, a microbial organism comprising (ii) can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In a particular embodiment the microbial organism can comprise (a) two exogenous nucleic acids encoding a propylene forming enzyme and a 2-ketoglutarate methyltransferase; or (b) four exogenous nucleic acids encoding a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methyl-2-ketoglutaconate reductase. The invention additionally provides methods of producing propylene using such propylene producing organisms.

In some embodiments, the carbon feedstock and other cellular uptake sources such as phosphate, ammonia, sulfate, chloride and other halogens can be chosen to alter the isotopic distribution of the atoms present in propylene or any propylene pathway intermediate. The various carbon feedstock and other uptake sources enumerated above will be referred to herein, collectively, as "uptake sources." Uptake sources can provide isotopic enrichment for any atom present in the product propylene or propylene pathway intermediate including any propylene impurities generated in diverging away from the pathway at any point. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{-12}$ (Karlen et al., *Arkiv Geofisik*, 4:465-471 (1968)). The standard calculations take into account the differential uptake of one istope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides propylene or a propylene intermediate that has a carbon-12, carbon-13, and carbon-14 ratio that reflects an atmospheric carbon, also referred to as environmental carbon, uptake source. For example, in some aspects the propylene or a propylene intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides propylene or a propylene intermediate that has a carbon-12, carbon-13, and carbon-14 ratio that reflects petroleum-based carbon uptake source. In this aspect, the propylene or a propylene intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides propylene or a propylene intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced propylene or propylene intermediate as disclosed herein, and to the products derived therefrom, wherein the propylene or a propylene intermediate has a carbon-12, carbon-13, and carbon-14 isotope ratio of about the same value as the $CO_2$ that occurs in the environment. For example, in some aspects the invention provides bioderived propylene or a bioderived propylene intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived propylene or a bioderived propylene intermediate as disclosed herein, wherein the bioderived product is chemically modified to generate a final product. Methods of chemically modifying a bioderived product of propylene, or an intermediate thereof, to generate a desired product are well known to those skilled in the art, as described herein. The invention further provides polypropylene, acrylic acid, butanol, butanediol, acrylonitrile, propylene oxide, isopropanol, cumene, plastic, fiber, synthetic rubber, aerosol propellant or aerosol component having a carbon-12 versus carbon-13 versus carbon-14 isotope ratio of about the same value as the $CO_2$ that occurs in the environment, wherein the polypropylene, acrylic acid, butanol, butanediol, acrylonitrile, propylene oxide, isopropanol, cumene, plastic, fiber, synthetic rubber, aerosol propellant or aerosol component are generated directly from or in combination with bioderived propylene or a bioderived propylene intermediate as disclosed herein.

Propylene is a chemical used in commercial and industrial applications. Non-limiting examples of such applications include production of polymers, polymer intermediates and chemicals. Moreover, propylene is also used in the production of a wide range of products including polypropylene, acrylic acid, butanol, butanediol, acrylonitrile, propylene oxide, isopropanol and cumene. The propylene derivative, polypropylene, is also used in the production of plastics, such as injection moulding, fibers, such as carpets, synthetic rubber and as a propellant or component in aerosols. Accordingly, in some embodiments, the invention provides biobased polypropylene, acrylic acid, butanol, butanediol, acrylonitrile, propylene oxide, isopropanol, cumene, plastic, fiber, synthetic rubber, aerosol propellant or aerosol component comprising one or more bioderived propylene or bioderived propylene intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides polypropylene, acrylic acid, butanol, butanediol, acrylonitrile, propylene oxide, isopropanol, cumene, plastic, fiber, synthetic rubber, aerosol propellant or aerosol component comprising bioderived propylene or bioderived propylene intermediate, wherein the bioderived propylene or bioderived propylene intermediate includes all or part of the propylene or propylene intermediate used in the production of polypropylene, acrylic acid, butanol, butanediol, acrylonitrile, propylene oxide, isopropanol, cumene, plastic, fiber, synthetic rubber, aerosol propellant or aerosol component. Thus, in some aspects, the invention provides a biobased polypropylene, acrylic acid, butanol, butanediol, acrylonitrile, propylene oxide, isopropanol, cumene, plastic, fiber, synthetic rubber, aerosol propellant or aerosol component comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived propylene or bioderived propylene intermediate as disclosed herein. Additionally, in some aspects, the invention provides a biobased polypropylene, acrylic acid, butanol, butanediol, acrylonitrile, propylene oxide, isopropanol, cumene, plastic, fiber, synthetic rubber, aerosol propellant or aerosol component wherein the propylene or propylene intermediate used in its production is a combination of bioderived and petroleum derived propylene or propylene intermediate. For example, a biobased polypropylene, acrylic acid, butanol, butanediol, acrylonitrile, propylene oxide, isopropanol, cumene, plastic, fiber, synthetic rubber, aerosol propellant or aerosol component can be produced using 50% bioderived propylene and 50% petroleum derived propylene or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polypropylene, acrylic acid, butanol, butanediol, acrylonitrile, propylene oxide, isopropanol, cumene, plastic, fiber, synthetic rubber, aerosol propellant or aerosol component using the bioderived propylene or bioderived propylene intermediate of the invention are well known in the art.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the intermediates 3-methyl-2-ketoglutarate, 4-hydroxy-4-methyl-2-ketoglutarate, 4-methyl-2-ketoglutaconate, 4-methylene-2-ketoglutarate, 4-methyl-2-ketoglutarate, 4-methyl-2-oxopentanoate, 3-methylglutaconate, 3-methyl-2-hydroxyglutarate, 2-aminoadipate semialdehyde, 2-aminoadipate, 2-oxoadipate, and 4-methyl-2-aminoglutarate, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl-3-methyl-2-ketoglutarate, methyl-4-hydroxy-4-methyl-2-ketoglutarate, methyl-4-methyl-2-ketoglutaconate, methyl-4-methylene-2-ketoglutarate, methyl-4-methyl-2-ketoglutarate, methyl-4-methyl-2-oxopentanoate, methyl-3-methylglutaconate, methyl-3-methyl-2-hydroxyglutarate, methyl-2-aminoadipate semialdehyde, methyl-2-aminoadipate, methyl-2-oxoadipate, methyl-4-methyl-2-aminoglutarate, ethyl-3-methyl-2-ketoglutarate, ethyl-4-hydroxy-4-methyl-2-ketoglutarate, ethyl-4-methyl-2-ketoglutaconate, ethyl-4-methylene-2-ketoglutarate, ethyl-4-methyl-2-ketoglutarate, ethyl-4-methyl-2-oxopentanoate, ethyl-3-methylglutaconate, ethyl-3-methyl-2-hydroxyglutarate, ethyl-2-aminoadipate semialdehyde, ethyl-2-aminoadipate, ethyl-2-oxoadipate, and ethyl-4-methyl-2-aminoglutarate, n-propyl-3-methyl-2-ketoglutarate, n-propyl-4-hydroxy-4-methyl-2-ketoglutarate, n-propyl-4-methyl-2-ketoglutaconate, n-propyl-4-methylene-2-ketoglutarate, n-propyl-4-methyl-2-ketoglutarate, n-propyl-4-methyl-2-oxopentanoate, n-propyl-3-methylglutaconate, n-propyl-3-methyl-2-hydroxyglutarate, n-propyl-2-aminoadipate semialdehyde, n-propyl-2-aminoadipate, n-propyl-2-oxoadipate, and n-propyl-4-methyl-2-aminoglutarate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more propylene biosynthetic pathways. Depending on the host microbial organism chosen for biosynthesis, nucleic acids for some or all of a particular propylene biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve propylene biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as propylene.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the propylene biosynthetic pathway constituents of a selected host microbial organism, the non-naturally occurring microbial organisms of the invention will include at least one exogenously expressed propylene pathway-encoding nucleic acid and up to all encoding nucleic acids for one or more propylene biosynthetic pathways. For example, propylene biosynthesis can be established in a host deficient in a pathway enzyme or protein through exogenous expression of the corresponding encoding nucleic acid. In a host deficient in all enzymes or proteins of a propylene pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of propylene can be included, such as a 2-ketoglutarate methyltransferase and a propylene forming enzyme, or alternatively, a 4-hydroxy-4-methyl-2-ketoglutarate aldolase, a 4-hydroxy-4-methyl-2-ketoglutarate dehydratase II, a 4-methylene-2-ketoglutarate reductase and a propylene forming enzyme, or alternatively a 4-hydroxy-4-methyl-2-ketoglutarate aldolase, a 4-hydroxy-4-methyl-2-ketoglutarate dehydratase I, a 4-methyl-2-ketoglutaconate reductase and a propylene forming enzyme.

Given the teachings and guidance provided herein, those skilled in the art will understand that the number of encoding nucleic acids to introduce in an expressible form will, at least, parallel the propylene pathway deficiencies of the selected host microbial organism. Therefore, a non-naturally occurring microbial organism of the invention can have one, two, three, or four, up to all nucleic acids encoding the enzymes or proteins constituting a propylene biosynthetic pathway disclosed herein. In some embodiments, the non-naturally occurring microbial organisms also can include other genetic modifications that facilitate or optimize propylene biosynthesis or that confer other useful functions onto the host microbial organism. One such other functionality can include, for example, augmentation of the synthesis of one or more of the propylene pathway precursors such as 2-ketoglutarate or pyruvate.

Generally, a host microbial organism is selected such that it produces the precursor of a propylene pathway, either as a naturally produced molecule or as an engineered product that either provides de novo production of a desired precursor or increased production of a precursor naturally produced by the host microbial organism. For example, pyruvate and 2-ketoglutarate are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a propylene pathway.

In some embodiments, a non-naturally occurring microbial organism of the invention is generated from a host that contains the enzymatic capability to synthesize propylene. In this specific embodiment it can be useful to increase the synthesis or accumulation of a propylene pathway product to, for example, drive propylene pathway reactions toward propylene production. Increased synthesis or accumulation can be accomplished by, for example, overexpression of nucleic acids encoding one or more of the above-described propylene pathway enzymes or proteins. Overexpression of the enzyme or enzymes and/or protein or proteins of the propylene pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing propylene, through overexpression of one, two, three, or four, that is, up to all nucleic acids encoding propylene biosynthetic pathway enzymes or proteins. In addition, a non-naturally occurring organism can be generated by mutagenesis of an endogenous gene that results in an increase in activity of an enzyme in the propylene biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a propylene biosynthetic pathway onto the microbial organism. Alternatively, encoding nucleic acids can be introduced to produce an intermediate microbial organism having the biosynthetic capability to catalyze some of the required reactions to confer propylene biosynthetic capability. For example, a non-naturally occurring microbial organism having a propylene biosynthetic pathway can comprise at least two exogenous nucleic acids encoding desired enzymes or proteins, such as the combination of a 2-ketoglutarate methyltransferase and a propylene forming enzyme, or alternatively a 4-hydroxy-4-methyl-2-ketoglutarate dehydratase II and a 4-methylene-2-ketoglutarate reductase, or alternatively a 4-hydroxy-4-methyl-2-ketoglutarate aldolase and a propylene forming enzyme, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a 4-hydroxy-4-methyl-2-ketoglutarate aldolase, a 4-hydroxy-4-methyl-2-ketoglutarate dehydratase II and a 4-methylene-2-ketoglutarate reductase, or alternatively a 4-hydroxy-4-methyl-2-ketoglutarate dehydratase II, a 4-methylene-2-ketoglutarate reductase and a propylene forming enzyme, or alternatively a 4-hydroxy-4-methyl-2-ketoglutarate aldolase, a 4-hydroxy-4-methyl-2-ketoglutarate dehydratase I and a 4-methyl-2-ketoglutaconate reductase, or alternatively a 4-hydroxy-4-methyl-2-ketoglutarate dehydratase I, a 4-methyl-2-ketoglutaconate reductase and a propylene forming enzyme and so forth, as desired, so long as the combination of enzymes and/or proteins of the desired biosynthetic pathway results in production of the corresponding desired product. Similarly, any combination of four, a 4-hydroxy-4-methyl-2-ketoglutarate aldolase, a 4-hydroxy-4-methyl-2-ketoglutarate dehydratase II, a 4-methylene-2-ketoglutarate reductase and a propylene forming enzyme or alternatively a 4-hydroxy-4-methyl-2-ketoglutarate aldolase, a 4-hydroxy-4-methyl-2-ketoglutarate dehydratase I, a 4-methyl-2-ketoglutaconate reductase and a propylene forming enzyme, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of propylene as described herein, the non-naturally occurring microbial organisms and methods of the invention also can be utilized in various combinations with each other and with other microbial organisms and methods well known in the art to achieve product biosynthesis by other routes. For example, one alternative to produce propylene other than use of the propylene producers is through addition of another microbial organism capable of converting a propylene pathway intermediate to propylene. One such procedure includes, for example, the fermentation of a microbial organism that produces a propylene pathway intermediate. The propylene pathway intermediate can then be used as a substrate for a second microbial organism that converts the propylene pathway intermediate to propylene. The propylene pathway intermediate can be added directly to another culture of the second organism or the original culture of the propylene pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, propylene. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of propylene can be accomplished by constructing a microbial organism that contains biosynthetic pathways for conversion of one pathway intermediate to another pathway intermediate or the product. Alternatively, propylene also can be biosynthetically produced from microbial organisms through co-culture or co-fermentation using two organisms in the same vessel, where the first microbial organism produces a propylene intermediate and the second microbial organism converts the intermediate to propylene.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce propylene.

Sources of encoding nucleic acids for a propylene pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Anaerotruncus colihominis* DSM 17241, *Bacteroides capillosus* ATCC 29799, *Campylobacter jejuni*, *Clostridium botulinum* A3 str, *Clostridium kluyveri*, *Clostridium tyrobutyricum*, *Comamonas estosterone*, *Corynebacterium glutamicum*, *Cupriavidus necator*, *Escherichia coli*, *Escherichia coli* C, *Escherichia coli* W, *Eubacterium barkeri*, *Klebsiella estoster*, *Methanocaldococcus jannaschii*, *Moorella thermoacetica*, *Pelotomaculum thermopropionicum*, *Pseudomonas ochraceae* NGJ1, *Pseudomonas putida* F1, *Pseudomonas reinekei* MT1, *Pseudomonas* sp. Strain B13, *Pseudomonas syringae* pv. *Glycinea*, *Pseudomonas syringae* pv. *Phaseolicola* PK2, *Pseudomonas syringae* pv. *Pisi*, *Ralstonia eutropha* JMP134, *Ralstonia solanacearum*, *Rattus norvegicus*, *Rhodococcus opacus*, *Saccharomyces cerevisiae*, *Salmonella estost*, *Sphingomonas* sp. SYK6, *Streptomyces coelicolor* A3(2), *Streptomyces fradiae*, *Streptomyces roseosporus* NRRL 11379, *Thermus thermophilus*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite propylene biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of propylene described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative propylene biosynthetic pathway exists in an unrelated species, propylene biosynthesis can be conferred onto the host species by, for example, exogenous expression of a estoste or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize propylene.

Methods for constructing and testing the expression levels of a non-naturally occurring propylene-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of propylene can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more propylene biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, the invention provides a method for producing propylene that includes culturing a non-naturally occurring microbial organism, including a microbial organism having a propylene pathway, the propylene pathway including at least one exogenous nucleic acid encoding a propylene pathway enzyme expressed in a sufficient amount to produce propylene, the propylene pathway including a 2-ketoglutarate methyltransferase or a propylene forming enzyme (see FIG. 2, steps 1-2). In one aspect, the method includes a microbial organism having a propylene pathway including a 2-ketoglutarate methyltransferase and a propylene forming enzyme (FIG. 2, steps 1 and 2).

In some embodiments, the invention provides a method for producing propylene that includes culturing a non-naturally occurring microbial organism, including a microbial organism having a propylene pathway, the propylene pathway including at least one exogenous nucleic acid encoding a propylene pathway enzyme expressed in a sufficient amount to produce propylene, the propylene pathway including a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, a 4-methyl-2-ketoglutaconate reductase or a propylene forming enzyme (see FIG. 3, steps A-F). In one aspect, the method includes a microbial organism having a propylene pathway including a 4-hydroxy-4-methyl-2-ketoglutarate aldolase, a 4-hydroxy-4-methyl-2-ketoglutarate dehydratase II, a 4-methylene-2-ketoglutarate reductase and a propylene forming enzyme (see FIG. 3, steps A, B, C and F). In one aspect, the method includes a microbial organism having a propylene pathway including a 4-hydroxy-4-methyl-2-ketoglutarate aldolase, a 4-hydroxy-4-methyl-2-ketoglutarate dehydratase I, a 4-methyl-2-ketoglutaconate reductase and a propylene forming enzyme (FIG. 3, steps A, D, E and F).

In some embodiments, the invention provides a method for producing propylene that includes culturing a non-naturally occurring microbial organism, including a microbial organism having a propylene pathway, the propylene pathway including at least one exogenous nucleic acid encoding a propylene pathway enzyme expressed in a sufficient amount to produce propylene, the propylene pathway including a leucine aminotransferase, dehydrogenase (deaminating) or oxidase; a 4-methyl-2-oxopentanoate dehydrogenase; an isovaleryl-CoA dehydrogenase; a 3-methylcrotonyl-CoA carboxylase; a 3-methylglutaconyl-CoA hydrolase, transferase or synthetase; a 3-methylglutaconate hydratase; a 3-methyl-2-hydroxyglutarate dehydrogenase; a 3-hydroxy-3-methylglutaryl-CoA dehydratase; or a 3-hydroxy-3-methylglutaryl-CoA lyase (see FIG. 4, steps A-I). In one aspect, the method includes a microbial organism having a propylene pathway including a leucine aminotransferase, dehydrogenase (deaminating) or oxidase; a 4-methyl-2-oxopentanoate dehydrogenase; a isovaleryl-CoA dehydrogenase; a 3-methylcrotonyl-CoA carboxylase; a 3-methylglutaconyl-CoA hydrolase, transferase or synthetase; a 3-methylglutaconate hydratase; a 3-methyl-2-hydroxyglutarate dehydrogenase and a propylene forming enzyme (see FIG. 4, steps A-G and FIG. 2, step 2). In one aspect, the method includes a microbial organism having a propylene pathway including a 3-methylglutaconyl-CoA hydrolase, transferase or synthetase; a 3-methylglutaconate hydratase; a 3-methyl-2-hydroxyglutarate dehydrogenase; a 3-hydroxy-3-methylglutaryl-CoA dehydratase; a 3-hydroxy-3-methylglutaryl-CoA lyase and a propylene forming enzyme (see FIG. 4, steps I, H, E-G and FIG. 2, step 2). Sources of encoding nucleic acids for a propylene pathway enzyme or protein described above are well known in the art and can be obtained from a variety of species including, but limited to, those exemplified herein.

In some embodiments, the invention provides a method for producing propylene that includes culturing a non-naturally occurring microbial organism, including a microbial organism having a propylene pathway, the propylene pathway including at least one exogenous nucleic acid encoding a propylene pathway enzyme expressed in a sufficient amount to produce propylene, the propylene pathway including a lysine 6-aminotransferase, a 6-dehydrogenase (deaminating) or 6-oxidase; an 2-aminoadipate dehydrogenase; an 2-aminoadipate mutase; a 4-methyl-2-aminoglutarate aminotransferase, dehydrogenase (deaminating) or oxidase; a 2-aminoadipate aminotransferase, dehydrogenase (deaminating) or oxidase; or a 2-oxoadipate mutase (see FIG. 5, steps A-F). In one aspect, the method includes a microbial organism having a propylene pathway including a lysine 6-aminotransferase, 6-dehydrogenase (deaminating) or 6-oxidase; an 2-aminoadipate dehydrogenase, an 2-aminoadipate mutase; a 4-methyl-2-aminoglutarate aminotransferase, dehydrogenase (deaminating) or oxidase; and a propylene forming enzyme (see FIG. 5, steps A-D, FIG. 3, step F). In one aspect, the method includes a microbial organism having a propylene pathway including a lysine 6-aminotransferase, 6-dehydrogenase (deaminating) or 6-oxidase; a 2-aminoadipate dehydrogenase; an 2-aminoadipate aminotransferase, dehydrogenase (deaminating) or oxidase; an 2-oxoadipate mutase; and a propylene forming enzyme (see FIG. 5, steps A, B, E and F, FIG. 3, step F). Sources of encoding nucleic acids for a propylene pathway enzyme or protein described above are well known in the art and can be obtained from a variety of species including, but limited to, those exemplified herein.

In some embodiments, the invention provides a method for producing propylene that includes culturing a non-naturally occurring microbial organism, including a microbial organism having at least one exogenous nucleic acid encoding a propylene pathway enzyme expressed in a sufficient amount to produce propylene; the non-naturally occurring microbial organism further comprising: (i) a reductive TCA pathway comprising at least one exogenous nucleic acid encoding a reductive TCA pathway enzyme, wherein the at least one exogenous nucleic acid is selected from an ATP-citrate lyase, citrate lyase, a citryl-CoA synthetase, a citryl-CoA lyase, a fumarate reductase, and an alpha-ketoglutarate:ferredoxin oxidoreductase; (ii) a reductive TCA pathway comprising at least one exogenous nucleic acid encoding a reductive TCA pathway enzyme, wherein the at least one exogenous nucleic acid is selected from a pyruvate:ferredoxin oxidoreductase, a phosphoenolpyruvate carboxylase, a phosphoenolpyruvate carboxykinase, a CO dehydrogenase, and an H2 hydrogenase; or (iii) at least one exogenous nucleic acid encodes an enzyme selected from a CO dehydrogenase, an H2 hydrogenase, and combinations thereof. The propylene pathway can be selected from (a) a propylene forming enzyme and a 2-ketoglutarate methyltransferase; and (b) a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methyl-2-ketoglutaconate reductase.

In another embodiment, the invention provides a method for producing propylene that includes culturing a non-naturally occurring microbial organism, including a microbial organism comprising (i) can further comprise an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof. In yet another embodiment, a microbial organism comprising (ii) can further comprise an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof. In a particular embodiment the microbial organism used in the method can comprise (a) two exogenous nucleic acids encoding a propylene forming enzyme and a 2-ketoglutarate methyltransferase; or (b) four exogenous nucleic acids encoding a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methyl-2-ketoglutaconate reductase.

Suitable purification and/or assays to test for the production of propylene can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For typical Assay Methods, see Manual on Hydrocarbon Analysis (ASTM Manula Series, A. W. Drews, ed., $6^{th}$ edition, 1998, American Society for Testing and Materials, Baltimore, Md.

The propylene can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the propylene producers can be cultured for the biosynthetic production of propylene.

For the production of propylene, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of propylene.

In addition to renewable feedstocks such as those exemplified above, the propylene microbial organisms of the invention also can be modified for growth on syngas as its source of carbon. In this specific embodiment, one or more proteins or enzymes are expressed in the propylene producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

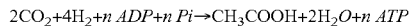

$$2CO_2 + 4H_2 + n\ ADP + n\ Pi \rightarrow CH_3COOH + 2H_2O + n\ ATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a propylene pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD (P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the propylene precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a p-toluate, terephthalate or (2-hydroxy-3-methyl-4-oxobutoxy)phosphonate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, propylene and any of the intermediate metabolites in the propylene pathway. All that is required is to engineer in one or more of the required enzyme or protein activities to achieve biosynthesis of the desired compound or intermediate including, for example, inclusion of some or all of the propylene biosynthetic pathways. Accordingly, the invention provides a non-naturally occurring microbial organism that produces and/or secretes propylene when grown on a carbohydrate or other carbon source and produces and/or secretes any of the intermediate metabolites shown in the propylene pathway when grown on a carbohydrate or other carbon source. The propylene producing microbial organisms of the invention can initiate synthesis from an intermediate, for example, 3-methyle-ketoglutarate, 4-hydroxy-4-methyl-2-ketoglutarate, 4-methylene-2-ketoglutarate, 4-methyl-2-ketoglutaconate, or 4-methyl-2-ketoglutarate.

The non-naturally occurring microbial organisms of the invention are constructed using methods well known in the art as exemplified herein to exogenously express at least one nucleic acid encoding a propylene pathway enzyme or protein in sufficient amounts to produce propylene. It is understood that the microbial organisms of the invention are cultured under conditions sufficient to produce propylene. Following the teachings and guidance provided herein, the non-naturally occurring microbial organisms of the invention can achieve biosynthesis of propylene resulting in intracellular concentrations between about 0.001-2000 mM or more. Generally, the intracellular concentration of propylene is between about 3-1500 mM, particularly between about 5-1250 mM and more particularly between about 8-1000 mM, including about 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the propylene producers can synthesize propylene at intracellular concentrations of 5-10 mM or more as well as all other concentrations exemplified herein. It is understood that, even though the above description refers to intracellular concentrations, propylene producing microbial organisms can produce propylene intracellularly and/or secrete the product into the culture medium.

In addition to the culturing and fermentation conditions disclosed herein, growth condition for achieving biosynthesis of propylene can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of propylene includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of propylene. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of propylene. Generally, and as with non-continuous culture procedures, the continuous and/or near-continuous production of propylene will include culturing a non-naturally occurring propylene producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of propylene can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the propylene producers of the invention for continuous production of substantial quantities of propylene, the propylene producers also can be, for example, simultaneously subjected to chemical synthesis procedures to convert the product to other compounds or the product can be separated from the fermentation culture and sequentially subjected to chemical or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of propylene.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SIMPHENY software. This computational method and system is described in, for example, U.S. publication 2003/0233218, filed Jun. 14, 2002, and in International Patent Application No. PCT/US03/18838, filed Jun. 13, 2003. SIMPHENY software is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SIMPHENY software and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797(2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SIMPHENY software.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SIMPHENY software. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a propylene pathway can be introduced into a host organism. In some cases, it can be desirable to modify an activity of a propylene pathway enzyme or protein to increase production of propylene. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, $>10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

Described below in more detail are exemplary methods that have been developed for the mutagenesis and diversification of genes to target desired properties of specific enzymes. Such methods are well known to those skilled in the art. Any of these can be used to alter and/or optimize the activity of a propylene pathway enzyme or protein.

EpPCR (Pritchard et al., *J Theor. Biol.* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful to screen a larger number of potential variants having a desired activity. A high number of mutants can be generated by EpPCR, so a high-throughput screening assay or a selection method, for example, using robotics, is useful to identify those with desirable characteristics.

Error-prone Rolling Circle Amplification (epRCA) (Fujii et al., *Nucleic Acids Res.* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a commercially available kit.

DNA or Family Shuffling (Stemmer, *Proc Natl Acad Sci USA* 91:10747-10751 (1994)); and Stemmer, *Nature* 370: 389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations.

Staggered Extension (StEP) (Zhao et al., *Nat. Biotechnol.* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template (Shao et al., *Nucleic Acids Res* 26:681-683 (1998)). Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)). The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol.* 19:354-359 (2001)) employs Dnase I fragmentation and size fractionation of single stranded DNA (ssDNA). Homologous fragments are hybridized in the absence of polymerase to a complementary ssDNA scaffold. Any overlapping unhybridized fragment ends are trimmed down by an exonuclease. Gaps between fragments are filled in and then ligated to give a pool of full-length diverse strands hybridized to the scaffold, which contains U to preclude amplification. The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled estoste. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates (Lee et al., *J. Molec. Catalysis* 26:119-129 (2003)). No DNA endonucleases are used. Unidirectional ssDNA is made by DNA polymerase with random primers or serial deletion with exonuclease. Unidirectional ssDNA are only templates and not primers. Random priming and exonucleases do not introduce sequence bias as true of enzymatic cleavage of DNA shuffling/RACHITT. RETT can be easier to optimize than StEP because it uses normal PCR conditions instead of very short extensions. Recombination occurs as a component of the PCR steps, that is, no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol.* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)). Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations (Lutz et al., *Nucleic Acids Res* 29:E16 (2001)). Relative to ITCHY, THIO-ITCHY can be easier to optimize, provide more reproducibility, and adjustability.

SCRATCHY combines two methods for recombining genes, ITCHY and DNA shuffling (Lutz et al., *Proc. Natl. Acad. Sci. USA* 98:11248-11253 (2001)). SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations are made via epPCR followed by screening/selection for those retaining usable activity (Bergquist et al., *Biomol. Eng.* 22:63-72 (2005)). Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates a pool of random length fragments using random incorporation of a phosphothioate nucleotide and cleavage; this pool is used as a template to 2) extend in the presence of "universal" bases such as inosine; 3) replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)). Using this technique it can be possible to generate a large library of mutants within 2 to 3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny (Ness et al., *Nat. Biotechnol.* 20:1251-1255 (2002)). In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation (Muller et al., *Nucleic Acids Res.* 33:e117 (2005)). The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC), a linker is used to facilitate fusion between two distantly related or unrelated genes. Nuclease treatment is used to generate a range of chimeras between the two genes. These fusions result in libraries of single-crossover hybrids (Sieber et al., *Nat. Biotechnol.* 19:456-460 (2001)). This produces a limited type of shuffling and a separate process is required for mutagenesis. In addition, since no homology is needed, this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations (Kretz et al., *Methods Enzymol.* 388:3-11 (2004)). Primers carrying the mutation of interest, anneal to the same sequence on opposite strands of DNA. The mutation is typically in the middle of the primer and flanked on each side by approximately 20 nucleotides of correct sequence. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (that is, one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The usefulness of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations (Reidhaar-Olson et al. *Methods Enzymol.* 208: 564-586 (1991); and Reidhaar-Olson et al. *Science* 241:53-57 (1988)). Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) use of epPCR at high mutation rate to 2) identify hot spots and hot regions and then 3) extension by CMCM to cover a defined region of protein sequence space (Reetz et al., *Angew. Chem. Int. Ed Engl.* 40:3589-3591 (2001)). As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique, conditional ts mutator plasmids allow increases of 20 to 4000-X in random and natural mutation frequency during selection and block accumulation of deleterious mutations when selection is not required (Selifonova et al., *Appl. Environ. Microbiol.* 67:3645-3649 (2001)). This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frameshift mutations occur. In order for effective use, the mutator plasmid should be removed once the desired phenotype is achieved; this is accomplished through a temperature sensitive (ts) origin of replication, which allows for plasmid curing at 41° C. It should be noted that mutator strains have been explored for quite some time (see Low et al., *J. Mol. Biol.* 260:359-3680 (1996)). In this technique, very high spontaneous mutation rates are observed. The conditional property minimizes non-desired background mutations. This technology could be combined with adaptive evolution to enhance mutagenesis rates and more rapidly achieve desired phenotypes.

Look-Through Mutagenesis (LTM) is a multidimensional mutagenesis method that assesses and optimizes combinatorial mutations of selected amino acids (Rajpal et al., *Proc. Natl. Acad. Sci. USA* 102:8466-8471 (2005)). Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to create a large library of chimeras (multiple mutations) of a single gene (Tunable GENEREASSEMBLY (TGR) Combinatorial Library Technology supplied by Verenium Corporation). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, for example, codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics (Hayes et al., *Proc. Natl. Acad. Sci. USA* 99:15926-15931 (2002)). This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) using knowledge of structure/function to choose a likely site for enzyme improvement; 2) performing saturation mutagenesis at chosen site using a mutagenesis method such as Stratagene QuikChange (Stratagene; San Diego Calif.); 3) screening/selecting for desired properties; and 4) using improved clone(s), start over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)). This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE I

Pathways for Producing Propylene from
2-Ketoglutarate or Pyruvate

Figure 1:
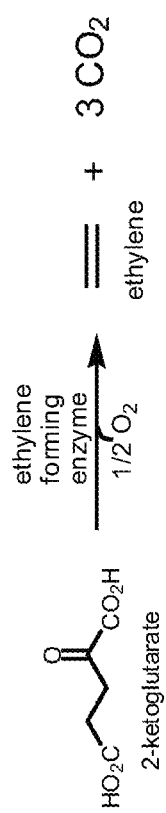
FIG. 1 shows the conversion of 2-ketoglutarate to ethylene and carbon dioxide by an ethylene forming enzyme.

Disclosed herein are novel processes for the direct production of propylene using engineered non-natural microorganisms that possess the enzymes necessary for conversion of common metabolites into the three carbon alkene, propylene. Direct production of propylene entails use of the well-known ethylene forming enzyme (EFE), which has been isolated and characterized from, for example, pathovars of the plant pathogen *Pseudomonas syringae* and shown to convert 2-ketoglutarate into ethylene and carbon dioxide (FIG. 1). The EFE enzyme or a variant of EFE is used for conversion of 3-methyl-2-ketoglutarate or 4-methyl-2-ketoglutarate into propylene and carbon dioxide in a manner analogous to the conversion of 2-ketoglutarate (step 2 of FIG. 2 and step F of FIG. 3). Thus we refer this enzyme herein as propylene forming enzyme (PFE). The intermediate 3-methyl-2-ketoglutarate can be formed directly from 2-ketoglutarate through an S-adenosylmethionine-dependent methyltransferase enzyme such as that encoded by, for example, the gene glmT in *Streptomyces frudiae* and other organisms (step 1 of FIG. 2). Alternatively, it can be formed from leucine or acetoacetate and acetyl-CoA as depicted in FIG. 4. The intermediate 4-methyl-2-oxo-glutarate can be formed through aldolase-catalyzed transformation of pyruvate to 4-hydroxy-4-methyl-2- ketoglutarate, followed by dehydration with the enzyme or variant of malate dehydratase and subsequent reduction with an enoate reductase or with an enzyme or variant of fumarate reductase (steps A-E of FIG. 3). Alternatively, it can be formed from lysine depicted in FIG. 5. Enzyme candidates for steps 1 and 2 of FIG. 2 and steps A-F of FIG. 3 are provided below.

Step 1 of FIG. 2 depicts 2-ketoglutarate methyltransferase which catalyzes the methylation of 2-ketoglutarate to form 3-methyl-2-ketoglutarate. Such activity can be obtained using enzymes encoded by glmT from *Streptomyces coelicolor*, dptI from *Streptomyces roseosporus*, and lptI from *Streptomyces fradiae* (Mahlert et al., *J. Am. Chem. Soc.*, 2007, 129 (39), 12011-12018).

| Gene | GenBank Accession No. | GI Number | Organism |
|---|---|---|---|
| glmT | NP_627429.1 | 21221650 | *Streptomyces coelicolor* A3(2) |
| dptI | ZP_04706744.1 | 239986080 | *Streptomyces roseosporus* NRRL 11379 |
| lptI | AAZ23087.1 | 71068232 | *Streptomyces fradiae* |

Several candidate genes are likely to naturally exhibit PFE activity on either 3-methyl-2-ketoglutarate (step 2, FIG. 2) or 4-methyl-2-ketoglutarate (step F, FIG. 3). If not, they can be engineered to exhibit PFE activity on these substrates. Candidate genes include EFEs from various strains of *Pseudomonas syringae* and *Ralstonia solanacearum* (Fukuda et al., Biochem Biophys Res Comm, 1992, 188 (2), 826-832; Tao et al., Appl Microbiol Biotechnol, 2008, 80(4):573-8; Chen et al., Int J of Biol Sci, 2010, 6(1):96-106; Weingart et al., Phytopathology, 1999, 89:360-365).

| Gene | GenBank Accession No. | GI Number | Organism |
|---|---|---|---|
| Efe | BAA02477.1 | 216878 | *Pseudomonas syringae* pv. Phaseolicola PK2 |
| Efe | AAD16443.1 | 4323603 | *Pseudomonas syringae* pv. *Pisi* |
| Efe | Q7BS32.1 | 50897474 | *Pseudomonas syringae* pv. Glycinea |
| Efe | CAD18680.1 | 17432003 | *Ralstonia solanacearum* |

Step A of FIG. 3 depicts 4-hydroxy-4-methyl-2-ketoglutarate aldolase which catalyzes the condensation of two pyruvate molecules to form 4-hydroxy-4-methyl-2-ketoglutarate. Genes from the following organisms encoded enzymes that catalyze 4-hydroxy-4-methyl-2-ketoglutarate aldolase: *Pseudomonas ochraceae* NGJ1 (Maruyama et al., Biosci Biotechnol Biochem, 2001, 65(12):2701-2709), *Pseudomonas putida* (Dagley, Methods Enzymol, 1982, 90:272-276), and *Pseudomonas estosterone* (or *Comamonas estosterone*) (Providenti et al., Microbiology, 2001 147 (Pt 8), 2157-2167), and *Arachis hypogaea*.

| Gene | GenBank Accession No. | GI Number | Organism |
|---|---|---|---|
| proA | BAB21456.3 | 13094205 | *Pseudomonas ochraceae* NGJ1 |
| Pput_1361 | ABQ77519.1 | 148510659 | *Pseudomonas putida* F1 |
| Pput_3204 | ABQ79330.1 | 148512470 | *Pseudomonas putida* F1 |
| CtCNB1_2744 | YP_003278786.1 | 264678879 | *Comamonas testosteroni* |

Step D of FIG. 3 depicts 4-hydroxy-4-methyl-2-ketoglutarate dehydratase I which dehydrates 4-hydroxy-4-methyl-2-ketoglutarate to form 4-methyl-2-ketoglutaconate. Step B of FIG. 3 depicts 4-hydroxy-4-methyl-2-ketoglutarate dehydratase II which dehydrates 4-hydroxy-4-methyl-2-ketoglutarate to form 4-methylene-2-ketoglutarate. Various classes of dehydratases can be applied to catalyze these transformations. Specific examples are provided below and several additional dehydratase enzymes in the EC 4.2.1 can be alternatively utilized.

For example, one enzyme that catalyzes a similar transformation is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J. Bacteriol.* 189:4391-4400 (2007)). This enzyme activity was also detected in *Clostridium tetanomorphum, Morganella morganii, Citrobacter amalonaticus* where it is thought to participate in glutamate degradation (Kato and Asano *Arch. Microbiol.* 168:457-463 (1997)). The *M. jannaschii* protein sequence does not bear significant homology to genes in these organisms. Genbank information related to this gene is summarized below.

| Gene | GenBank Accession No. | GI Number | Organism |
|---|---|---|---|
| leuD | 3122345 | Q58673.1 | *Methanocaldococcus jannaschii* |

Another useful enzyme is fumarate hydratase (EC 4.2.1.2), also known as fumarase, that catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., J. Bacteriol. 183:461-467 (2001); Woods et al., Biochim. Biophys. Acta 954:14-26 (1988); Guest et al., J. Gen. Microbiol. 131:2971-2984 (1985)). *S. cerevisiae* contains one copy of a fumarase-encoding gene, FUM1, whose product localizes to both the cytosol and mitochondrion (Sass et al., J. Biol. Chem. 278:45109-45116 (2003)). Additional fumarase enzymes are found in *Campylobacter jejuni* (Smith et al., Int. J. Biochem. Cell. Biol. 31:961-975 (1999)), *Thermus thermophilus* (Mizobata et al., Arch. Biochem. Biophys. 355:49-55 (1998)) and *Rattus norvegicus* (Kobayashi et al., J. Biochem. 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., FEMS Microbiol. Lett. 270:207-213 (2007)). Genbank information related to these genes is summarized below.

| Gene | GenBank Accession No. | GI Number | Organism |
| --- | --- | --- | --- |
| fumA | NP_416129.1 | 16129570 | Escherichia coli |
| fumB | NP_418546.1 | 16131948 | Escherichia coli |
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

The enzyme OHED hydratase participates in 4-hydroxyphenylacetic acid degradation, where it converts 2-oxo-hept-4-ene-1,7-dioate (OHED) to 2-oxo-4-hydroxy-hepta-1,7-dioate (HODH) using magnesium as a cofactor (Burks et al., J. Am. Chem. Soc. 120 (1998). OHED hydratase enzymes have been identified and characterized in E. coli C (Izumi et la., J. Mol. Biol. 370:899-911 (2007); Roper et al., Gene 156:47-51 (1995)) and E. coli W (Prieto et al., J. Bacteriol. 178:111-120 (1996)). Sequence comparison reveals homologs in a range of bacteria, plants and animals. Enzymes with highly similar sequences are contained in Klebsiella pneumonia (91% identity, evalue=2e–138) and Salmonella estost (91% identity, evalue=4e–138), among others. Genbank information related to these genes is summarized below.

| Gene | GenBank Accession No. | GI Number | Organism |
| --- | --- | --- | --- |
| hpcG | CAA57202.1 | 556840 | Escherichia coli C |
| hpaH | CAA86044.1 | 757830 | Escherichia coli W |
| hpaH | ABR80130.1 | 150958100 | Klebsiella pneumoniae |
| Sari_01896 | ABX21779.1 | 160865156 | Salmonella enterica |

Yet another enzyme catalyzing a dehydration similar to step D of FIG. 3 is 2-(hydroxymethyl)glutarate dehydratase of Eubacterium barkeri. This enzyme has been studied in the context of nicotinate catabolism and is encoded by hmd (Alhapel et al., Proc. Natl. Acad. Sci. USA 103:12341-12346 (2006)). Similar enzymes with high sequence homology are found in Bacteroides capillosus and Anaerotruncus colihominis. These enzymes are also homologous to the α- and β-subunits of [4Fe-4S]-containing bacterial serine dehydratases, for example, E. coli enzymes encoded by tdcG, sdhB, and sdaA). Genbank information related to these genes is summarized below.

| Gene | GenBank Accession No. | GI Number | Organism |
| --- | --- | --- | --- |
| hmd | ABC88407.1 | 86278275 | Eubacterium barkeri |
| BACCAP_02294 | ZP_02036683.1 | 154498305 | Bacteroides capillosus ATCC 29799 |
| ANACOL_02527 | ZP_02443222.1 | 167771169 | Anaerotruncus colihominis DSM 17241 |

Another gene capable of encoding a dehydratase enzyme for step B or step D of FIG. 3 is 4-oxalomesaconate hydratase (or 4-carboxy-4-hydroxy-2-ketoadipate dehydratase). Exemplary enzymes can be found in Comamonas estosterone (Providenti et al., Microbiology, 2001, 147(Pt 8); 2157-67), Sphingomonas sp. SYK6 (Hara, et al., J Bacteriol, 2000, 182(24); 6950-7), and Pseudomonas ochraceae NGJ1 (Maruyama et al., Biosci Biotechnol Biochem, 2001 65(12); 2701-9; Maruyama et al., Biosci Biotechnol Biochem, 2004, 68(7); 1434-41).

| Gene | GenBank Accession No. | GI Number | Organism |
| --- | --- | --- | --- |
| pmdE | YP_003278787.1 | 264678880 | Comamonas testosteroni |
| ligJ | BAA97116.1 | 8777583 | Sphingomonas sp. SYK6 |
| proH | BAB21455.1 | 12539404 | Pseudomonas ochraceae NGJ1 |

Step C of FIG. 3 depicts 4-methylene-2-ketoglutarate reductase which reduces 4-methylene-2-ketoglutarate reductase to form 4-methyl-2-ketoglutarate. Step E of FIG. 3 depicts 4-methyl-2-ketoglutaconate reductase which reduces 4-methyl-2-ketoglutaconate to form 4-methyl-2-ketoglutarate. Various classes of enoate reductases can be applied to catalyze these transformations. Specific examples are provided below and several additional enoate reductase enzymes in the EC 1.3.1 can be alternatively utilized.

2-Enoate oxidoreductase enzymes are known to catalyze the NAD(P)H-dependent reduction and oxidation of a wide variety of α, β-unsaturated carboxylic acids and aldehydes (Rohdich et al., J. Biol. Chem. 276:5779-5787 (2001)). In the recently published genome sequence of C. kluyveri, 9 coding sequences for enoate reductases were reported, out of which one has been characterized (Seedorf et al., Proc. Natl. Acad. Sci. U.S.A. 105:2128-2133 (2008)). The enr genes from both C. tyrobutyricum and M. thermoaceticum have been cloned and sequenced and show 59% identity to each other. The former gene is also found to have approximately 75% similarity to the characterized gene in C. kluyveri (Giesel and Simon, Arch. Microbiol. 135:51-57 (1983)). It has been reported based on these sequence results that enr is very similar to the dienoyl CoA reductase in E. coli (fades) (Rohdich et al., J. Biol. Chem. 276:5779-5787 (2001)). The C. thermoaceticum enr gene has also been expressed in a catalytically active form in E. coli (Rohdich et al., supra). Genbank information related to these genes is summarized below.

| Gene | GenBank Accession No. | GI Number | Organism |
| --- | --- | --- | --- |
| enr | ACA54153.1 | 169405742 | Clostridium botulinum A3 str |
| enr | CAA71086.1 | 2765041 | Clostridium tyrobutyricum |
| enr | CAA76083.1 | 3402834 | Clostridium kluyveri |
| enr | YP_430895.1 | 83590886 | Moorella thermoacetica |
| fadH | NP_417552.1 | 16130976 | Escherichia coli |

MAR is a 2-enoate oxidoreductase catalyzing the reversible reduction of 2-maleylacetate (cis-4-oxohex-2-enedioate) to 3-oxoadipate (FIG. 2, Step O). MAR enzymes naturally participate in aromatic degradation pathways (Camara et al., J. Bacteriol. 191:4905-4915 (2009); Huang et al., Appl. Environ. Microbiol. 72:7238-7245 (2006); Kaschabek and Reineke, J. Bacteriol. 177:320-325 (1995); Kaschabek and Reineke, J. Bacteriol. 175:6075-6081 (1993)). The enzyme activity was identified and characterized in Pseudomonas sp. Strain B13 (Kaschabek and Reineke, (1995) supra; Kaschabek and Reineke, (1993) supra), and the coding gene was cloned and sequenced (Kasberg et al., *J. Bacteriol.* 179:3801-3803 (1997)). Additional MAR genes include cicE gene from *Pseudomonas* sp. Strain B13 (Kasberg et al., supra), macA gene from *Rhodococcus opacus* (Seibert et al., *J. Bacteriol.* 175:6745-6754 (1993)), the macA gene from *Ralstonia eutropha* (also known as *Cupriavidus necator*) (Seibert et al., *Microbiology* 150:463-472 (2004)), tfdFII from *Ralstonia eutropha* (Seibert et al., (1993) supra) and NCgl1112 in *Corynebacterium glutamicum* (Huang et al., *Appl. Environ Microbiol.* 72:7238-7245 (2006)). A MAR in *Pseudomonas reinekei* MT1, encoded by ccaD, was recently identified and the nucleotide sequence is available under the DBJ/EMBL GenBank accession number EF159980 (Camara et al., *J. Bacteriol.* 191:4905-4915 (2009). Genbank information related to these genes is summarized below.

| Gene | GenBank Accession No. | GI Number | Organism |
|---|---|---|---|
| clcE | O30847.1 | 3913241 | *Pseudomonas* sp. Strain B13 |
| macA | O84992.1 | 7387876 | *Rhodococcus opacus* |
| macA | AAD55886 | 5916089 | *Cupriavidus necator* |
| tfdFII | AC44727.1 | 1747424 | *Ralstonia eutropha* JMP134 |
| NCgl1112 | NP_600385 | 19552383 | *Corynebacterium glutamicum* |
| ccaD | EF159980.1 | 134133935 | *Pseudomonas reinekei* MT1 |

Fumarate reductase catalyzes the reduction of fumarate to succinate. The fumarate reductase of *E. coli*, composed of four subunits encoded byfrdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352:175-181 (1998)), which localize to the cytosol and promitochondrion, respectively, and are used for anaerobic growth on glucose (Arikawa et al., *FEMS Microbiol. Lett.* 165:111-116 (1998)).

| Protein | GenBank Accession No. | GI Number | Organism |
|---|---|---|---|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

EXAMPLE II

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three $CO_2$-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each step of the reductive TCA cycle are shown below.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha(4) beta(4) heteromeric enzyme from *Chlorobium limicola* was cloned and characterized in *E. coli* (Kanao et al., Eur. J. Biochem. 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, *J. Bacteriol.* 188:6544-6552 (2006). ACL enzymes have also been identified in *Balnearium lithotrophicum*, *Sulfurihydrogenibium subterraneum* and other members of the bacterial phylum Aquificae (Hugler et al., *Environ. Microbiol.* 9:81-92 (2007)). This acitivy has been reported in some fungi as well. Exemplary organisms include *Sordaria macrospora* (Nowrousian et al., *Curr. Genet.* 37:189-93 (2000), *Aspergillus nidulans, Yarrowia lipolytica* (Hynes and Murray, *Eukaryotic Cell*, July:1039-1048, (2010) and *Aspergillus niger* (Meijer et al. *J. Ind. Microbiol. Biotechnol.* 36:1275-1280 (2009). Other candidates can be found based on sequence homology. Information related to these enzymes is tabulated below:

| Protein | GenBank ID | GI Number | Organism |
|---|---|---|---|
| aclA | BAB21376.1 | 12407237 | *Chlorobium limicola* |
| aclB | BAB21375.1 | 12407235 | *Chlorobium limicola* |
| aclA | AAM72321.1 | 21647054 | *Chlorobium tepidum* |
| aclB | AAM72322.1 | 21647055 | *Chlorobium tepidum* |
| aclA | ABI50076.1 | 114054981 | *Balnearium lithotrophicum* |
| aclB | ABI50075.1 | 114054980 | *Balnearium lithotrophicum* |
| aclA | ABI50085.1 | 114055040 | *Sulfurihydrogenibium subterraneum* |
| aclB | ABI50084.1 | 114055039 | *Sulfurihydrogenibium subterraneum* |
| aclA | AAX76834.1 | 62199504 | *Sulfurimonas denitrificans* |
| aclB | AAX76835.1 | 62199506 | *Sulfurimonas denitrificans* |
| acl1 | XP_504787.1 | 50554757 | *Yarrowia lipolytica* |
| acl2 | XP_503231.1 | 50551515 | *Yarrowia lipolytica* |
| SPBC1703.07 | NP_596202.1 | 19112994 | *Schizosaccharomyces pombe* |
| SPAC22A12.16 | NP_593246.1 | 19114158 | *Schizosaccharomyces pombe* |
| acl1 | CAB76165.1 | 7160185 | *Sordaria macrospora* |
| acl2 | CAB76164.1 | 7160184 | *Sordaria macrospora* |
| aclA | CBF86850.1 | 259487849 | *Aspergillus nidulans* |
| aclB | CBF86848 | 259487848 | *Aspergillus nidulans* |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., *Appl. Microbiol. Biotechnol.* 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., *Mol. Micrbiol.* 52:751-761 (2004)). The citryl-CoA synthetase of *Aquifex*

*aeolicus* is composed of alpha and beta subunits encoded by sucC1 and sucD1 (Hugler et al., *Environ. Microbiol.* 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., *Mol. Microbiol.* 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002)).

| Protein | GenBank ID | GI Number | Organism |
| --- | --- | --- | --- |
| ccsA | BAD17844.1 | 46849514 | *Hydrogenobacter thermophilus* |
| ccsB | BAD17846.1 | 46849517 | *Hydrogenobacter thermophilus* |
| sucC1 | AAC07285 | 2983723 | *Aquifex aeolicus* |
| sucD1 | AAC07686 | 2984152 | *Aquifex aeolicus* |
| ccl | BAD17841.1 | 46849510 | *Hydrogenobacter thermophilus* |
| aq_150 | AAC06486 | 2982866 | *Aquifex aeolicus* |
| CT0380 | NP_661284 | 21673219 | *Chlorobium tepidum* |
| CT0269 | NP_661173.1 | 21673108 | *Chlorobium tepidum* |
| CT1834 | AAM73055.1 | 21647851 | *Chlorobium tepidum* |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278: 25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

| Protein | GenBank ID | GI Number | Organism |
| --- | --- | --- | --- |
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| Mdh | NP_417703.1 | 16131126 | *Escherichia coli* |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278: 45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

| Protein | GenBank ID | GI Number | Organism |
| --- | --- | --- | --- |
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352: 175-181 (1998)), which localize to the cytosol and promitochondrion, respectively, and are used during anaerobic growth on glucose (Arikawa et al., *FEMS Microbiol. Lett.* 165:111-116 (1998)).

| Protein | GenBank ID | GI Number | Organism |
| --- | --- | --- | --- |
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., *Biochemistry* 24:6245-6252 (1985)). These proteins are identified below:

| Protein | GenBank ID | GI Number | Organism |
| --- | --- | --- | --- |
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from $CO_2$ and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., *Archaea. Adv. Protein Chem.* 48:101-180 (1996)). Enzymes in this class are reversible and function in the carboxylation direction in organisms that fix carbon by the RTCA cycle such as *Hydrogenobacter thermophilus*, *Desulfobacter hydrogenophilus* and *Chlorobium species* (Shiba et al. 1985; Evans et al., Proc. Natl. Acad. ScI. U.S.A. 55:92934 (1966); Buchanan, 1971). The two-subunit enzyme from *H. thermophilus*, encoded by korAB, has been cloned and expressed in *E. coli* (Yun et al., Biochem. Biophys. Res. Commun. 282:589-594 (2001)). A five subunit OFOR from the same organism with strict substrate specificity for succinyl-CoA, encoded byforDABGE, was recently identified and expressed in *E. coli* (Yun et al. 2002). The kinetics of CO2 fixation of both *H. thermophilus* OFOR enzymes have been characterized (Yamamoto et al., Extremophiles 14:79-85 (2010)). A CO2-fixing OFOR from *Chlorobium thiosulfatophilum* has been purified and characterized but the genes encoding this enzyme have not been identified to date. Enzyme candidates in *Chlorobium* species can be inferred by sequence similarity to the *H. thermophilus* genes. For example, the *Chlorobium limicola* genome encodes two similar proteins. Acetogenic bacteria such as *Moorella thermoacetica* are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon *Sulfolobus* sp. strain 7, encoded by ST2300, has been extensively studied (Zhang et al. 1996. A plasmid-based expression system has been developed for efficiently expressing this protein in *E. coli* (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from *Aeropyrum pernix* str. K1 was recently cloned into *E. coli*, characterized, and found to react with 2-oxoglutarate and a broad range of 2-oxoacids (Nishizawa et al., FEBS Lett. 579:2319-2322 (2005)). Another exemplary OFOR is encoded by oorDABC in *Helicobacter pylori* (Hughes et al. 1998). An enzyme specific to alpha-ketoglutarate has been reported in *Thauera aromatics* (Dorner and Boll, J, Bacteriol. 184 (14), 3975-83 (2002). A similar enzyme can be found in *Rhodospirillum rubrum* by sequence homology. A two subunit enzyme has also been identified in *Chlorobium tepidum* (Eisen et al., PNAS 99(14): 9509-14 (2002)).

| Protein | GenBank ID | GI Number | Organism |
|---|---|---|---|
| korA | BAB21494 | 12583691 | Hydrogenobacter thermophilus |
| korB | BAB21495 | 12583692 | Hydrogenobacter thermophilus |
| forD | BAB62132.1 | 14970994 | Hydrogenobacter thermophilus |
| forA | BAB62133.1 | 14970995 | Hydrogenobacter thermophilus |
| forB | BAB62134.1 | 14970996 | Hydrogenobacter thermophilus |
| forG | BAB62135.1 | 14970997 | Hydrogenobacter thermophilus |
| forE | BAB62136.1 | 14970998 | Hydrogenobacter thermophilus |
| Clim_0204 | ACD89303.1 | 189339900 | Chlorobium limicola |
| Clim_0205 | ACD89302.1 | 189339899 | Chlorobium limicola |
| Clim_1123 | ACD90192.1 | 189340789 | Chlorobium limicola |
| Clim_1124 | ACD90193.1 | 189340790 | Chlorobium limicola |
| Moth_1984 | YP_430825.1 | 83590816 | Moorella thermoacetica |
| Moth_1985 | YP_430826.1 | 83590817 | Moorella thermoacetica |
| Moth_0034 | YP_428917.1 | 83588908 | Moorella thermoacetica |
| ST2300 | NP_378302.1 | 15922633 | Sulfolobus sp. strain 7 |
| Ape1472 | BAA80470.1 | 5105156 | Aeropyrum pernix |
| Ape1473 | BAA80471.2 | 116062794 | Aeropyrum pernix |
| oorD | AAC38210.1 (NP_207383.1) | 2935178 (15645213) | Helicobacter pylori |
| oorA | AAC38211.1 (NP_207384.1) | 2935179 (15645214) | Helicobacter pylori |
| oorB | AAC38212.1 (NP_207385.1) | 2935180 (15645215) | Helicobacter pylori |
| oorC | AAC38213.1 (NP_207386.1) | 2935181 (15645216) | Helicobacter pylori |
| CT0163 | NP_661069.1 | 21673004 | Chlorobium tepidum |
| CT0162 | NP_661068.1 | 21673003 | Chlorobium tepidum |
| korA | CAA12243.2 | 19571179 | Thauera aromatica |
| korB | CAD27440.1 | 19571178 | Thauera aromatica |
| Rru_A2721 | YP_427805.1 | 83594053 | Rhodospirillum rubrum |
| Rru_A2722 | YP_427806.1 | 83594054 | Rhodospirillum rubrum |

Isocitrate dehydrogenase catalyzes the reversible decarboxylation of isocitrate to 2-oxoglutarate coupled to the reduction of $NAD(P)^+$. IDH enzymes in *Saccharomyces cerevisiae* and *Escherichia coli* are encoded by IDP1 and icd, respectively (Haselbeck and McAlister-Henn, *J. Biol. Chem.* 266:2339-2345 (1991); Nimmo, H. G., *Biochem. J.* 234:317-2332 (1986)). The reverse reaction in the reductive TCA cycle, the reductive carboxylation of 2-oxoglutarate to isocitrate, is favored by the NADPH-dependent $CO_2$-fixing IDH from *Chlorobium limicola* and was functionally expressed in *E. coli* (Kanao et al., *Eur. J. Biochem.* 269:1926-1931 (2002)). A similar enzyme with 95% sequence identity is found in the *C. tepidum* genome in addititon to some other candidates listed below.

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In *H. thermophilus* the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, *Mol. Microbiol.* 62:748-759 (2006)). This enzyme is a large complex composed of two subunits. Biotinylation of the large (A) subunit is required for enzyme function (Aoshima et al., *Mol. Microbiol.* 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in *H. thermophilus*. The kinetic parameters of this enzyme indicate that the enzyme only operates in the reductive carboxylation direction in vivo, in contrast to isocitrate dehydrogenase enzymes in other organisms (Aoshima and Igarashi, *J. Bacteriol.* 190:2050-2055 (2008)). Based on sequence homology, gene candidates have also been found in *Thiobacillus denitrificans* and *Thermocrinis albus*.

| Protein | GenBank ID | GI Number | Organism |
|---|---|---|---|
| cifA | BAF34932.1 | 116234991 | *Hydrogenobacter thermophilus* |
| cifB | BAF34931.1 | 116234990 | *Hydrogenobacter thermophilus* |
| Icd | BAD02487.1 | 38602676 | *Hydrogenobacter thermophilus* |
| Tbd_1556 | YP_315314 | 74317574 | *Thiobacillus denitrificans* |
| Tbd_1555 | YP_315313 | 74317573 | *Thiobacillus denitrificans* |
| Tbd_0854 | YP_314612 | 74316872 | *Thiobacillus denitrificans* |
| Thal_0268 | YP_003473030 | 289548042 | *Thermocrinis albus* |
| Thal_0267 | YP_003473029 | 289548041 | *Thermocrinis albus* |
| Thal_0646 | YP_003473406 | 289548418 | *Thermocrinis albus* |

Aconitase (EC 4.2.1.3) is an iron-sulfur-containing protein catalyzing the reversible isomerization of citrate and isocitrate via the intermediate cis-aconitate. Two aconitase enzymes are encoded in the *E. coli* genome by acnA and acnB. AcnB is the main catabolic enzyme, while AcnA is more stable and appears to be active under conditions of oxidative or acid stress (Cunningham et al., *Microbiology* 143 (Pt 12):3795-3805 (1997)). Two isozymes of aconitase in *Salmonella typhimurium* are encoded by acnA and acnB (Horswill and Escalante-Semerena, *Biochemistry* 40:4703-4713 (2001)). The *S. cerevisiae* aconitase, encoded by ACO1, is localized to the mitochondria where it participates in the TCA cycle (Gangloff et al., *Mol. Cell. Biol.* 10:3551-3561 (1990)) and the cytosol where it participates in the glyoxylate shunt (Regev-Rudzki et al., *Mol. Biol. Cell.* 16:4163-4171 (2005)).

| Protein | GenBank ID | GI Number | Organism |
|---|---|---|---|
| acnA | AAC7438.1 | 1787531 | *Escherichia coli* |
| acnB | AAC73229.1 | 2367097 | *Escherichia coli* |
| acnA | NP_460671.1 | 16765056 | *Salmonella typhimurium* |
| HP0779 | NP_207572.1 | 15645398 | *Helicobacter pylori* 26695 |
| H16_B0568 | CAJ95365.1 | 113529018 | *Ralstonia eutropha* |
| DesfrDRAFT_3783 | ZP_07335307.1 | 303249064 | *Desulfovibrio fructosovorans* JJ |
| Suden_1040 (acnB) | ABB44318.1 | 78497778 | *Sulfurimonas denitrificans* |
| Hydth_0755 | ADO45152.1 | 308751669 | *Hydrogenobacter thermophilus* |
| CT0543 (acn) | AAM71785.1 | 21646475 | *Chlorobium tepidum* |
| Clim_2436 | YP_001944436.1 | 189347907 | *Chlorobium limicola* |
| Clim_0515 | ACD89607.1 | 189340204 | *Chlorobium limicola* |
| acnB | NP_459163.1 | 16763548 | *Salmonella typhimurium* |
| ACO1 | AAA34389.1 | 170982 | *Saccharomyces cerevisiae* |

Pyruvate:ferredoxin oxidoreductase (PFOR) catalyzes the reversible oxidation of pyruvate to form acetyl-CoA. The PFOR from *Desulfovibrio africanus* has been cloned and expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that protects it against inactivation in the form of oxygen. This disulfide bond and the stability in the presence of oxygen has been found in other *Desulfovibrio* species also (Vita et al., Biochemistry, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275:28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatus* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| DesfrDRAFT_0121 | ZP_07331646.1 | 303245362 | *Desulfovibrio fructosovorans* JJ |
| Por | CAA70873.1 | 1770208 | *Desulfovibrio africanus* |
| por | YP_012236.1 | 46581428 | *Desulfovibrio vulgaris* str. Hildenborough |
| Dde_3237 | ABB40031.1 | 78220682 | *DesulfoVibrio desulfuricans* G20 |
| Ddes_0298 | YP_002478891.1 | 220903579 | *Desulfovibrio desulfuricans* subsp. *desulfuricans* str. ATCC 27774 |

| Protein | GenBank ID | GI Number | Organism |
|---|---|---|---|
| Por | YP_428946.1 | 83588937 | Moorella thermoacetica |
| YdbK | NP_415896.1 | 16129339 | Escherichia coli |
| nifJ (CT1628) | NP_662511.1 | 21674446 | Chlorobium tepidum |
| CJE1649 | YP_179630.1 | 57238499 | Campylobacter jejuni |
| nifJ | ADE85473.1 | 294476085 | Rhodobacter capsulatus |
| porE | BAA95603.1 | 7768912 | Hydrogenobacter thermophilus |
| porD | BAA95604.1 | 7768913 | Hydrogenobacter thermophilus |
| porA | BAA95605.1 | 7768914 | Hydrogenobacter thermophilus |
| porB | BAA95606.1 | 776891 | Hydrogenobacter thermophilus |
| porG | BAA95607.1 | 7768916 | Hydrogenobacter thermophilus |
| FqrB | YP_001482096.1 | 157414840 | Campylobacter jejuni |
| HP1164 | NP_207955.1 | 15645778 | Helicobacter pylori |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including E. coli and S. cerevisiae. In the E. coli enzyme, specific residues in the E1 component are responsible for substrate specificity (Bisswanger, H., J. Biol. Chem. 256:815-82 (1981); Bremer, J., Eur. J. Biochem. 8:535-540 (1969); Gong et al., J. Biol. Chem. 275:13645-13653 (2000)). Enzyme engineering efforts have improved the E. coli PDH enzyme activity under anaerobic conditions (Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the E. coli PDH, the B. subtilis complex is active and required for growth under anaerobic conditions (Nakano et al., J. Bacteriol. 179:6749-6755 (1997)). The Klebsiella pneumoniae PDH, characterized during growth on glycerol, is also active under anaerobic conditions (5). Crystal structures of the enzyme complex from bovine kidney (18) and the E2 catalytic domain from Azotobacter vinelandii are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in Escherichia coli encoded by pflB (Knappe and Sawers, FEMS. Microbiol Rev. 6:383-398 (1990)), Lactococcus lactis (Melchiorsen et al., Appl Microbiol Biotechnol 58:338-344 (2002)), and Streptococcus mutans (Takahashi-Abbe et al., Oral. Microbiol Immunol. 18:293-297 (2003)). E. coli possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol. 27:477-492 (1998)). Both pflB and tdcE from E. coli require the presence of pyruvate formate lyase activating enzyme, encoded by pflA. Further, a short protein encoded by yfiD in E. coli can associate with and restore activity to oxygen-cleaved pyruvate formate lyase (Vey et al., Proc. Natl. Acad. Sci. U.S.A. 105:16137-16141 (2008). Note that pflA and pflB from E. coli were expressed in S. cerevisiae as a means to increase cytosolic acetyl-CoA for butanol production as described in WO/2008/080124]. Additional pyruvate formate lyase and activating enzyme candidates, encoded by pfl and act, respectively, are found in Clostridium pasteurianum (Weidner et al., J. Bacteriol. 178:2440-2444 (1996)).

Further, different enzymes can be used in combination to convert pyruvate into acetyl-CoA. For example, in S. cerevisiae, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including E. coli (Kumari et al., J. Bacteriol. 177: 2878-2886 (1995)), Salmonella enterica (Starai et al., Microbiology 151:3793-3801 (2005); Starai et al., J. Biol. Chem. 280:26200-26205 (2005)), and Moorella thermoacetica (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several Clostridia and Methanosarcina thermophile.

Yet another way of converting pyruvate to acetyl-CoA is via pyruvate oxidase. Pyruvate oxidase converts pyruvate into acetate, using ubiquione as the electron acceptor. In E. coli, this activity is encoded by poxB. PoxB has similarity to pyruvate decarboxylase of S. cerevisiae and Zymomonas mobilis. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to NAD(P)$^+$, ferredoxin:NAD$^+$ oxidoreductase (EC 1.18.1.3) and ferredoxin:NADP$^+$ oxidoreductase (FNR, EC 1.18.1.2). Ferredoxin:NADP$^+$ oxidoreductase (FNR, EC 1.18.1.2) has a noncovalently ow-potential acceptors such as ferredoxins or flavodoxins (Blaschkowski et al., Eur. J. Biochem. 123:563-569 (1982);

Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:NADP$^+$ oxidoreductase enzyme is encoded in the *E. coli* genome by fpr (Bianchi et al. 1993). Ferredoxin:NAD$^+$ oxidoreductase utilizes reduced ferredoxin to generate NADH from NAD$^+$. In several organisms, including *E. coli*, this enzyme is a component of multifunctional dioxygenase enzyme complexes. The ferredoxin:NAD$^+$ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). Finally, the energy-conserving membrane-associated Rnf-type proteins (Seedorf et al., Proc. Natl. Acad. Sci. U.S.A. 105:2128-2133 (2008); Herrmann et al., *J. Bacteriol.* 190:784-791 (2008)) provide a means to generate NADH or NADPH from reduced ferredoxin. Additional ferredoxin:NAD(P)+ oxidoreductases have been annotated in *Clostridium carboxydivorans* P7.

doxins donate electrons to Fe-dependent enzymes such as ferredoxin-NADP$^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella*

| Protein | GenBank ID | GI Number | Organism |
|---|---|---|---|
| HP1164 | NP_207955.1 | 15645778 | *Helicobacter pylori* |
| RPA3954 | CAE29395.1 | 39650872 | *Rhodopseudomonas palustris* |
| fpr | BAH29712.1 | 225320633 | *Hydrogenobacter thermophilus* |
| yumC | NP_391091.2 | 255767736 | *Bacillus subtilis* |
| CJE0663 | AAW35824.1 | 57167045 | *Campylobacter jejuni* |
| fpr | P28861.4 | 399486 | *Escherichia coli* |
| hcaD | AAC75595.1 | 1788892 | *Escherichia coli* |
| LOC100282643 | NP_001149023.1 | 226497434 | *Zea mays* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |
| CcarbDRAFT_2639 | ZP_05392639.1 | 255525707 | *Clostridium carboxidivorans* P7 |
| CcarbDRAFT_2638 | ZP_05392638.1 | 255525706 | *Clostridium carboxidivorans* P7 |
| CcarbDRAFT_2636 | ZP_05392636.1 | 255525704 | *Clostridium carboxidivorans* P7 |
| CcarbDRAFT_5060 | ZP_05395060.1 | 255528241 | *Clostridium carboxidivorans* P7 |
| CcarbDRAFT_2450 | ZP_05392450.1 | 255525514 | *Clostridium carboxidivorans* P7 |
| CcarbDRAFT_1084 | ZP_05391084.1 | 255524124 | *Clostridium carboxidivorans* P7 |

Ferredoxins are small acidic proteins containing one or more iron-sulfur clusters that function as intracellular electron carriers with a low reduction potential. Reduced ferredoxins are predicted to encode several ferredoxins, listed in the table below.

*thermoacetica, Clostridium carboxidivorans* P7 and *Rhodospirillum rubrum* are predicted to encode several ferredoxins, listed in the table below.

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |

| Protein | GenBank ID | GI Number | Organism |
| --- | --- | --- | --- |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| fdx | CAA12251.1 | 3724172 | Thauera aromatica |
| CHY_2405 | YP_361202.1 | 78044690 | Carboxydothermus hydrogenoformans |
| fer | YP_359966.1 | 78045103 | Carboxydothermus hydrogenoformans |
| fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of Clostridium kluyveri has been shown to exhibit succinyl-CoA: acetyl-CoA transferase activity (Sohling and Gottschalk, J. Bacteriol. 178:871-880 (1996)). In addition, the activity is present in Trichomonas vaginalis (van Grinsven et al. 2008) and Trypanosoma brucei (Riviere et al. 2004). The succinyl-CoA: acetate CoA-transferase from Acetobacter aceti, encoded by aarC, replaces succinyl-CoA synthetase in a variant TCA cycle (Mullins et al. 2008). Similar succinyl-CoA transferase activities are also present in Trichomonas vaginalis (van Grinsven et al. 2008), Trypanosoma brucei (Riviere et al. 2004) and Clostridium kluyveri (Sohling and Gottschalk, 1996c). The beta-ketoadipate:succinyl-CoA transferase encoded by pcaI and pcaJ in Pseudomonas putida is yet another candidate (Kaschabek et al. 2002). The aforementioned proteins are identified below.

| Protein | GenBank ID | GI Number | Organism |
| --- | --- | --- | --- |
| cat1 | P38946.1 | 729048 | Clostridium kluyveri |
| TVAG_395550 | XP_001330176 | 123975034 | Trichomonas vaginalis G3 |
| Tb11.02.0290 | XP_828352 | 71754875 | Trypanosoma brucei |
| pcaI | AAN69545.1 | 24985644 | Pseudomonas putida |
| pcaJ | NP_746082.1 | 26990657 | Pseudomonas putida |
| aarC | ACD85596.1 | 189233555 | Acetobacter aceti |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in Helicobacter pylori (Corthesy-Theulaz et al. 1997), Bacillus subtilis, and Homo sapiens (Fukao et al. 2000; Tanaka et al. 2002). The aforementioned proteins are identified below.

| Protein | GenBank ID | GI Number | Organism |
| --- | --- | --- | --- |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |
| OXCT1 | NP_000427 | 4557817 | Homo sapiens |
| OXCT2 | NP_071403 | 11545841 | Homo sapiens |

Converting succinate to succinyl-CoA by succinyl-CoA:3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA: acetate: CoA transferase. Acetoacetyl-CoA: acetate: CoA transferase converts acetoacetyl-CoA and acetate to acetoacetate and acetyl-CoA, or vice versa. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., *Biosci. Biotechnol Biochem.* 71:58-68 (2007)) are shown below.

| Protein | GenBank ID | GI Number | Organism |
|---|---|---|---|
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatics* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

| Protein | GenBank ID | GI Number | Organism |
|---|---|---|---|
| bbsE | AAF89840 | 9622535 | *Thauera aromatica* |
| Bbsf | AAF89841 | 9622536 | *Thauera aromatica* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

| Protein | GenBank ID | GI Number | Organism |
|---|---|---|---|
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88 (1997); Bott and Dimroth, *Mol. Microbiol.* 14:347-356 (1994)). The aforementioned proteins are tabulated below.

| Protein | GenBank ID | GI Number | Organism |
|---|---|---|---|
| citF | AAC73716.1 | 1786832 | *Escherichia coli* |
| Cite | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | *Escherichia coli* |
| citX | AAC73715.1 | 1786831 | *Escherichia coli* |
| citF | CAA71633.1 | 2842397 | *Leuconostoc mesenteroides* |
| Cite | CAA71632.1 | 2842396 | *Leuconostoc mesenteroides* |
| citD | CAA71635.1 | 2842395 | *Leuconostoc mesenteroides* |
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| cite | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |
| citG | NP_459611.1 | 16763996 | *Salmonella typhimurium* |
| citX | NP_459612.1 | 16763997 | *Salmonella typhimurium* |
| citF | CAA56217.1 | 565619 | *Klebsiella pneumoniae* |
| cite | CAA56216.1 | 565618 | *Klebsiella pneumoniae* |
| citD | CAA56215.1 | 565617 | *Klebsiella pneumoniae* |
| citC | BAH66541.1 | 238774045 | *Klebsiella pneumoniae* |
| citG | CAA56218.1 | 565620 | *Klebsiella pneumoniae* |
| citX | AAL60463.1 | 18140907 | *Klebsiella pneumoniae* |

Acetate kinase (EC 2.7.2.1) catalyzes the reversible ATP-dependent phosphorylation of acetate to acetylphosphate. Exemplary acetate kinase enzymes have been characterized in many organisms including *E. coli, Clostridium acetobutylicum* and *Methanosarcina thermophile* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

| Protein | GenBank ID | GI Number | Organism |
|---|---|---|---|
| ackA | NP_416799.1 | 16130231 | Escherichia coli |
| Ack | AAB18301.1 | 1491790 | Clostridium acetobutylicum |
| Ack | AAA72042.1 | 349834 | Methanosarcina thermophila |
| purT | AAC74919.1 | 1788155 | Escherichia coli |
| buk1 | NP_349675 | 15896326 | Clostridium acetobutylicum |
| buk2 | Q97II1 | 20137415 | Clostridium acetobutylicum |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

| Protein | GenBank ID | GI Number | Organism |
|---|---|---|---|
| Pta | NP_416800.1 | 71152910 | Escherichia coli |
| Pta | P39646 | 730415 | Bacillus subtilis |
| Pta | A5N801 | 146346896 | Clostridium kluyveri |
| Pta | Q9X0L4 | 6685776 | Thermotoga maritima |
| Ptb | NP_349676 | 34540484 | Clostridium acetobutylicum |
| Ptb | AAR19757.1 | 38425288 | butyrate-producing bacterium L2-50 |
| Ptb | CAC07932.1 | 10046659 | Bacillus megaterium |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, Biochemistry 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., Biochemistry 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

| Protein | GenBank ID | GI Number | Organism |
|---|---|---|---|
| acs | AAC77039.1 | 1790505 | Escherichia coli |
| acoE | AAA21945.1 | 141890 | Ralstonia eutropha |
| acs1 | ABC87079.1 | 86169671 | Methanothermobacter thermautotrophicus |
| acs1 | AAL23099.1 | 16422835 | Salmonella enterica |
| ACS1 | Q01574.2 | 257050994 | Saccharomyces cerevisiae |
| AF1211 | NP_070039.1 | 11498810 | Archaeoglobus fulgidus |
| AF1983 | NP_070807.1 | 11499565 | Archaeoglobus fulgidus |
| scs | YP_135572.1 | 55377722 | Haloarcula marismortui |
| PAE3250 | NP_560604.1 | 18313937 | Pyrobaculum aerophilum str. IM2 |
| sucC | NP_415256.1 | 16128703 | Escherichia coli |
| sucD | AAC73823.1 | 1786949 | Escherichia coli |
| paaF | AAC24333.2 | 22711873 | Pseudomonas putida |

The product yields per C-mol of substrate of microbial cells synthesizing reduced fermentation products such as propylene, are limited by insufficient reducing equivalents in the carbohydrate feedstock. Reducing equivalents, or electrons, can be extracted from synthesis gas components such as CO and $H_2$ using carbon monoxide dehydrogenase (CODH) and hydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin and NAD(P)H are particularly useful as they can serve as redox carriers for various Wood-Ljungdahl pathway and reductive TCA cycle enzymes.

When both feedstocks of sugar and syngas are available, the syngas components CO and $H_2$ can be utilized to generate reducing equivalents by employing the hydrogenase and CO dehydrogenase. The reducing equivalents generated from syngas components will be utilized to power the glucose to propylene production pathways. Theoretically, all carbons in glucose will be conserved, thus resulting in a maximal theoretical yield to produce propylene from glucose.

As described above, a combined feedstock strategy where syngas is combined with a sugar-based feedstock or other carbon substrate can greatly improve the theoretical yields. In this co-feeding appoach, syngas components $H_2$ and CO can be utilized by the hydrogenase and CO dehydrogenase to generate reducing equivalents, that can be used to power chemical production pathways in which the carbons from sugar or other carbon substrates will be maximally conserved and the theoretical yields improved for production of propylene. Such improvements provide environmental and economic benefits and greatly enhance sustainable chemical production.

Herein below the enzymes and the corresponding genes used for extracting redox from synags components are described. CODH is a reversible enzyme that interconverts CO and $CO_2$ at the expense or gain of electrons. The natural physiological role of the CODH in ACS/CODH complexes is to convert $CO_2$ to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (Genbank Accession Number: YP_430813) is expressed by itself in an operon and is believed to transfer electrons from CO to an external mediator like ferredoxin in a "Ping-pong" reaction. The reduced mediator then couples to other reduced nicolinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

In some cases, hydrogenase encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J. Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)). The protein sequences of exemplary CODH and hydrogenase genes can be identified by the following GenBank accession numbers.

| Protein | GenBank ID | GI Number | Organism |
|---|---|---|---|
| CODH-I (CooS-I) | YP_360644 | 78043418 | *Carboxydothermus hydrogenoformans* |
| CooF | YP_360645 | 78044791 | *Carboxydothermus hydrogenoformans* |
| HypA | YP_360646 | 78044340 | *Carboxydothermus hydrogenoformans* |
| CooH | YP_360647 | 78043871 | *Carboxydothermus hydrogenoformans* |
| CooU | YP_360648 | 78044023 | *Carboxydothermus hydrogenoformans* |
| CooX | YP_360649 | 78043124 | *Carboxydothermus hydrogenoformans* |
| CooL | YP_360650 | 78043938 | *Carboxydothermus hydrogenoformans* |
| CooK | YP_360651 | 78044700 | *Carboxydothermus hydrogenoformans* |
| CooM | YP_360652 | 78043942 | *Carboxydothermus hydrogenoformans* |
| CooC | YP_360654.1 | 78043296 | *Carboxydothermus hydrogenoformans* |
| CooA-1 | YP_360655.1 | 78044021 | *Carboxydothermus hydrogenoformans* |

| Protein | GenBank ID | GI Number | Organism |
|---|---|---|---|
| CODH (putative) | YP_430813 | 83590804 | *Moorella thermoacetica* |
| CODH-II (CooS-II) | YP_358957 | 78044574 | *Carboxydothermus hydrogenoformans* |
| CooF | YP_358958 | 78045112 | *Carboxydothermus hydrogenoformans* |
| CODH (putative) | ZP_05390164.1 | 255523193 | *Clostridium carboxidivorans* P7 |
| CcarbDRAFT_0341 | ZP_05390341.1 | 255523371 | *Clostridium carboxidivorans* P7 |
| CcarbDRAFT_1756 | ZP_05391756.1 | 255524806 | *Clostridium carboxidivorans* P7 |
| CcarbDRAFT_2944 | ZP_05392944.1 | 255526020 | *Clostridium carboxidivorans* P7 |
| CODH | YP_384856.1 | 78223109 | *Geobacter metallireducens* GS-15 |
| Cpha266_0148 (cytochrome c) | YP_910642.1 | 119355998 | *Chlorobium phaeobacteroides* DSM 266 |
| Cpha266_0149 (CODH) | YP_910643.1 | 119355999 | *Chlorobium phaeobacteroides* DSM 266 |
| Ccel_0438 | YP_002504800.1 | 220927891 | *Clostridium cellulolyticum* H10 |
| Ddes_0382 (CODH) | YP_002478973.1 | 220903661 | *Desulfovibrio desulfuricans* subsp. *desulfuricans* str. ATCC 27774 |
| Ddes_0381 (CooC) | YP_002478972.1 | 220903660 | *Desulfovibrio desulfuricans* subsp. *desulfuricans* str. ATCC 27774 |
| Pcar_0057 (CODH) | YP_355490.1 | 7791767 | *Pelobacter carbinolicus* DSM 2380 |
| Pcar_0058 (CooC) | YP_355491.1 | 7791766 | *Pelobacter carbinolicus* DSM 2380 |
| Pcar_0058 (HypA) | YP_355492.1 | 7791765 | *Pelobacter carbinolicus* DSM 2380 |
| CooS (CODH) | YP_001407343.1 | 154175407 | *Campylobacter curvus* 525.92 |

| Protein | GenBank ID | GI Number | Organism |
| --- | --- | --- | --- |
| CooL | AAC45118 | 1515468 | *Rhodospirillum rubrum* |
| CooX | AAC45119 | 1515469 | *Rhodospirillum rubrum* |
| CooU | AAC45120 | 1515470 | *Rhodospirillum rubrum* |
| CooH | AAC45121 | 1498746 | *Rhodospirillum rubrum* |
| CooF | AAC45122 | 1498747 | *Rhodospirillum rubrum* |
| CODH (CooS) | AAC45123 | 1498748 | *Rhodospirillum rubrum* |
| CooC | AAC45124 | 1498749 | *Rhodospirillum rubrum* |
| CooT | AAC45125 | 1498750 | *Rhodospirillum rubrum* |
| CooJ | AAC45126 | 1498751 | *Rhodospirillum rubrum* |

Native to *E. coli* and other enteric bacteria are multiple genes encoding up to four hydrogenases (Sawers, G., *Antonie Van Leeuwenhoek* 66:57-88 (1994); Sawers et al., *J. Bacteriol.* 164:1324-1331 (1985); Sawers and Boxer, *Eur. J Biochem.* 156:265-275 (1986); Sawers et al., *J Bacteriol.* 168: 398-404 (1986)). Given the multiplicity of enzyme activities, *E. coli* or another host organism can provide sufficient hydrogenase activity to split incoming molecular hydrogen and reduce the corresponding acceptor. *E. coli* possesses two uptake hydrogenases, Hyd-1 and Hyd-2, encoded by the hyaABCDEF and hybOABCDEFG gene clusters, respectively (Lukey et al., How *E. coli* is equipped to oxidize hydrogen under different redox conditions, *J Biol Chem* published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

| Protein | GenBank ID | GI Number | Organism |
| --- | --- | --- | --- |
| HyaA | AAC74057.1 | 1787206 | *Escherichia coli* |
| HyaB | AAC74058.1 | 1787207 | *Escherichia coli* |
| HyaC | AAC74059.1 | 1787208 | *Escherichia coli* |
| HyaD | AAC74060.1 | 1787209 | *Escherichia coli* |
| HyaE | AAC74061.1 | 1787210 | *Escherichia coli* |
| HyaF | AAC74062.1 | 1787211 | *Escherichia coli* |
| HybO | AAC76033.1 | 1789371 | *Escherichia coli* |
| HybA | AAC76032.1 | 1789370 | *Escherichia coli* |
| HybB | AAC76031.1 | 2367183 | *Escherichia coli* |
| HybC | AAC76030.1 | 1789368 | *Escherichia coli* |
| HybD | AAC76029.1 | 1789367 | *Escherichia coli* |
| HybE | AAC76028.1 | 1789366 | *Escherichia coli* |
| HybF | AAC76027.1 | 1789365 | *Escherichia coli* |
| HybG | AAC76026.1 | 1789364 | *Escherichia coli* |

The hydrogen-lyase systems of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., *Appl Microbiol Biotechnol* 76(5):1035-42 (2007)). Hydrogenase activity in *E. coli* is also dependent upon the expression of the hyp genes whose corresponding proteins are involved in the assembly of the hydrogenase complexes (Jacobi et al., *Arch. Microbiol* 158:444-451 (1992); Rangarajan et al., *J. Bacteriol,* 190: 1447-1458 (2008)).

| Protein | GenBank ID | GI Number | Organism |
| --- | --- | --- | --- |
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |

The *M. thermoacetica* hydrogenases are suitable for a host that lacks sufficient endogenous hydrogenase activity. *M. thermoacetica* can grow with $CO_2$ as the exclusive carbon source indicating that reducing equivalents are extracted from $H_2$ to enable acetyl-CoA synthesis via the Wood-Ljungdahl pathway (Drake, H. L., *J. Bacteriol.* 150:702-709 (1982); Drake and Daniel, *Res. Microbiol.* 155:869-883 (2004); Kellum and Drake, *J. Bacteriol.* 160:466-469 (1984)) (see FIG. 6). *M. thermoacetica* has homologs to several hyp, hyc, and hyf genes from *E. coli*. The protein sequences encoded for by these genes are identified by the following GenBank accession numbers.

Proteins in *M. thermoacetica* whose genes are homologous to the *E. coli* hyp genes are shown below.

| Protein | GenBank ID | GI Number | Organism |
| --- | --- | --- | --- |
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

Proteins in *M. thermoacetica* that are homologous to the *E. coli* Hydrogenase 3 and/or 4 proteins are listed in the following table.

| Protein | GenBank ID | GI Number | Organism |
| --- | --- | --- | --- |
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |

| Protein | GenBank ID | GI Number | Organism |
| --- | --- | --- | --- |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |

In addition, several gene clusters encoding hydrogenase functionality are present in *M. thermoacetica* and their corresponding protein sequences are provided below.

| Protein | GenBank ID | GI Number | Organism |
| --- | --- | --- | --- |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

| Protein | GenBank ID | GI Number | Organism |
| --- | --- | --- | --- |
| HoxF | NP_942727.1 | 38637753 | Ralstonia eutropha H16 |
| HoxU | NP_942728.1 | 38637754 | Ralstonia eutropha H16 |
| HoxY | NP_942729.1 | 38637755 | Ralstonia eutropha H16 |
| HoxH | NP_942730.1 | 38637756 | Ralstonia eutropha H16 |
| HoxW | NP_942731.1 | 38637757 | Ralstonia eutropha H16 |
| HoxI | NP_942732.1 | 38637758 | Ralstonia eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
| --- | --- | --- | --- |
| Ppc | NP_418391 | 16131794 | Escherichia coli |
| ppcA | AAB58883 | 28572162 | Methylobacterium extorquens |
| Ppc | ABB53270 | 80973080 | Corynebacterium glutamicum |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., Appl. Environ. Microbiol. 70:1238-1241 (2004)). Nevertheless, activity of the native E. coli PEP carboxykinase from PEP towards oxaloacetate has been recently demonstrated in ppc mutants of E. coli K-12 (Kwon et al., J. Microbiol. Biotechnol. 16:1448-1452 (2006)). These strains exhibited no growth defects and had increased succinate production at high $NaHCO_3$ concentrations. Mutant strains of E. coli can adopt Pck as the dominant $CO_2$-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into E. coli include those from Mannheimia succiniciproducens (Lee et al., Biotechnol. Bioprocess Eng. 7:95-99 (2002)), Anaerobiospirillum succiniciproducens (Laivenieks et al., Appl. Environ. Microbiol. 63:2273-2280 (1997), and Actinobacillus succinogenes (Kim et al. supra). The PEP carboxykinase enzyme encoded by Haemophilus influenza is effective at forming oxaloacetate from PEP.

| Protein | GenBank ID | GI Number | Organism |
|---|---|---|---|
| PCK1 | NP_013023 | 6322950 | Saccharomyces cerevisiae |
| pck | NP_417862.1 | 16131280 | Escherichia coli |
| pckA | YP_089485.1 | 52426348 | Mannheimia succiniciproducens |
| pckA | O09460.1 | 3122621 | Anaerobiospirillum succiniciproducens |
| pckA | Q6W6X5 | 75440571 | Actinobacillus succinogenes |
| pckA | P43923.1 | 1172573 | Haemophilus influenza |

Pyruvate carboxylase (EC 6.4.1.1) directly converts pyruvate to oxaloacetate at the cost of one ATP. Pyruvate carboxylase enzymes are encoded by PYC1 (Walker et al., Biochem. Biophys. Res. Commun. 176:1210-1217 (1991) and PYC2 (Walker et al., supra) in Saccharomyces cerevisiae, and pyc in Mycobacterium smegmatis (Mukhopadhyay and Purwantini, Biochim. Biophys. Acta 1475:191-206 (2000)).

| Protein | GenBank ID | GI Number | Organism |
|---|---|---|---|
| PYC1 | NP_011453 | 6321376 | Saccharomyces cerevisiae |
| PYC2 | NP_009777 | 6319695 | Saccharomyces cerevisiae |
| Pyc | YP_890857.1 | 118470447 | Mycobacterium smegmatis |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the E. coli malic enzymes (Takeo, J. Biochem. 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in E. coli while restoring the lethal ΔpflΔldhA phenotype under anaerobic conditions by operating in the carbon-fixing direction (Stols and Donnelly, Appl. Environ. Microbiol. 63(7) 2695-2701 (1997)). A similar observation was made upon overexpressing the malic enzyme from Ascaris suum in E. coli (Stols et al., Appl. Biochem. Biotechnol. 63-65(1), 153-158 (1997)). The second E. coli malic enzyme, encoded by maeB, is NADP-dependent and also decarboxylates oxaloacetate and other alpha-keto acids (Iwakura et al., J. Biochem. 85(5):1355-65 (1979)).

| Protein | GenBank ID | GI Number | Organism |
|---|---|---|---|
| maeA | NP_415996 | 90111281 | Escherichia coli |
| maeB | NP_416958 | 16130388 | Escherichia coli |
| NAD-ME | P27443 | 126732 | Ascaris suum |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and/or $H_2$, as disclosed herein, improve the yields of propylene when utilizing carbohydrate-based feedstock. For example, propylene can be produced as exemplified in the figures using enzymes as disclosed herein.

Enzymes, genes and methods for engineering pathways from glycolysis intermediates to various products into a microorganism are known in the art. The additional reducing equivalents obtained from CO and $H_2$, as described herein, improve the yields of all these products, including propylene, on carbohydrates.

EXAMPLE III

Methods for Handling CO and Anaerobic Cultures

This example describes methods used in handling CO and anaerobic cultures.

A. Handling of CO in Small Quantities for Assays and Small Cultures. CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL)

cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in Larger Quantities Fed to Large-Scale Cultures. Fermentation cultures are fed either CO or a mixture of CO and $H_2$ to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic Chamber and Conditions. Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

D. Anaerobic Microbiology. Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 µM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

EXAMPLE IV

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum*, *Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., Biochemistry 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mL of reaction buffer (50 mM Hepes, pH 8.5, 2 mM dithiothreitol (DTT) was added using a 22 Ga. needle, with exhaust needled, and 100% CO. Methyl viologen ($CH_3$ viologen) stock was 1 M in water. Each assay used 20 microliters for 20 mM final concentration. When methyl viologen was added, an 18 Ga needle (partial) was used as a jacket to facilitate use of a Hamilton syringe to withdraw the $CH_3$ viologen. 4-5 aliquots were drawn up and discarded to wash and gas equilibrate the syringe. A small amount of sodium dithionite (0.1 M stock) was added when making up the $CH_3$ viologen stock to slightly reduce the $CH_3$ viologen. The temperature was equilibrated to 55° C. in a heated Olis spectrophotometer (Bogart Ga.). A blank reaction ($CH_3$ viologen+buffer) was run first to measure the base rate of $CH_3$ viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced $CH_3$ viologen turns purple. The results of an assay are shown in Table I.

TABLE I

| Crude extract CO Oxidation Activities. | | | |
|---|---|---|---|
| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

| Averages | |
|---|---|
| ACS90 | 0.057 U/mg |
| ACS91 | 0.045 U/mg |
| Mta99 | 0.0018 U/mg |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment demonstrates CO oxidation activity in recombinant *E. coli* with a much smaller amount in the negative controls. The small amount of CO oxidation ($CH_3$ viologen reduction) seen in the negative controls indicates that *E. coli* may have a limited ability to reduce $CH_3$ viologen.

Figure 9:
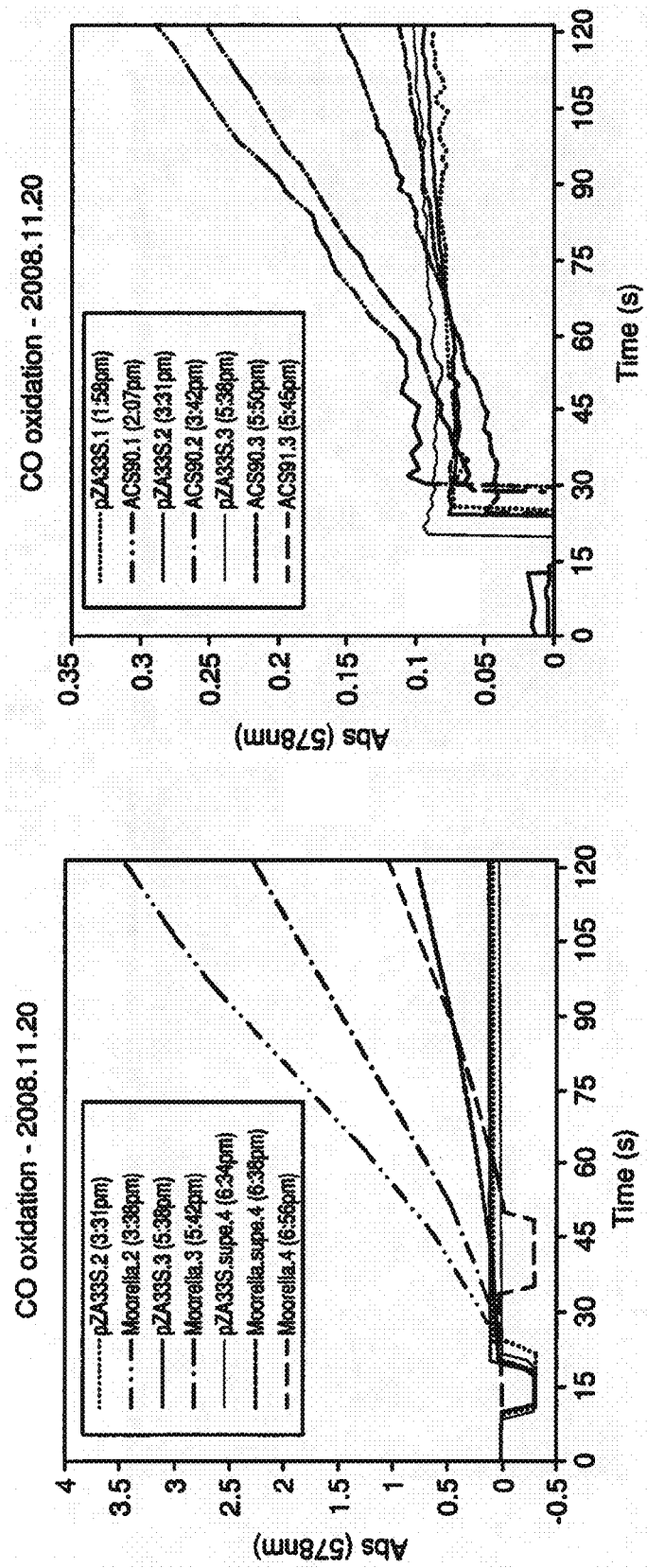
FIG. 9 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIG. 9. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 9. Briefly, cells (*M. thermoacetica* or *E. coli* with the CODH/ACS operon; ACS90 or ACS91 or empty vector: pZA33S) were grown and extracts prepared as described herein. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

EXAMPLE V

*E. coli* CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, $NiCl_2$, $Fe(II)NH_4SO_4$, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both $N_2$ and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. $N_2$ was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table II.

TABLE II

| Carbon Monoxide Concentrations, 36 hrs. | |
|---|---|
| Strain and Growth Conditions | Final CO concentration (micromolar) |
| pZA33-CO | 930 |
| ACS90-CO | 638 |
| | 494 |
| | 734 |
| | 883 |

TABLE II-continued

| Carbon Monoxide Concentrations, 36 hrs. | |
|---|---|
| Strain and Growth Conditions | Final CO concentration (micromolar) |
| ave | 687 |
| SD | 164 |
| ACS91-CO | 728 |
| | 812 |
| | 760 |
| | 611 |
| ave. | 728 |
| SD | 85 |

The results shown in Table II indicate that the cultures grew whether or not a strain was cultured in the presence of CO or not. These results indicate that *E. coli* can tolerate exposure to CO under anaerobic conditions and that *E. coli* cells expressing the CODH-ACS operon can metabolize some of the CO.

These results demonstrate that *E. coli* cells, whether expressing CODH/ACS or not, were able to grow in the presence of saturating amounts of CO. Furthermore, these grew equally well as the controls in nitrogen in place of CO. This experiment demonstrated that laboratory strains of *E. coli* are insensitive to CO at the levels achievable in a syngas project performed at normal atmospheric pressure. In addition, preliminary experiments indicated that the recombinant *E. coli* cells expressing CODH/ACS actually consumed some CO, probably by oxidation to carbon dioxide.

EXAMPLE VI

Exemplary Carboxylic Acid Reductases

This example describes the use of carboxylic acid reductases to carry out the conversion of a caroboxylic acid to an aldehyde.

1.2.1.e Acid Reductase. The conversion of unactivated acids to aldehydes can be carried out by an acid reductase. Examples of such conversions include, but are not limited, the conversion of 4-hydroxybutyrate, succinate, alpha-ketoglutarate, and 4-aminobutyrate to 4-hydroxybutanal, succinate semialdehyde, 2,5-dioxopentanoate, and 4-aminobutanal, respectively. One notable carboxylic acid reductase can be found in *Nocardia iowensis* which catalyzes the magnesium, ATP and NADPH-dependent reduction of carboxylic acids to their corresponding aldehydes (Venkitasubramanian et al., *J. Biol. Chem.* 282:478-485 (2007)). This enzyme is encoded by the car gene and was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Gene | Accession No. | GI No. | Organism |
|---|---|---|---|
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology.

| Gene | Accession No. | GI No. | Organism |
|---|---|---|---|
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6): 380-387 (2007)). Co-expression of griC and griD with SGR 665, an enzyme similar in sequence to the *Nocardia iowensis* npt, can be beneficial.

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene | Accession No. | GI No. | Organism |
|---|---|---|---|
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Cloning and Expression of Carboxylic Acid Reductase. *Escherichia coli* is used as a target organism to engineer the pathway for propylene. *E. coli* provides a good host for generating a non-naturally occurring microorganism capable of producing propylene. *E. coli* is amenable to genetic manipulation and is known to be capable of producing various intermediates and products effectively under various oxygenation conditions.

| Gene | Accession No. | GI No. | Organism |
|---|---|---|---|
| griC | 182438036 | YP_001825755.1 | Streptomyces griseus subsp. griseus NBRC 13350 |
| griD | 182438037 | YP_001825756.1 | Streptomyces griseus subsp. griseus NBRC 13350 |
| MSMEG_2956 | YP_887275.1 | YP_887275.1 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

To generate a microbial organism strain such as an *E. coli* strain engineered to produce propylene, nucleic acids encoding a carboxylic acid reductase and phosphopantetheine transferase are expressed in *E. coli* using well known molecular biology techniques (see, for example, Sambrook, supra, 2001; Ausubel supra, 1999). In particular, car genes from *Nocardia iowensis* (designated 720), *Mycobacterium smegmatis* mc(2)155 (designated 890), *Mycobacterium avium* subspecies *paratuberculosis* K-10 (designated 891) and *Mycobacterium marinum* M (designated 892) were cloned into pZS*13 vectors (Expressys, Ruelzheim, Germany)

under control of PA1/lac0 promoters. The npt (ABI83656.1) gene (i.e., 721) was cloned into the pKJL33S vector, a derivative of the original mini-F plasmid vector PML31 under control of promoters and ribosomal binding sites similar to those used in pZS*13.

The car gene (GNM_720) was cloned by PCR from *Nocardia* genomic DNA. Its nucleic acid and protein sequences are shown in FIGS. 10A and 10B, respectively. A codon-optimized version of the npt gene (GNM_721) was synthesized by GeneArt (Regensburg, Germany). Its nucleic acid and protein sequences are shown in FIGS. 11A and 11B, respectively. The nucleic acid and protein sequences for the *Mycobacterium smegmatis* mc(2)155 (designated 890), *Mycobacterium avium* subspecies *paratuberculosis* K-10 (designated 891) and *Mycobacterium marinum* M (designated 892) genes and enzymes can be found in FIGS. 12, 13, and 14, respectively. The plasmids are transformed into a host cell to express the proteins and enzymes required for propylene production.

Additional CAR variants were generated. A codon optimized version of CAR 891 was generated and designated 891 GA. The nucleic acid and amino acid sequences of CAR 891GA are shown in FIGS. 15A and 15B, respectively. Over 2000 CAR variants were generated. In particular, all 20 amino acid combinations were made at positions V295, M296, G297, G391, G421, D413, G414, Y415, G416, and S417, and additional variants were tested as well. Exemplary CAR variants include: E16K; Q95L; L100M; A1011T; K823E; T941S; H15Q; D198E; G446C; S392N; F699L; V883I; F467S; T987S; R12H; V295G; V295A; V295S; V295T; V295G; V295V; V295L; V295I; V295M; V295P; V295F; V295Y; V295W; V295D; V295E; V295N; V295Q; V295H; V295K; V295R; M296G; M296A; M296S; M296T; M296C; M296V; M296L; M296I; M296M; M296P; M296F; M296Y; M296W; M296D; M296E; M296N; M296Q; M296H; M296K; M296R; G297G; G297A; G297S; G297T; G297C; G297V; G297L; G297I; G297M; G297P; G297F; G297Y; G297W; G297D; G297E; G297N; G297Q; G297H; G297K; G297R; G391G; G391A; G391S; G391T; G391C; G391V; G391L; G391I; G391M; G391P; G391F; G391Y; G391W; G391D; G391E; G391N; G391Q; G391H; G391K; G391R; G421G; G421A; G421S; G421T; G421C; G421V; G421L; G421I G421M; G421P; G421F; G421Y; G421W; G421D; G421E; G421N; G421Q; G421H; G421K; G421R; D413G; D413A; D413S; D413T; D413C; D413V; D413L; D413I; D413M; D413P; D413F; D413Y; D413W; D413D; D413E; D413N; D413Q; D413H; D413K; D413R; G414G; G414A; G414S; G414T; G414C; G414V; G414L; G414I; G414M; G414P; G414F; G414Y; G414W; G414D; G414E; G414N; G414Q; G414H; G414K; G414R; Y415G; Y415A; Y415S; Y415T; Y415C; Y415V; Y415L; Y415I; Y415M; Y415P; Y415F; Y415Y; Y415W; Y415D; Y415E; Y415N; Y415Q; Y415H; Y415K; Y415R; G416G; G416A; G416S; G416T; G416C; G416V; G416L; G416I; G416M; G416P; G416F; G416Y; G416W; G416D; G416E; G416N; G416Q; G416H; G416K; G416R; S417G; S417A; S417S; S417T; S417C; S417V S417L; S417I; S417M; S417P; S417F; S417Y; S417W; S417D; S417E; S417N; S417Q; S417H; S417K; and S417R.

The CAR variants were screened for activity, and numerous CAR variants were found to exhibit CAR activity.

This example describes the use of CAR for converting carboxylic acids to aldehydes.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, comprising a microbial organism having a propylene pathway comprising at least one exogenous nucleic acid encoding a propylene pathway enzyme expressed in a sufficient amount to produce propylene; said non-naturally occurring microbial organism further comprising:
   (i) a reductive TCA pathway comprising at least one exogenous nucleic acid encoding a reductive TCA pathway enzyme, wherein said at least one exogenous nucleic acid is selected from an ATP-citrate lyase, citrate lyase, a citryl-CoA synthetase, a citryl-CoA lyase, a fumarate reductase, and an alpha-ketoglutarate:ferredoxin oxidoreductase;
   (ii) a reductive TCA pathway comprising at least one exogenous nucleic acid encoding a reductive TCA pathway enzyme, wherein said at least one exogenous nucleic acid is selected from a pyruvate:ferredoxin oxidoreductase, a phosphoenolpyruvate carboxylase, a phosphoenolpyruvate carboxykinase, a CO dehydrogenase, and an $H_2$ hydrogenase; or
   (iii) at least one exogenous nucleic acid encodes an enzyme selected from a CO dehydrogenase, an $H_2$ hydrogenase, and combinations thereof;
   wherein said propylene pathway comprises a pathway selected from:
   (a) a propylene forming enzyme and a 2-ketoglutarate methyltransferase; and
   (b) a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methy-2-ketoglutaconate reductase.

2. The non-naturally occurring microbial organism of claim 1, wherein said microbial organism comprising (i) further comprises an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof.

3. The non-naturally occurring microbial organism of claim 1, wherein said microbial organism comprising (ii) further comprises an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

4. The non-naturally occurring microbial organism of claim 1, wherein said microbial organism comprising (i) comprises three exogenous nucleic acids encoding an ATP-citrate lyase or a citrate lyase; a fumarate reductase; and an alpha-ketoglutarate:ferredoxin oxidoreductase;
   wherein said microbial organism comprising (ii) comprises four exogenous nucleic acids encoding a pyruvate:ferredoxin oxidoreductase; a phosphoenolpyruvate carboxylase or a phosphoenolpyruvate carboxykinase; a CO dehydrogenase; and an $H_2$ hydrogenase; or
   wherein said microbial organism comprising (iii) comprises two exogenous nucleic acids encoding a CO dehydrogenase and an $H_2$ hydrogenase.

5. The non-naturally occurring microbial organism of claim 1, wherein said microbial organism comprises two, three or four exogenous nucleic acids each encoding a propylene pathway enzyme.

6. The non-naturally occurring microbial organism of claim 5, wherein said microbial organism comprises:
   (a) two exogenous nucleic acids encoding a propylene forming enzyme and a 2-ketoglutarate methyltransferase; or
   (b) four exogenous nucleic acids encoding a propylene forming enzyme, a 4-hydroxy-4-methyl-2-ketoglutarate aldolase, a 4-hydroxy-4-methyl-2-ketoglutarate dehydratase II, a 4-hydroxy-4-methyl-2-ketoglutarate dehydratase I, a 4-methylene-2-ketoglutarate reductase, and a 4-methy-2-ketoglutaconate reductase.

7. The non-naturally occurring microbial organism of claim 1, wherein said at least one exogenous nucleic acid is a heterologous nucleic acid.

8. The non-naturally occurring microbial organism of claim 1, wherein said non-naturally occurring microbial organism is in a substantially anaerobic culture medium.

9. A method for producing propylene, comprising culturing the non-naturally occurring microbial organism of claim 1 under conditions and for a sufficient period of time to produce propylene.

10. The method of claim 9, wherein said non-naturally occurring microbial organism is in a substantially anaerobic culture medium.

* * * * *

```
                      SEQUENCE LISTING

<160> NUMBER OF SEQ ID NOS: 12

<210> SEQ ID NO 1
<211> LENGTH: 3525
<212> TYPE: DNA
<213> ORGANISM: Nocardia iowensis

<400> SEQUENCE: 1
atggcagtgg attcaccgga tgagcggcta cagcgccgca ttgcacagtt gtttgcagaa      60
gatgagcagg tcaaggccgc acgtccgctc gaagcggtga gcgcggcggt gagcgcgccc     120
ggtatgcggc tggcgcagat cgccgccact gttatggcgg gttacgccga ccgcccggcc     180
gccgggcagc gtgcgttcga actgaacacc gacgacgcga cgggccgcac ctcgctgcgg     240
ttacttcccc gattcgagac catcacctat cgcgaactgt ggcagcgagt cggcgaggtt     300
gccgcggcct ggcatcatga tcccgagaac ccttgcgcg caggtgattt cgtcgccctg     360
ctcggcttca ccagcatcga ctacgccacc ctcgacctgg ccgatatcca cctcggcgcg     420
gttaccgtgc cgttgcaggc cagcgcggcg gtgtcccagc tgatcgctat cctcaccgag     480
acttcgccgc ggctgctcgc ctcgaccccg gagcacctcg atgcggcggt cgagtgccta     540
ctcgcgggca ccacaccgga acgactgtg gtcttcgact accaccccga ggacgacgac     600
cagcgtgcgg ccttcgaatc cgcccgccgc cgccttgccg acgcgggcag cttggtgatc     660
```

-continued

```
gtcgaaacgc tcgatgccgt gcgtgcccgg ggccgcgact taccggccgc gccactgttc    720
gttcccgaca ccgacgacga cccgctggcc ctgctgatct acacctccgg cagcaccgga    780
acgccgaagg gcgcgatgta caccaatcgg ttggccgcca cgatgtggca ggggaactcg    840
atgctgcagg ggaactcgca acgggtcggg atcaatctca actacatgcc gatgagccac    900
atcgccggtc gcatatcgct gttcggcgtg ctcgctcgcg gtggcaccgc atacttcgcg    960
gccaagagcg acatgtcgac actgttcgaa gacatcggtc tggtacgtcc caccgagatc   1020
ttcttcgtcc cgcgcgtgtg cgacatggtc ttccagcgct atcagagcga gctggaccgg   1080
cgctcggtgg cgggcgccga cctggacacg ctcgatcggg aagtgaaagc cgacctccgg   1140
cagaactacc tcggtgggcg cttcctggtg gcggtcgtcg gcagcgcgcc gctggccgcg   1200
gagatgaaga cgttcatgga gtccgtcctc gatctgccac tgcacgacgg gtacgggtcg   1260
accgaggcgg gcgcaagcgt gctgctcgac aaccagatcc agcggccgcc ggtgctcgat   1320
tacaagctcg tcgacgtgcc cgaactgggt tacttccgca ccgaccggcc gcatccgcgc   1380
ggtgagctgt tgttgaaggc ggagaccacg attccgggct actacaagcg gcccgaggtc   1440
accgcggaga tcttcgacga ggacggcttc tacaagaccg gcgatatcgt ggccgagctc   1500
gagcacgatc ggctggtcta tgtcgaccgt cgcaacaatg tgctcaaact gtcgcagggc   1560
gagttcgtga ccgtcgccca tctcgaggcc gtgttcgcca gcagcccgct gatccggcag   1620
atcttcatct acggcagcag cgaacgttcc tatctgctcg cggtgatcgt ccccaccgac   1680
gacgcgctgc gcggccgcga caccgccacc ttgaaatcgg cactggccga atcgattcag   1740
cgcatcgcca aggacgcgaa cctgcagccc tacgagattc cgcgcgattt cctgatcgag   1800
accgagccgt tcaccatcgc caacggactg ctctccggca tcgcgaagct gctgcgcccc   1860
aatctgaagg aacgctacgg cgctcagctg gagcagatgt acaccgatct cgcgacaggc   1920
caggccgatg agctgctcgc cctgcgccgc gaagccgccg acctgccggt gctcgaaacc   1980
gtcagccggg cagcgaaagc gatgctcggc gtcgcctccg ccgatatgcg tcccgacgcg   2040
cacttcaccg acctgggcgg cgattcccctt tccgcgctgt cgttctcgaa cctgctgcac   2100
gagatcttcg gggtcgaggt gccggtgggt gtcgtcgtca gcccggcgaa cgagctgcgc   2160
gatctggcga attacattga ggcggaacgc aactcgggcg cgaagcgtcc caccttcacc   2220
tcggtgcacg gcggcggttc cgagatccgc gccgccgatc tgaccctcga caagttcatc   2280
gatgcccgca ccctggccgc cgccgacagc attccgcacg cgccggtgcc agcgcagacg   2340
gtgctgctga ccgcgcgcaa cggctacctc ggccggttcc tgtgcctgga atggctggag   2400
cggctggaca agacgggtgg cacgctgatc tgcgtcgtgc gcggtagtga cgcggccgcg   2460
gcccgtaaac ggctggactc ggcgttcgac agcggcgatc ccggcctgct cgagcactac   2520
cagcaactgg ccgcacggac cctggaagtc ctcgccggtg atatcggcga cccgaatctc   2580
ggtctggacg acgcgacttg gcagcggttg ccgaaaccg tcgacctgat cgtccatccc   2640
gccgcgttgg tcaaccacgt ccttccctac acccagctgt tcggccccaa tgtcgtcggc   2700
accgccgaaa tcgtccggtt ggcgatcacg gcgcggcgca agccggtcac ctacctgtcg   2760
accgtcggag tggccgacca ggtcgacccg gcggagtatc aggaggacag cgacgtccgc   2820
gagatgagcg cggtgcgcgt cgtgcgcgag agttacgcca acggctacgg caacagcaag   2880
tgggcggggg aggtcctgct gcgcgaagca cacgatctgt gtggcttgcc ggtcgcggtg   2940
ttccgttcgg acatgatcct ggcgcacagc cggtacgcgg gtcagctcaa cgtccaggac   3000
gtgttcaccc ggctgatcct cagcctggtc gccaccggca tcgcgccgta ctcgttctac   3060
```

-continued

```
cgaaccgacg cggacggcaa ccggcagcgg gcccactatg acggcttgcc ggcggacttc    3120
acggcggcgg cgatcaccgc gctcggcatc aagccaccg aaggcttccg gacctacgac     3180
gtgctcaatc cgtacgacga tggcatctcc ctcgatgaat cgtcgactg gctcgtcgaa     3240 tccggccacc cgatccagcg catcaccgac tacagcgact ggttccaccg tttcgagacg    3300
gcgatccgcg cgctgccgga aaagcaacgc caggcctcgg tgctgccgtt gctggacgcc   3360
taccgcaacc cctgcccggc ggtccgcggc gcgatactcc cggccaagga gttccaagcg   3420
gcggtgcaaa cagccaaaat cggtccggaa caggacatcc cgcatttgtc cgcgccactg   3480
atcgataagt acgtcagcga tctggaactg cttcagctgc tctaa                   3525
```

<210> SEQ ID NO 2
<211> LENGTH: 1174
<212> TYPE: PRT
<213> ORGANISM: Nocardia iowensis

<400> SEQUENCE: 2

```
Met Ala Val Asp Ser Pro Asp Glu Arg Leu Gln Arg Ile Ala Gln
  1               5                  10                  15

Leu Phe Ala Glu Asp Glu Gln Val Lys Ala Ala Arg Pro Leu Glu Ala
                 20                  25                  30

Val Ser Ala Ala Val Ser Ala Pro Gly Met Arg Leu Ala Gln Ile Ala
             35                  40                  45

Ala Thr Val Met Ala Gly Tyr Ala Asp Arg Pro Ala Ala Gly Gln Arg
         50                  55                  60

Ala Phe Glu Leu Asn Thr Asp Asp Ala Thr Gly Arg Thr Ser Leu Arg
 65                  70                  75                  80

Leu Leu Pro Arg Phe Glu Thr Ile Thr Tyr Arg Glu Leu Trp Gln Arg
                 85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
    290                 295                 300
```

```
Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
            355                 360                 365

Asp Thr Leu Asp Arg Glu Val Lys Ala Asp Leu Arg Gln Asn Tyr Leu
        370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
            435                 440                 445

Leu Gly Tyr Phe Arg Thr Asp Arg Pro His Pro Arg Gly Glu Leu Leu
        450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
        690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
```

-continued

```
              725                 730                 735
Pro Thr Phe Thr Ser Val His Gly Gly Gly Ser Glu Ile Arg Ala Ala
                740                 745                 750
Asp Leu Thr Leu Asp Lys Phe Ile Asp Ala Arg Thr Leu Ala Ala Ala
                755                 760                 765
Asp Ser Ile Pro His Ala Pro Val Pro Ala Gln Thr Val Leu Leu Thr
770                 775                 780
Gly Ala Asn Gly Tyr Leu Gly Arg Phe Leu Cys Leu Glu Trp Leu Glu
785                 790                 795                 800
Arg Leu Asp Lys Thr Gly Gly Thr Leu Ile Cys Val Val Arg Gly Ser
                805                 810                 815
Asp Ala Ala Ala Arg Lys Arg Leu Asp Ser Ala Phe Asp Ser Gly
                820                 825                 830
Asp Pro Gly Leu Leu Glu His Tyr Gln Gln Leu Ala Ala Arg Thr Leu
                835                 840                 845
Glu Val Leu Ala Gly Asp Ile Gly Asp Pro Asn Leu Gly Leu Asp Asp
                850                 855                 860
Ala Thr Trp Gln Arg Leu Ala Glu Thr Val Asp Leu Ile Val His Pro
865                 870                 875                 880
Ala Ala Leu Val Asn His Val Leu Pro Tyr Thr Gln Leu Phe Gly Pro
                885                 890                 895
Asn Val Val Gly Thr Ala Glu Ile Val Arg Leu Ala Ile Thr Ala Arg
                900                 905                 910
Arg Lys Pro Val Thr Tyr Leu Ser Thr Val Gly Val Ala Asp Gln Val
                915                 920                 925
Asp Pro Ala Glu Tyr Gln Glu Asp Ser Asp Val Arg Glu Met Ser Ala
                930                 935                 940
Val Arg Val Arg Glu Ser Tyr Ala Asn Gly Tyr Gly Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Ser Asp Met Ile Leu Ala His Ser Arg Tyr
                980                 985                 990
Ala Gly Gln Leu Asn Val Gln Asp Val Phe Thr Arg Leu Ile Leu Ser
                995                 1000                1005
Leu Val Ala Thr Gly Ile Ala Pro Tyr Ser Phe Tyr Arg Thr Asp
                1010                1015                1020
Ala Asp Gly Asn Arg Gln Arg Ala His Tyr Asp Gly Leu Pro Ala
                1025                1030                1035
Asp Phe Thr Ala Ala Ala Ile Thr Ala Leu Gly Ile Gln Ala Thr
                1040                1045                1050
Glu Gly Phe Arg Thr Tyr Asp Val Leu Asn Pro Tyr Asp Asp Gly
                1055                1060                1065
Ile Ser Leu Asp Glu Phe Val Asp Trp Leu Val Glu Ser Gly His
                1070                1075                1080
Pro Ile Gln Arg Ile Thr Asp Tyr Ser Asp Trp Phe His Arg Phe
                1085                1090                1095
Glu Thr Ala Ile Arg Ala Leu Pro Glu Lys Gln Arg Gln Ala Ser
                1100                1105                1110
Val Leu Pro Leu Leu Asp Ala Tyr Arg Asn Pro Cys Pro Ala Val
                1115                1120                1125
Arg Gly Ala Ile Leu Pro Ala Lys Glu Phe Gln Ala Ala Val Gln
                1130                1135                1140
```

Thr Ala Lys Ile Gly Pro Glu Gln Asp Ile Pro His Leu Ser Ala
1145                1150                1155

Pro Leu Ile Asp Lys Tyr Val Ser Asp Leu Glu Leu Leu Gln Leu
1160                1165                1170

Leu

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      codon optimized phosphpantetheine transferase
      polynucleotide

<400> SEQUENCE: 3

```
atgattgaaa ccattctgcc tgcaggcgtt gaaagcgcag aactgctgga atatccggaa      60
gatctgaaag cacatccggc agaagaacat ctgattgcca aaagcgttga aaaacgtcgt     120
cgtgatttta ttggtgcacg tcattgtgca cgtctggcac tggcagaact gggtgaacct     180
ccggttgcaa ttggtaaagg tgaacgtggt gcaccgattt ggcctcgtgg tgttgttggt     240
agcctgaccc attgtgatgg ttatcgtgca gcagcagttg cacataaaat gcgctttcgc     300
agcattggta ttgatgcaga accgcatgca ccctgccgg aaggtgttct ggatagcgtt     360
agcctgccgc cggaacgtga atggctgaaa accaccgata gcgcactgca tctggatcgt     420
ctgctgtttt gtgcaaaaga agccaccttat aaagcctggt ggccgctgac agcacgttgg     480
ctgggttttg aagaagccca tattaccttt gaaattgaag atggtagcgc agatagcggt     540
aatggcacct ttcatagcga actgctggtt ccgggtcaga ccaatgatgg tggtacaccg     600
ctgctgagct ttgatggtcg ttggctgatt gcagatggtt ttattctgac cgcaattgcc     660
tatgcctaa                                                             669
```

<210> SEQ ID NO 4
<211> LENGTH: 222
<212> TYPE: PRT
<213> ORGANISM: Artificial Sequence
<220> FEATURE:
<223> OTHER INFORMATION: Description of Artificial Sequence: Synthetic
      codon optimized phosphpantetheine transferase
      polypeptide

<400> SEQUENCE: 4

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Arg Asp Phe Ile Gly Ala Arg His
        35                  40                  45

Cys Ala Arg Leu Ala Leu Ala Glu Leu Gly Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Ala Val Ala His Lys
                85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Glu Arg Glu Trp
        115                 120                 125

```
Leu Lys Thr Thr Asp Ser Ala Leu His Leu Asp Arg Leu Leu Phe Cys
        130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
        210                 215                 220

<210> SEQ ID NO 5
<211> LENGTH: 3522
<212> TYPE: DNA
<213> ORGANISM: Mycobacterium smegmatis

<400> SEQUENCE: 5
atgaccagcg atgttcacga cgccacagac ggcgtcaccg aaaccgcact cgacgacgag      60
cagtcgaccc gccgcatcgc cgagctgtac gccaccgatc ccgagttcgc cgccgccgca     120
ccgttgcccg ccgtggtcga cgcggcgcac aaacccgggc tgcggctggc agagatcctg     180
cagaccctgt tcaccggcta cggtgaccgc ccggcgctgg ataccgcgc cgtgaactg      240 gccaccgacg agggcgggcg caccgtgacg cgtctgctgc gcggttcga cccctcacc      300 tacgcccagg tgtggtcgcg cgtgcaagcg gtcgccgcgg ccctgcgcca caacttcgcg     360
cagccgatct accccggcga cgccgtcgcg acgatcggtt cgcgagtcc cgattacctg     420 acgctggatc tcgtatgcgc ctacctgggc tcgtgagtg ttccgctgca gcacaacgca     480
ccggtcagcc ggctcgcccc gatcctggcc gaggtcgaac gcggatcct caccgtgagc     540 gccgaatacc tcgacctcgc agtcgaatcc gtgcgggacg tcaactcggt gtcgcagctc     600
gtggtgttcg accatcaccc cgaggtcgac gaccaccgcg acgcactggc ccgcgcgcgt     660
gaacaactcg ccggcaaggg catcgccgtc accaccctgg acgcgatcgc cgacgagggc     720
gccgggctgc cggccgaacc gatctacacc gccgaccatg atcagcgcct cgcgatgatc     780
ctgtacacct cgggttccac cggcgcacc aagggtgcga tgtacaccga ggcgatggtg     840
gcgcggctgt ggaccatgtc gttcatcacg ggtgacccca cgccggtcat caacgtcaac     900
ttcatgccgc tcaaccacct gggcgggcgc atccccattt ccaccgccgt gcagaacggt     960
ggaaccagtt acttcgtacc ggaatccgac atgtccacgc tgttcgagga tctcgcgctg    1020
gtgcgcccga ccgaactcgg cctggttccg cgcgtcgccg acatgctcta ccagcaccac    1080
ctcgccaccg tcgaccgcct ggtcacgcag ggcgccgacg aactgaccgc cgagaagcag    1140
gccggtgccg aactgcgtga gcaggtgctc ggcgacgcg tgatcaccgg attcgtcagc    1200
accgcaccgc tggccgcgga tgagggcg ttcctcgaca tcaccctggg cgcacacatc    1260
gtcgacggct acgggctcac cgagaccggc gccgtgacac gcgacggtgt gatcgtgcgg    1320
ccaccggtga tcgactacaa gctgatcgac gttcccgaac tcggctactt cagcaccgac    1380
aagccctacc gcgtggcga actgctggtc aggtcgcaaa cgctgactcc cgggtactac    1440
aagcgccccg aggtcaccgc gagcgtcttc gaccgggacg gctactacca caccggcgac    1500
gtcatggccg agaccgcacc cgaccacctg gtgtacgtgg accgtcgcaa caacgtcctc    1560
aaactcgcgc agggcgagtt cgtggcggtc gccaacctgg aggcggtgtt ctccggcgcg    1620
```

```
gcgctggtgc gccagatctt cgtgtacggc aacagcgagc gcagtttcct tctggccgtg    1680
gtggtcccga cgccggaggc gctcgagcag tacgatccgg ccgcgctcaa ggccgcgctg    1740
gccgactcgc tgcagcgcac cgcacgcgac gccgaactgc aatcctacga ggtgccggcc    1800
gatttcatcg tcgagaccga ccgttcagc gccgccaacg gctgctgtc gggtgtcgga     1860
aaactgctgc ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg gagcgaggtg    2040
gcatccgacg cccacttcac cgacctgggc ggggattccc tgtcggcgct gacactttcg    2100
aacctgctga gcgatttctt cggtttcgaa gttcccgtcg caccatcgt gaacccggcc     2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cgggtctgcc caaggtcacc    2340
accgagccac ggacggtgtt gctctcgggc gccaacggct ggctgggccg gttcctcacg    2400
ttgcagtggc tggaacgcct ggcacctgtc ggcggcaccc tcatcacgat cgtgcggggc    2460
cgcgacgacg ccgcggcccg cgcacggctg acccaggcct acgacaccga tcccgagttg    2520
tcccgccgct tcgccgagct ggccgaccgc cacctgcggg tggtcgccgg tgacatcggc    2580
gacccgaatc tgggcctcac acccgagatc tggcaccggc tcgccgccga ggtcgacctg    2640
gtggtgcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatcccg acttcgagga ggacggcgac     2820
atccggaccg tgagcccggt gcgccgctc gacggcggat acgccaacgg ctacggcaac      2880
agcaagtggg ccggcgaggt gctgctgcgg gaggcccacg atctgtgcgg gctgcccgtg    2940
gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg gagacggtga gcgccgcgg gcgcactacc ccggcctgac ggtcgatttc      3120
gtggccgagg cggtcacgac gctcggcgcg cagcagcgcg agggatacgt gtcctacgac    3180
gtgatgaacc gcacgacga cgggatctcc ctggatgtgt cgtggactg gctgatccgg       3240
gcgggccatc cgatcgaccg ggtcgacgac tacgacgact gggtgcgtcg gttcgagacc    3300
gcgttgaccg cgcttcccga aagcgccgc gcacagaccg tactgccgct gctgcacgcg     3360
ttccgcgctc cgcaggcacc gttgcgcggc cacccgaac ccacggaggt gttccacgcc     3420
gcggtgcgca ccgcgaaggt gggcccggga gacatcccgc acctcgacga ggcgctgatc    3480
gacaagtaca tacgcgatct gcgtgagttc ggtctgatct aa                        3522
```

<210> SEQ ID NO 6
<211> LENGTH: 1173
<212> TYPE: PRT
<213> ORGANISM: Mycobacterium smegmatis

<400> SEQUENCE: 6

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45
```

```
Ala His Lys Pro Gly Leu Arg Leu Ala Glu Ile Leu Gln Thr Leu Phe
     50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
    450                 455                 460

Arg Gly Glu Leu Leu Val Arg Ser Gln Thr Leu Thr Pro Gly Tyr Tyr
```

```
                465                 470                 475                 480
Lys Arg Pro Glu Val Thr Ala Ser Val Phe Asp Arg Asp Gly Tyr Tyr
                    485                 490                 495

His Thr Gly Asp Val Met Ala Glu Thr Ala Pro Asp His Leu Val Tyr
                    500                 505                 510

Val Asp Arg Arg Asn Asn Val Leu Lys Leu Ala Gln Gly Glu Phe Val
                    515                 520                 525

Ala Val Ala Asn Leu Glu Ala Val Phe Ser Gly Ala Ala Leu Val Arg
                    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                    565                 570                 575

Lys Ala Ala Leu Ala Asp Ser Leu Gln Arg Thr Ala Arg Asp Ala Glu
                    580                 585                 590

Leu Gln Ser Tyr Glu Val Pro Ala Asp Phe Ile Val Glu Thr Glu Pro
                    595                 600                 605

Phe Ser Ala Ala Asn Gly Leu Leu Ser Gly Val Gly Lys Leu Leu Arg
                    610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                    645                 650                 655

Ala Ala Thr Gln Pro Val Ile Asp Thr Leu Thr Gln Ala Ala Ala Thr
                    660                 665                 670

Ile Leu Gly Thr Gly Ser Glu Val Ala Ser Asp Ala His Phe Thr Asp
                    675                 680                 685

Leu Gly Gly Asp Ser Leu Ser Ala Leu Thr Leu Ser Asn Leu Leu Ser
                    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                    725                 730                 735

Gly Asp Arg Arg Pro Ser Phe Thr Thr Val His Gly Ala Asp Ala Thr
                    740                 745                 750

Glu Ile Arg Ala Ser Glu Leu Thr Leu Asp Lys Phe Ile Asp Ala Glu
                    755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                    805                 810                 815

Ile Val Arg Gly Arg Asp Asp Ala Ala Ala Arg Ala Arg Leu Thr Gln
                    820                 825                 830

Ala Tyr Asp Thr Asp Pro Glu Leu Ser Arg Arg Phe Ala Glu Leu Ala
                    835                 840                 845

Asp Arg His Leu Arg Val Val Ala Gly Asp Ile Gly Asp Pro Asn Leu
                    850                 855                 860

Gly Leu Thr Pro Glu Ile Trp His Arg Leu Ala Ala Glu Val Asp Leu
865                 870                 875                 880

Val Val His Pro Ala Ala Leu Val Asn His Val Leu Pro Tyr Arg Gln
                    885                 890                 895
```

Leu Phe Gly Pro Asn Val Val Gly Thr Ala Glu Val Ile Lys Leu Ala
900 905 910

Leu Thr Glu Arg Ile Lys Pro Val Thr Tyr Leu Ser Thr Val Ser Val
915 920 925

Ala Met Gly Ile Pro Asp Phe Glu Glu Asp Gly Asp Ile Arg Thr Val
930 935 940

Ser Pro Val Arg Pro Leu Asp Gly Gly Tyr Ala Asn Gly Tyr Gly Asn
945 950 955 960

Ser Lys Trp Ala Gly Glu Val Leu Leu Arg Glu Ala His Asp Leu Cys
965 970 975

Gly Leu Pro Val Ala Thr Phe Arg Ser Asp Met Ile Leu Ala His Pro
980 985 990

Arg Tyr Arg Gly Gln Val Asn Val Pro Asp Met Phe Thr Arg Leu Leu
995 1000 1005

Leu Ser Leu Leu Ile Thr Gly Val Ala Pro Arg Ser Phe Tyr Ile
1010 1015 1020

Gly Asp Gly Glu Arg Pro Arg Ala His Tyr Pro Gly Leu Thr Val
1025 1030 1035

Asp Phe Val Ala Glu Ala Val Thr Thr Leu Gly Ala Gln Gln Arg
1040 1045 1050

Glu Gly Tyr Val Ser Tyr Asp Val Met Asn Pro His Asp Asp Gly
1055 1060 1065

Ile Ser Leu Asp Val Phe Val Asp Trp Leu Ile Arg Ala Gly His
1070 1075 1080

Pro Ile Asp Arg Val Asp Asp Tyr Asp Asp Trp Val Arg Arg Phe
1085 1090 1095

Glu Thr Ala Leu Thr Ala Leu Pro Glu Lys Arg Arg Ala Gln Thr
1100 1105 1110

Val Leu Pro Leu Leu His Ala Phe Arg Ala Pro Gln Ala Pro Leu
1115 1120 1125

Arg Gly Ala Pro Glu Pro Thr Glu Val Phe His Ala Ala Val Arg
1130 1135 1140

Thr Ala Lys Val Gly Pro Gly Asp Ile Pro His Leu Asp Glu Ala
1145 1150 1155

Leu Ile Asp Lys Tyr Ile Arg Asp Leu Arg Glu Phe Gly Leu Ile
1160 1165 1170

<210> SEQ ID NO 7
<211> LENGTH: 3522
<212> TYPE: DNA
<213> ORGANISM: Mycobacterium avium

<400> SEQUENCE: 7
atgtcgactg ccacccatga cgaacgactc gaccgtcgcg tccacgaact catcgccacc 60
gacccgcaat tcgccgccgc ccaacccgac ccggcgatca ccgccgccct cgaacagccc 120
gggctgcggc tgccgcagat catccgcacc gtgctcgacg gctacgccga ccggccggcg 180
ctgggacagc gcgtggtgga gttcgtcacg gacgccaaga ccgggcgcac gtcggcgcag 240
ctgctccccc gcttcgagac catcacgtac agcgaagtag cgcagcgtgt ttcggcgctg 300
ggccgcgccc tgtccgacga cgcggtgcac cccggcgacc gggtgtgcgt gctgggcttc 360
aacagcgtcg actacgccac catcgacatg gcgctgggcg ccatcggcgc cgtctcggtg 420
ccgctgcaga ccagcgcggc aatcagctcg ctgcagccga tcgtggccga gaccgagccc 480
accctgatcg cgtccagcgt gaaccagctg tccgacgcgg tgcagctgat caccggcgcc 540

| | |
|---|---|
| gagcaggcgc ccacccggct ggtggtgttc gactaccacc cgcaggtcga cgaccagcgc | 600 |
| gaggccgtcc aggacgccgc ggcgcggctg tccagcaccg gcgtggccgt ccagacgctg | 660 |
| gccgagctgc tggagcgcgg caaggacctg cccgccgtcg cggagccgcc cgccgacgag | 720 |
| gactcgctgg ccctgctgat ctacacctcc gggtccaccg cgcccccaa gggcgcgatg | 780 |
| tacccacaga gcaacgtcgg caagatgtgg cgccgcggca gcaagaactg gttcggcgag | 840 |
| agcgccgcgt cgatcaccct gaacttcatg ccgatgagcc acgtgatggg ccgaagcatc | 900 |
| ctctacggca cgctgggcaa cggcggcacc gcctacttcg ccgcccgcag cgacctgtcc | 960 |
| accctgcttg aggacctcga gctggtgcgc cccaccgagc tcaacttcgt cccgcggatc | 1020 |
| tgggagacgc tgtacggcga attccagcgt caggtcgagc ggcggctctc cgaggccggg | 1080 |
| gacgccggcg aacgtcgcgc cgtcgaggcc gaggtgctgg ccgagcagcg ccagtacctg | 1140 |
| ctgggcgggc ggttcaccct cgcgatgacg ggctcggcgc ccatctcgcc ggagctgcgc | 1200 |
| aactgggtcg agtcgctgct cgaaatgcac ctgatggacg gctacggctc caccgaggcc | 1260 |
| ggaatggtgt tgttcgacgg ggagattcag cgcccgccgg tgatcgacta caagctggtc | 1320 |
| gacgtgccgg acctgggcta cttcagcacc gaccggccgc atccgcgcgg cgagctgctg | 1380 |
| ctgcgcaccg agaacatgtt cccgggctac tacaagcggg ccgaaaccac cgcgggcgtc | 1440 |
| ttcgacgagg acggctacta ccgcaccggc gacgtgttcg ccgagatcgc cccggaccgg | 1500 |
| ctggtctacg tcgaccgccg caacaacgtg ctcaagctgg cgcagggcga attcgtcacg | 1560 |
| ctggccaagc tggaggcggt gttcggcaac agcccgctga tccgccagat ctacgtctac | 1620 |
| ggcaacagcg cccagcccta cctgctggcg gtcgtggtgc ccaccgagga ggcgctggcc | 1680 |
| tcgggtgacc ccgagacgct caagcccaag atcgccgact cgctgcagca ggtcgccaag | 1740 |
| gaggccggcc tgcagtccta cgaggtgccg cgcgacttca tcatcgagac cacccgttc | 1800 |
| agcctggaaa acgtctgct gaccgggatc cggaagctgg cgtggccgaa actgaagcag | 1860 |
| cactacgggg aacggctgga gcagatgtac gccgacctgg ccgccggaca ggccaacgag | 1920 |
| ctggccgagc tgcgccgcaa cggtgcccag gcgccggtgt tgcagaccgt gagccgcgcc | 1980 |
| gcgggcgcca tgctgggttc ggccgcctcc gacctgtccc ccgacgccca cttcaccgat | 2040 |
| ctgggcggag actcgttgtc ggcgttgaca ttcggcaacc tgctgcgcga tcttcgac | 2100 |
| gtcgacgtgc cggtaggcgt gatcgtcagc ccggccaacg acctggcggc catcgcgagc | 2160 |
| tacatcgagg ccgagcggca gggcagcaag cgcccgacgt cgcctcggt gcacggccgg | 2220 |
| gacgcgaccg tggtgcgcgc cgccgacctg acgctgggca agttcctcga cgccgagacg | 2280 |
| ctggccgccg cgccgaacct gcccaagccg gccaccgagg tgcgcaccgt gctgctgacc | 2340 |
| ggcgccaccg gcttcctggg ccgctacctg gccctggaat ggctggagcg gatggacatg | 2400 |
| gtggacggca aggtcatcgc cctggtccgg gccgctccg acgaggaggc acgcgcccgg | 2460 |
| ctggacaaga ccttcgacag cggcgacccg aaactgctcg cgcactacca gcagctggcc | 2520 |
| gccgatcacc tggaggtcat cgccggcgac aagggcgagg ccaatctggg cctgggccaa | 2580 |
| gacgtttggc aacgactggc cgacacggtc gacgtgatcg tcgacccgc cgcgctggtc | 2640 |
| aaccacgtgt tgccgtacag cgagctgttc gggcccaacg ccctgggcac cgcggagctg | 2700 |
| atccggctgg cgctgacgtc caagcagaag ccgtacacct acgtgtccac catcggcgtg | 2760 |
| ggcgaccaga tcgagccggg caagttcgtc gagaacgccg acatccggca gatgagcgcc | 2820 |
| acccgggcga tcaacgacag ctacgccaac ggctatggca acagcaagtg ggccggcgag | 2880 |
| gtgctgctgc gcgaggcgca cgacctgtgc gggctgcccg tcgcggtgtt ccgctgcgac | 2940 |

```
atgatcctgg ccgacaccac gtatgccggg cagctcaacc tgccggacat gttcacccgg      3000
ctgatgctga gcctggtggc caccgggatc gcgcccggct cgttctacga gctcgacgcc      3060
gacggcaacc ggcagcgggc gcactacgac ggcctgccgg tcgagttcat cgccgcggcg      3120
atctcgacgc tgggttcgca gatcaccgac agcgacaccg gcttccagac ctaccacgtg      3180
atgaacccct acgatgacgg cgtcggtctg gacgagtacg tcgattggct ggtggacgcc      3240
ggctattcga tcgagcggat cgccgactac tccgaatggc tgcggcggtt cgagacctcg      3300
ctgcgggccc tgccggaccg gcagcgccag tactcgctgc tgccgctgct gcacaactac      3360
cgcacgccgg agaagccgat caacgggtcg atagctccca ccgacgtgtt ccgggcagcg      3420
gtgcaggagg cgaaaatcgg ccccgacaaa gacattccgc acgtgtcgcc gccggtcatc      3480
gtcaagtaca tcaccgacct gcagctgctc gggctgctct aa                        3522
```

<210> SEQ ID NO 8
<211> LENGTH: 1173
<212> TYPE: PRT
<213> ORGANISM: Mycobacterium avium

<400> SEQUENCE: 8

```
Met Ser Thr Ala Thr His Asp Glu Arg Leu Asp Arg Arg Val His Glu
1               5                   10                  15

Leu Ile Ala Thr Asp Pro Gln Phe Ala Ala Gln Pro Asp Pro Ala
            20                  25                  30

Ile Thr Ala Ala Leu Glu Gln Pro Gly Leu Arg Leu Pro Gln Ile Ile
        35                  40                  45

Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
        115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205

Arg Leu Ser Ser Thr Gly Val Ala Val Gln Thr Leu Ala Glu Leu Leu
    210                 215                 220

Glu Arg Gly Lys Asp Leu Pro Ala Val Ala Glu Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
```

```
                 275                 280                 285
Phe Met Pro Met Ser His Val Met Gly Arg Ser Ile Leu Tyr Gly Thr
290                 295                 300
Leu Gly Asn Gly Gly Thr Ala Tyr Phe Ala Ala Arg Ser Asp Leu Ser
305                 310                 315                 320
Thr Leu Leu Glu Asp Leu Glu Leu Val Arg Pro Thr Glu Leu Asn Phe
                325                 330                 335
Val Pro Arg Ile Trp Glu Thr Leu Tyr Gly Glu Phe Gln Arg Gln Val
                340                 345                 350
Glu Arg Arg Leu Ser Glu Ala Gly Asp Ala Gly Glu Arg Arg Ala Val
            355                 360                 365
Glu Ala Glu Val Leu Ala Glu Gln Arg Gln Tyr Leu Leu Gly Gly Arg
370                 375                 380
Phe Thr Phe Ala Met Thr Gly Ser Ala Pro Ile Ser Pro Glu Leu Arg
385                 390                 395                 400
Asn Trp Val Glu Ser Leu Leu Glu Met His Leu Met Asp Gly Tyr Gly
                405                 410                 415
Ser Thr Glu Ala Gly Met Val Leu Phe Asp Gly Glu Ile Gln Arg Pro
                420                 425                 430
Pro Val Ile Asp Tyr Lys Leu Val Asp Val Pro Asp Leu Gly Tyr Phe
            435                 440                 445
Ser Thr Asp Arg Pro His Pro Arg Gly Glu Leu Leu Leu Arg Thr Glu
        450                 455                 460
Asn Met Phe Pro Gly Tyr Tyr Lys Arg Ala Glu Thr Thr Ala Gly Val
465                 470                 475                 480
Phe Asp Glu Asp Gly Tyr Tyr Arg Thr Gly Asp Val Phe Ala Glu Ile
                485                 490                 495
Ala Pro Asp Arg Leu Val Tyr Val Asp Arg Arg Asn Asn Val Leu Lys
                500                 505                 510
Leu Ala Gln Gly Glu Phe Val Thr Leu Ala Lys Leu Glu Ala Val Phe
            515                 520                 525
Gly Asn Ser Pro Leu Ile Arg Gln Ile Tyr Val Tyr Gly Asn Ser Ala
530                 535                 540
Gln Pro Tyr Leu Leu Ala Val Val Pro Thr Glu Glu Ala Leu Ala
545                 550                 555                 560
Ser Gly Asp Pro Glu Thr Leu Lys Pro Lys Ile Ala Asp Ser Leu Gln
                565                 570                 575
Gln Val Ala Lys Glu Ala Gly Leu Gln Ser Tyr Glu Val Pro Arg Asp
            580                 585                 590
Phe Ile Ile Glu Thr Thr Pro Phe Ser Leu Glu Asn Gly Leu Leu Thr
            595                 600                 605
Gly Ile Arg Lys Leu Ala Trp Pro Lys Leu Lys Gln His Tyr Gly Glu
        610                 615                 620
Arg Leu Glu Gln Met Tyr Ala Asp Leu Ala Ala Gly Gln Ala Asn Glu
625                 630                 635                 640
Leu Ala Glu Leu Arg Arg Asn Gly Ala Gln Ala Pro Val Leu Gln Thr
                645                 650                 655
Val Ser Arg Ala Ala Gly Ala Met Leu Gly Ser Ala Ala Ser Asp Leu
            660                 665                 670
Ser Pro Asp Ala His Phe Thr Asp Leu Gly Gly Asp Ser Leu Ser Ala
        675                 680                 685
Leu Thr Phe Gly Asn Leu Leu Arg Glu Ile Phe Asp Val Asp Val Pro
    690                 695                 700
```

-continued

Val Gly Val Ile Val Ser Pro Ala Asn Asp Leu Ala Ile Ala Ser
705                 710                 715                 720

Tyr Ile Glu Ala Glu Arg Gln Gly Ser Lys Arg Pro Thr Phe Ala Ser
            725                 730                 735

Val His Gly Arg Asp Ala Thr Val Val Arg Ala Ala Asp Leu Thr Leu
        740                 745                 750

Asp Lys Phe Leu Asp Ala Glu Thr Leu Ala Ala Pro Asn Leu Pro
    755                 760                 765

Lys Pro Ala Thr Glu Val Arg Thr Val Leu Leu Thr Gly Ala Thr Gly
770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
            805                 810                 815

Ala Arg Ala Arg Leu Asp Lys Thr Phe Asp Ser Gly Asp Pro Lys Leu
            820                 825                 830

Leu Ala His Tyr Gln Gln Leu Ala Ala Asp His Leu Glu Val Ile Ala
        835                 840                 845

Gly Asp Lys Gly Glu Ala Asn Leu Gly Leu Gly Gln Asp Val Trp Gln
850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
                885                 890                 895

Thr Ala Glu Leu Ile Arg Leu Ala Leu Thr Ser Lys Gln Lys Pro Tyr
            900                 905                 910

Thr Tyr Val Ser Thr Ile Gly Val Gly Asp Gln Ile Glu Pro Gly Lys
        915                 920                 925

Phe Val Glu Asn Ala Asp Ile Arg Gln Met Ser Ala Thr Arg Ala Ile
930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
                965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
        995                 1000                1005

Gly Ile Ala Pro Gly Ser Phe Tyr Glu Leu Asp Ala Asp Gly Asn
    1010                1015                1020

Arg Gln Arg Ala His Tyr Asp Gly Leu Pro Val Glu Phe Ile Ala
    1025                1030                1035

Ala Ala Ile Ser Thr Leu Gly Ser Gln Ile Thr Asp Ser Asp Thr
    1040                1045                1050

Gly Phe Gln Thr Tyr His Val Met Asn Pro Tyr Asp Asp Gly Val
    1055                1060                1065

Gly Leu Asp Glu Tyr Val Asp Trp Leu Val Asp Ala Gly Tyr Ser
    1070                1075                1080

Ile Glu Arg Ile Ala Asp Tyr Ser Glu Trp Leu Arg Arg Phe Glu
    1085                1090                1095

Thr Ser Leu Arg Ala Leu Pro Asp Arg Gln Arg Gln Tyr Ser Leu
    1100                1105                1110

Leu Pro Leu Leu His Asn Tyr Arg Thr Pro Glu Lys Pro Ile Asn
    1115                1120                1125

Gly Ser Ile Ala Pro Thr Asp Val Phe Arg Ala Ala Val Gln Glu
    1130               1135               1140

Ala Lys Ile Gly Pro Asp Lys Asp Ile Pro His Val Ser Pro Pro
    1145               1150               1155

Val Ile Val Lys Tyr Ile Thr Asp Leu Gln Leu Leu Gly Leu Leu
    1160               1165               1170

<210> SEQ ID NO 9
<211> LENGTH: 3525
<212> TYPE: DNA
<213> ORGANISM: Mycobacterium marinum

<400> SEQUENCE: 9

| | | | | | |
|---|---|---|---|---|---|
| atgtcgccaa | tcacgcgtga | agagcggctc | gagcgccgca | tccaggacct | ctacgccaac | 60 |
| gacccgcagt | cgccgccgc | caaacccgcc | acggcgatca | ccgcagcaat | cgagcggccg | 120 |
| ggtctaccgc | tacccagat | catcgagacc | gtcatgaccg | gatacgccga | tcggccggct | 180 |
| ctcgctcagc | gctcggtcga | attcgtgacc | gacgccggca | ccggccacac | cacgctgcga | 240 |
| ctgctccccc | acttcgaaac | catcagctac | ggcgagcttt | ggaccgcat | cagcgcactg | 300 |
| gccgacgtgc | tcagcaccga | acagacggtg | aaaccgggcg | accgggtctg | cttgttgggc | 360 |
| ttcaacagcg | tcgactacgc | cacgatcgac | atgactttgg | cgcggctggg | cgcggtggcc | 420 |
| gtaccactgc | agaccagcgc | ggcgataacc | cagctgcagc | cgatcgtcgc | cgagacccag | 480 |
| cccaccatga | tcgcggccag | cgtcgacgca | ctcgctgacg | ccaccgaatt | ggctctgtcc | 540 |
| ggtcagaccg | ctacccgagt | cctggtgttc | gaccaccacc | ggcaggttga | cgcacaccgc | 600 |
| gcagcggtcg | aatccgcccg | ggagcgcctg | gccggctcgg | cggtcgtcga | accctggcc | 660 |
| gaggccatcg | cgcgcggcga | cgtgccccgc | ggtgcgtccg | ccggctcggc | gcccggcacc | 720 |
| gatgtgtccg | acgactcgct | cgcgctactg | atctacacct | cgggcagcac | gggtgcgccc | 780 |
| aagggcgcga | tgtaccccccg | acgcaacgtt | gcgaccttct | ggcgcaagcg | cacctggttc | 840 |
| gaaggcggct | acgagccgtc | gatcacgctg | aacttcatgc | caatgagcca | cgtcatgggc | 900 |
| cgccaaatcc | tgtacggcac | gctgtgcaat | ggcggcaccg | cctacttcgt | ggcgaaaagc | 960 |
| gatctctcca | ccttgttcga | agacctggcg | ctggtgcggc | ccaccgagct | gaccttcgtg | 1020 |
| ccgcgcgtgt | gggacatggt | gttcgacgag | tttcagagtg | aggtcgaccg | ccgcctggtc | 1080 |
| gacggcgccg | accgggtcgc | gctcgaagcc | caggtcaagg | ccgagatacg | caacgacgtg | 1140 |
| ctcggtggac | ggtataccag | cgcactgacc | ggctccgccc | ctatctccga | cgagatgaag | 1200 |
| gcgtgggtcg | aggagctgct | cgacatgcat | ctggtcgagg | gctacggctc | caccgaggcc | 1260 |
| gggatgatcc | tgatcgacgg | agccattcgg | cgcccggcgg | tactcgacta | caagctggtc | 1320 |
| gatgttcccg | acctgggtta | cttcctgacc | gaccggccac | atccgcgggg | cgagttgctg | 1380 |
| gtcaagaccg | atagtttgtt | cccgggctac | taccagcgag | ccgaagtcac | cgccgacgtg | 1440 |
| ttcgatgctg | acggcttcta | ccggaccggc | gacatcatgg | ccgaggtcgg | ccccgaacag | 1500 |
| ttcgtgtacc | tcgaccgccg | caacaacgtg | ttgaagctgt | cgcagggcga | gttcgtcacc | 1560 |
| gtctccaaac | tcgaagcggt | gtttggcgac | agcccactgg | tacggcagat | ctacatctac | 1620 |
| ggcaacagcg | cccgtgccta | cctgttggcg | gtgatcgtcc | ccacccagga | ggcgctggac | 1680 |
| gccgtgcctg | tcgaggagct | caaggcgcgg | ctgggcgact | cgctgcaaga | ggtcgcaaag | 1740 |
| gccgccggcc | tgcagtccta | cgagatcccg | cgcgacttca | tcatcgaaac | aacaccatgg | 1800 |
| acgctggaga | acggcctgct | caccggcatc | cgcaagttgg | ccaggccgca | gctgaaaaag | 1860 |

-continued

```
cattacggcg agcttctcga gcagatctac acggacctgg cacacggcca ggccgacgaa   1920
ctgcgctcgc tgcgccaaag cggtgccgat gcgccggtgc tggtgacggt gtgccgtgcg   1980
gcggccgcgc tgttgggcgg cagcgcctct gacgtccagc ccgatgcgca cttcaccgat   2040
ttgggcggcg actcgctgtc ggcgctgtcg ttcaccaacc tgctgcacga gatcttcgac   2100
atcgaagtgc cggtgggcgt catcgtcagc cccgccaacg acttgcaggc cctggccgac   2160
tacgtcgagg cggctcgcaa acccggctcg tcacggccga ccttcgcctc ggtccacggc   2220
gcctcgaatg ggcaggtcac cgaggtgcat gccggtgacc tgtccctgga caaattcatc   2280
gatgccgcaa ccctggccga agctccccgg ctgcccgccg caaacaccca agtgcgcacc   2340
gtgctgctga ccggcgccac cggcttcctc gggcgctacc tggccctgga atggctggag   2400
cggatggacc tggtcgacgg caaactgatc tgcctggtcc gggccaagtc cgacaccgaa   2460
gcacgggcgc ggctggacaa gacgttcgac agcggcgacc ccgaactgct ggcccactac   2520
cgcgcactgg ccggcgacca cctcgaggtg ctcgccggtg acaagggcga agccgacctc   2580
ggactggacc ggcagacctg gcaacgcctg gccgacacgg tcgacctgat cgtcgacccc   2640
gcggccctgg tcaaccacgt actgccatac agccagctgt tcgggcccaa cgcgctgggc   2700
accgccgagc tgctgcggct ggcgctcacc tccaagatca agccctacag ctacacctcg   2760
acaatcggtg tcgccgacca gatcccgccg tcggcgttca ccgaggacgc cgacatccgg   2820
gtcatcagcg ccacccgcgc ggtcgacgac agctacgcca atggctactc gaacagcaag   2880
tgggccggcg aggtgctgtt gcgcgaggcg catgacctgt gtggcctgcc ggttgcggtg   2940
ttccgctgcg acatgatcct ggccgacacc acatgggcgg gacagctcaa tgtgccggac   3000
atgttcaccc ggatgatcct gagcctggcg gccaccggta tcgcgccggg ttcgttctat   3060
gagcttgcgg ccgacggcgc ccggcaacgc gcccactatg acggtctgcc cgtcgagttc   3120
atcgccgagg cgatttcgac tttgggtgcg cagagccagg atggtttcca cacgtatcac   3180
gtgatgaacc cctacgacga cggcatcgga ctcgacgagt tcgtcgactg gctcaacgag   3240
tccggttgcc ccatccagcg catcgctgac tatggcgact ggctgcagcg cttcgaaacc   3300
gcactgcgcg cactgcccga tcggcagcgg cacagctcac tgctgccgct gttgcacaac   3360
tatcggcagc cggagcggcc cgtccgcggg tcgatcgccc ctaccgatcg cttccgggca   3420
gcggtgcaag aggccaagat cggccccgac aaagacattc cgcacgtcgg cgcgccgatc   3480
atcgtgaagt acgtcagcga cctgcgccta ctcggcctgc tctaa                   3525
```

<210> SEQ ID NO 10
<211> LENGTH: 1174
<212> TYPE: PRT
<213> ORGANISM: Mycobacterium marinum

<400> SEQUENCE: 10

```
Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
```

```
            85                  90                  95
Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
            115                 120                 125

Ile Asp Met Thr Leu Ala Arg Leu Gly Ala Val Ala Val Pro Leu Gln
            130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                    165                 170                 175

Leu Ala Leu Ser Gly Gln Thr Ala Thr Arg Val Leu Val Phe Asp His
                    180                 185                 190

His Arg Gln Val Asp Ala His Arg Ala Ala Val Glu Ser Ala Arg Glu
                    195                 200                 205

Arg Leu Ala Gly Ser Ala Val Val Glu Thr Leu Ala Glu Ala Ile Ala
                    210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                    245                 250                 255

Thr Gly Ala Pro Lys Gly Ala Met Tyr Pro Arg Arg Asn Val Ala Thr
                    260                 265                 270

Phe Trp Arg Lys Arg Thr Trp Phe Glu Gly Gly Tyr Glu Pro Ser Ile
                    275                 280                 285

Thr Leu Asn Phe Met Pro Met Ser His Val Met Gly Arg Gln Ile Leu
                    290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                    325                 330                 335

Leu Thr Phe Val Pro Arg Val Trp Asp Met Val Phe Asp Glu Phe Gln
                    340                 345                 350

Ser Glu Val Asp Arg Arg Leu Val Asp Gly Ala Asp Arg Val Ala Leu
                    355                 360                 365

Glu Ala Gln Val Lys Ala Glu Ile Arg Asn Asp Val Leu Gly Gly Arg
                    370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                    405                 410                 415

Ser Thr Glu Ala Gly Met Ile Leu Ile Asp Gly Ala Ile Arg Arg Pro
                    420                 425                 430

Ala Val Leu Asp Tyr Lys Leu Val Asp Val Pro Asp Leu Gly Tyr Phe
                    435                 440                 445

Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                    485                 490                 495

Gly Pro Glu Gln Phe Val Tyr Leu Asp Arg Arg Asn Asn Val Leu Lys
                    500                 505                 510
```

```
Leu Ser Gln Gly Glu Phe Val Thr Val Ser Lys Leu Glu Ala Val Phe
        515                 520                 525

Gly Asp Ser Pro Leu Val Arg Gln Ile Tyr Ile Tyr Gly Asn Ser Ala
    530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
        595                 600                 605

Gly Ile Arg Lys Leu Ala Arg Pro Gln Leu Lys Lys His Tyr Gly Glu
    610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
        675                 680                 685

Leu Ser Phe Thr Asn Leu Leu His Glu Ile Phe Asp Ile Glu Val Pro
    690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
    770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
    850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940
```

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
        995                 1000                1005

Leu Ala Ala Thr Gly Ile Ala Pro Gly Ser Phe Tyr Glu Leu Ala
    1010                1015                1020

Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
    1085                1090                1095

Glu Thr Ala Leu Arg Ala Leu Pro Asp Arg Gln Arg His Ser Ser
    1100                1105                1110

Leu Leu Pro Leu Leu His Asn Tyr Arg Gln Pro Glu Arg Pro Val
    1115                1120                1125

Arg Gly Ser Ile Ala Pro Thr Asp Arg Phe Arg Ala Ala Val Gln
    1130                1135                1140

Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu

<210> SEQ ID NO 11
<211> LENGTH: 3522
<212> TYPE: DNA
<213> ORGANISM: Artificial Sequence
<220> FEATURE:
<223> OTHER INFORMATION: Description of Artificial Sequence: Synthetic
      carboxylic acid reductase polynucleotide
      designated 891GA

<400> SEQUENCE: 11
atgagcaccg caacccatga tgaacgtctg gatcgtcgtg ttcatgaact gattgcaacc      60
gatccgcagt ttgcagcagc acagccggat cctgcaatta ccgcagcact ggaacagcct     120
ggtctgcgtc tgccgcagat tattcgtacc gttctggatg ttatgcaga tcgtccggca     180 ctgggtcagc gtgttgttga atttgttacc gatgcaaaaa ccggtcgtac cagcgcacag     240
ctgctgcctc gttttgaaac cattacctat agcgaagttg cacagcgtgt tagcgcactg     300
ggtcgtgcac tgagtgatga tgcagttcat ccgggtgatc gtgtttgtgt tctgggtttt     360
aatagcgttg attatgccac cattgatatg gcactgggtg caattggtgc agttagcgtt     420
ccgctgcaga ccagcgcagc aattagcagc ctgcagccga ttgttgcaga aaccgaaccg     480
accctgattg caagcagcgt taatcagctg tcagatgcag ttcagctgat taccggtgca     540
gaacaggcac cgacccgtct ggttgttttt gattatcatc cgcaggttga tgatcagcgt     600

```
gaagcagttc aggatgcagc agcacgtctg agcagcaccg gtgttgcagt tcagaccctg    660
gcagaactgc tggaacgtgg taaagatctg cctgcagttg cagaaccgcc tgcagatgaa    720
gatagcctgg cactgctgat ttataccagc ggtagcacag gtgcaccgaa aggtgcaatg    780
tatccgcaga gcaatgttgg taaaatgtgg cgtcgtggta gcaaaaattg gtttggtgaa    840
agcgcagcaa gcattaccct gaatttcatg ccgatgagcc atgttatggg tcgtagcatt    900
ctgtatggca ccctgggtaa tggtggcacc gcatattttg cagcacgtag cgatctgagc    960
accctgctgg aagatctgga actggttcgt ccgaccgaac tgaattttgt tccgcgtatt   1020
tgggaaaccc tgtatggtga atttcagcgt caggttgaac gtcgtctgag cgaagctggc   1080
gatgccggtg aacgtcgtgc agttgaagca gaagttctgg cagaacagcg tcagtatctg   1140
ctgggtggtc gttttacctt tgcaatgacc ggtagcgcac cgattagtcc ggaactgcgt   1200
aattgggttg aaagcctgct ggaaatgcat ctgatggatg gctatggtag caccgaagca   1260
ggtatggttc tgtttgatgg cgaaattcag cgtccgcctg tgattgatta taaactggtt   1320
gatgttccgg atctgggtta ttttagcacc gatcgtccgc atccgcgtgg tgaactgctg   1380
ctgcgtaccg aaaatatgtt tccgggttat tataaacgtg cagaaaccac cgcaggcgtt   1440
tttgatgaag atggttatta tcgtaccggt gatgtgtttg cagaaattgc accggatcgt   1500
ctggtttatg ttgatcgtcg taataatgtt ctgaaactgg cacagggtga atttgtgacc   1560
ctggccaaac tggaagcagt ttttggtaat agtccgctga ttcgtcagat ttatgtgtat   1620
ggtaatagcg cacagccgta tctgctggca gttgttgttc cgaccgaaga ggcactggca   1680
agcggtgatc cggaaaccct gaaaccgaaa attgcagata gcctgcagca ggttgcaaaa   1740
gaagcaggtc tgcagagcta tgaagttccg cgtgattttt attattgaaac cacccegttt   1800
agcctggaaa atggtctgct gaccggtatt cgtaaactgg catggccgaa actgaaacag   1860
cattatggtg aacgcctgga acaaatgtat gcagatctgg cagcaggtca ggcaaatgaa   1920
ctggccgaac tgcgtcgtaa tggtgcacag gcaccggttc tgcagaccgt tagccgtgca   1980
gccggtgcaa tgctgggtag cgcagccagc gatctgagtc cggatgcaca tttttaccgat   2040
ctgggtggtg atagcctgag cgcactgacc tttggtaatc tgctgcgtga aattttttgat   2100
gttgatgtgc cggttggtgt tattgttagt ccggctaatg atctggcagc cattgcaagc   2160
tatattgaag cagaacgtca gggtagcaaa cgtccgacct tgcaagcgt tcatggtcgt   2220
gatgcaaccg ttgttcgtgc agcagatctg accctggata aatttctgga tgcagaaacc   2280
ctggcagcag caccgaatct gccgaaaccg gcaaccgaag ttcgtaccgt gctgctgaca   2340
ggtgcaaccg gttttctggg tcgttatctg gcactggaat ggctggaacg tatggatatg   2400
gttgatggta aagttattgc actggttcgt gcccgtagtg atgaagaagc acgcgcacgt   2460
ctggataaaa cctttgatag tggtgatccg aaactgctgg cacattatca gcagctggct   2520
gcagatcatc tggaagttat tgccggtgat aaaggtgaag caaatctggg tctgggtcag   2580
gatgtttggc agcgtctggc agataccgtt gatgttattg tggatccggc agcactggtt   2640
aatcatgttc tgccgtatag cgaactgttt ggtccgaatg cactgggcac cgcagaactg   2700
attcgtctgg cactgaccag caaacagaaa ccgtatacct atgttagcac cattggtgtt   2760
ggcgatcaga ttgaaccggg taaatttgtt gaaaatgccg atattcgtca gatgagcgca   2820
acccgtgcaa ttaatgatag ctatgcaaat ggctacggca atagcaaatg gcaggcgaa   2880
gttctgctgc gcgaagcaca tgatctgtgt ggtctgccgg ttgcagtttt tcgttgtgat   2940
atgattctgg ccgataccac ctatgcaggt cagctgaatc tgccggatat gtttacccgt   3000
```

-continued

```
ctgatgctga gcctggttgc aaccggtatt gcaccgggta gcttttatga actggatgca      3060
gatggtaatc gtcagcgtgc acattatgat ggcctgccgg ttgaatttat tgcagcagcc      3120
attagcaccc tgggttcaca gattaccgat agcgataccg ttttcagac ctatcatgtt       3180 atgaacccgt atgatgatgg tgttggtctg gatgaaatg ttgattggct ggttgatgcc       3240
ggttatagca ttgaacgtat tgcagattat agcgaatggc tgcgtcgctt tgaaacctca      3300
ctgcgtgcac tgccggatcg tcagcgccag tatagcctgc tgccgctgct gcacaattat      3360
cgtacaccgg aaaaaccgat taatggtagc attgcaccga ccgatgtttt tcgtgcagcc      3420
gttcaagaag ccaaaattgg tccggataaa gatattccgc atgttagccc tccggtgatt      3480
gttaaatata ttaccgatct gcagctgctg ggtctgctgt aa                         3522
```

<210> SEQ ID NO 12
<211> LENGTH: 1173
<212> TYPE: PRT
<213> ORGANISM: Artificial Sequence
<220> FEATURE:
<223> OTHER INFORMATION: Description of Artificial Sequence: Synthetic carboxylic acid reductase polypeptide designated 891GA

<400> SEQUENCE: 12

```
Met Ser Thr Ala Thr His Asp Glu Arg Leu Asp Arg Arg Val His Glu
1               5                  10                  15

Leu Ile Ala Thr Asp Pro Gln Phe Ala Ala Ala Gln Pro Asp Pro Ala
                20                  25                  30

Ile Thr Ala Ala Leu Glu Gln Pro Gly Leu Arg Leu Pro Gln Ile Ile
            35                  40                  45

Arg Thr Val Leu Asp Gly Tyr Ala Asp Arg Pro Ala Leu Gly Gln Arg
        50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
        115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205

Arg Leu Ser Ser Thr Gly Val Ala Val Gln Thr Leu Ala Glu Leu Leu
    210                 215                 220

Glu Arg Gly Lys Asp Leu Pro Ala Val Ala Glu Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270
```

```
Gly Ser Lys Asn Trp Phe Gly Glu Ser Ala Ala Ser Ile Thr Leu Asn
        275                 280                 285

Phe Met Pro Met Ser His Val Met Gly Arg Ser Ile Leu Tyr Gly Thr
    290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
            340                 345                 350

Glu Arg Arg Leu Ser Glu Ala Gly Asp Ala Gly Glu Arg Arg Ala Val
        355                 360                 365

Glu Ala Glu Val Leu Ala Glu Gln Arg Gln Tyr Leu Leu Gly Gly Arg
    370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                405                 410                 415

Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
        435                 440                 445

Ser Thr Asp Arg Pro His Pro Arg Gly Glu Leu Leu Leu Arg Thr Glu
    450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
        515                 520                 525

Gly Asn Ser Pro Leu Ile Arg Gln Ile Tyr Val Tyr Gly Asn Ser Ala
    530                 535                 540

Gln Pro Tyr Leu Leu Ala Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
        595                 600                 605

Gly Ile Arg Lys Leu Ala Trp Pro Lys Leu Lys Gln His Tyr Gly Glu
    610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
        675                 680                 685

Leu Thr Phe Gly Asn Leu Leu Arg Glu Ile Phe Asp Val Asp Val Pro
```

```
              690             695             700
Val Gly Val Ile Val Ser Pro Ala Asn Asp Leu Ala Ile Ala Ser
705             710             715             720

Tyr Ile Glu Ala Glu Arg Gln Gly Ser Lys Arg Pro Thr Phe Ala Ser
                725             730             735

Val His Gly Arg Asp Ala Thr Val Val Arg Ala Ala Asp Leu Thr Leu
            740             745             750

Asp Lys Phe Leu Asp Ala Glu Thr Leu Ala Ala Ala Pro Asn Leu Pro
            755             760             765

Lys Pro Ala Thr Glu Val Arg Thr Val Leu Leu Thr Gly Ala Thr Gly
    770             775             780

Phe Leu Gly Arg Tyr Leu Ala Leu Glu Trp Leu Glu Arg Met Asp Met
785             790             795             800

Val Asp Gly Lys Val Ile Ala Leu Val Arg Ala Arg Ser Asp Glu Glu
                805             810             815

Ala Arg Ala Arg Leu Asp Lys Thr Phe Asp Ser Gly Asp Pro Lys Leu
                820             825             830

Leu Ala His Tyr Gln Gln Leu Ala Ala Asp His Leu Glu Val Ile Ala
            835             840             845

Gly Asp Lys Gly Glu Ala Asn Leu Gly Leu Gly Gln Asp Val Trp Gln
850             855             860

Arg Leu Ala Asp Thr Val Asp Val Ile Val Asp Pro Ala Ala Leu Val
865             870             875             880

Asn His Val Leu Pro Tyr Ser Glu Leu Phe Gly Pro Asn Ala Leu Gly
                885             890             895

Thr Ala Glu Leu Ile Arg Leu Ala Leu Thr Ser Lys Gln Lys Pro Tyr
            900             905             910

Thr Tyr Val Ser Thr Ile Gly Val Gly Asp Gln Ile Glu Pro Gly Lys
    915             920             925

Phe Val Glu Asn Ala Asp Ile Arg Gln Met Ser Ala Thr Arg Ala Ile
    930             935             940

Asn Asp Ser Tyr Ala Asn Gly Tyr Gly Asn Ser Lys Trp Ala Gly Glu
945             950             955             960

Val Leu Leu Arg Glu Ala His Asp Leu Cys Gly Leu Pro Val Ala Val
            965             970             975

Phe Arg Cys Asp Met Ile Leu Ala Asp Thr Thr Tyr Ala Gly Gln Leu
            980             985             990

Asn Leu Pro Asp Met Phe Thr Arg Leu Met Leu Ser Leu Val Ala Thr
            995             1000            1005

Gly Ile Ala Pro Gly Ser Phe Tyr Glu Leu Asp Ala Asp Gly Asn
    1010            1015            1020

Arg Gln Arg Ala His Tyr Asp Gly Leu Pro Val Glu Phe Ile Ala
    1025            1030            1035

Ala Ala Ile Ser Thr Leu Gly Ser Gln Ile Thr Asp Ser Asp Thr
    1040            1045            1050

Gly Phe Gln Thr Tyr His Val Met Asn Pro Tyr Asp Asp Gly Val
    1055            1060            1065

Gly Leu Asp Glu Tyr Val Asp Trp Leu Val Asp Ala Gly Tyr Ser
    1070            1075            1080

Ile Glu Arg Ile Ala Asp Tyr Ser Glu Trp Leu Arg Arg Phe Glu
    1085            1090            1095

Thr Ser Leu Arg Ala Leu Pro Asp Arg Gln Arg Gln Tyr Ser Leu
    1100            1105            1110
```

-continued

| | | | | | | | | | | | | |
|---|---|---|---|---|---|---|---|---|---|---|---|---|
| Leu | Pro 1115 | Leu | Leu | His | Asn | Tyr 1120 | Arg | Thr | Pro | Glu | Lys 1125 | Pro Ile Asn |
| Gly | Ser 1130 | Ile | Ala | Pro | Thr | Asp 1135 | Val | Phe | Arg | Ala | Ala 1140 | Val Gln Glu |
| Ala | Lys 1145 | Ile | Gly | Pro | Asp | Lys 1150 | Asp | Ile | Pro | His | Val 1155 | Ser Pro Pro |
| Val | Ile 1160 | Val | Lys | Tyr | Ile | Thr 1165 | Asp | Leu | Gln | Leu | Leu 1170 | Gly Leu Leu |